(12) United States Patent
Brias et al.

(10) Patent No.: US 10,842,779 B2
(45) Date of Patent: Nov. 24, 2020

(54) HETEROCYCLIC COMPOUNDS AND THEIR USE IN PREVENTING OR TREATING BACTERIAL INFECTIONS

(71) Applicant: MUTABILIS, Paris (FR)

(72) Inventors: Julie Brias, Paris (FR); Sophie Chasset, Nandy (FR); Francis Chevreuil, Chantilly (FR); Nicolas Lecointe, Paris (FR); Benoit Ledoussal, Pommerit Jaudy (FR); Frédéric Le Strat, Combs La Ville (FR); Julien Barbion, Sannois (FR)

(73) Assignee: MUTABILIS, Paris (FR)

( * ) Notice: Subject to any disclaimer, the term of this patent is extended or adjusted under 35 U.S.C. 154(b) by 0 days.

(21) Appl. No.: 16/065,303

(22) PCT Filed: Dec. 22, 2016

(86) PCT No.: PCT/EP2016/082291
§ 371 (c)(1),
(2) Date: Jun. 22, 2018

(87) PCT Pub. No.: WO2017/109025
PCT Pub. Date: Jun. 29, 2017

(65) Prior Publication Data
US 2019/0175561 A1   Jun. 13, 2019

(30) Foreign Application Priority Data
Dec. 23, 2015   (EP) ..................... 15307125

(51) Int. Cl.
*C07D 513/18* (2006.01)
*A61K 31/4188* (2006.01)
*A61P 31/04* (2006.01)
*A61K 45/06* (2006.01)

(52) U.S. Cl.
CPC .......... *A61K 31/4188* (2013.01); *A61P 31/04* (2018.01); *C07D 513/18* (2013.01); *A61K 45/06* (2013.01)

(58) Field of Classification Search
CPC .................................................. C07D 513/18
See application file for complete search history.

(56) References Cited

U.S. PATENT DOCUMENTS

2009/0018329 A1   1/2009   Lampilas et al.

FOREIGN PATENT DOCUMENTS

| WO | 2013030735 A1 | 3/2013 |
| WO | 2013/150296 A1 | 10/2013 |

OTHER PUBLICATIONS

International Search Report and Written Opinion for PCT/EP2016/082291 dated Jan. 25, 2017.
PUBCHEM Chemistry Database, Database Accession No. SID202030843, Sep. 8, 2014, XP002757774.

*Primary Examiner* — Bruck Kifle
(74) *Attorney, Agent, or Firm* — Thompson Coburn LLP; Steven M. Ritchey

(57) ABSTRACT

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

18 Claims, No Drawings

HETEROCYCLIC COMPOUNDS AND THEIR USE IN PREVENTING OR TREATING BACTERIAL INFECTIONS

CROSS-REFERENCE TO RELATED APPLICATIONS

This application claims the a national stage application of PCT/EP2016/082291, filed on Dec. 22, 2016, which claims the benefit of EP 15307125.3, filed on Dec. 23, 2015, each of which is incorporated herein by reference in its entirety.

The present invention relates to heterocyclic compounds, their process of preparation, pharmaceutical compositions comprising these compounds and use thereof, optionally in combination with other antibacterial agents and/or beta-lactam compounds, for the prevention or treatment of bacterial infections. The present invention also relates to the use of these compounds as β-lactamase inhibitors and/or as antibacterial agents.

It has been described that there is a continuous evolution of antibacterial resistance which could lead to bacterial strains against which known antibacterial compounds are inefficient.

There is thus a need to provide effective compounds and composition that can overcome bacterial antibiotic resistance.

The objective of the present invention is to provide heterocyclic compounds that can be used as antibacterial agents and/or beta-lactamase inhibitors.

An objective of the present invention is also to provide heterocyclic compounds that can be used for the prevention or for the treatment of bacterial infections.

Another objective of the present invention is to provide heterocyclic compounds that can overcome bacterial antibiotic resistance.

An objective of the invention is also to provide pharmaceutical compositions comprising such heterocyclic compounds, optionally in combination with one or more other antibacterial agent, for the prevention or for the treatment of bacterial infections and which can overcome bacterial antibiotic resistance.

Other objectives will appear throughout the description of the invention.

The present invention thus provides a compound of formula (I)

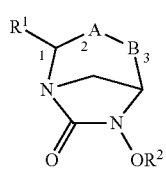

(I)

wherein
A-B represents
  a CH=CH double bond or
  a ring W, unsubstituted or substituted by one or more T, represents a phenyl group or a 5- or 6-membered aromatic heterocycle comprising at least one heteroatom selected from the group consisting of O, N, N($R^3$), S, S(O) or S(O)$_2$;
$R^1$ represents a carbon-linked, unsubstituted or substituted by one or more $T^1$, aromatic, totally or partially unsaturated, 5- or 6-membered heterocycle comprising at least one nitrogen atom;

$R^2$ represents $SO_3H$, $CFHCO_2H$ or $CF_2CO_2H$;
$R^3$ independently represents hydrogen; —$(CH_2)_m$—CN; —$(CH_2)_nOC(O)Q^1$; —$(CH_2)_m$—$C(O)OQ^1$; —$(CH_2)_n$—$OC(O)OQ^1$; —$(CH_2)_n$—$OC(O)NQ^1Q^2$; —$(CH_2)_m$—$C(O)NQ^1Q^2$; —$(CH_2)_m$—$C(O)NQ^1OQ^2$; —$(CH_2)_m$—$C(O)NQ^1$-$NQ^1Q^2$; —$(CH_2)_n$—$NQ^1C(O)Q^2$; —$(CH_2)_n$—$NQ^1C(O)OQ^2$; —$(CH_2)_n$—$NQ^1C(O)NQ^1Q^2$; —$(CH_2)_nOQ^1$; —$(CH_2)_nNQ^1Q^2$; —$(CH_2)_n$—NH—$C(NHQ^3)$=$NQ^4$; —$(CH_2)_n$—NH—CH=$NQ^3$; —$(CH_2)_m$—$C(NHQ^3)$=$NQ^4$; —(Y)—$C_1$-$C_6$-alkyl; —(Y)—$C_1$-$C_6$-fluoroalkyl; —(Y)—$C_3$-$C_6$-cycloalkyl; —(Y)—$C_3$-$C_6$-cyclofluoroalkyl; —(Y)—$(CH_2)_p$—CN; —(Y)—$(CH_2)_pOC(O)Q^1$; —(Y)—$(CH_2)_p$—$C(O)OQ^1$; —(Y)—$(CH_2)_p$—$OC(O)OQ^1$; —(Y)—$(CH_2)_p$—$OC(O)NQ^1Q^2$; —(Y)—$(CH_2)_p$—$C(O)NQ^1Q^2$; —(Y)—$(CH_2)_p$—$C(O)NQ^1Q^2$; —(Y)—$(CH_2)_p$—$C(O)NQ^1$-$NQ^1Q^2$; —(Y)—$(CH_2)_p$—$NQ^1C(O)Q^2$; —(Y)—$(CH_2)_p$—$NQ^1C(O)OQ^2$; —(Y)—$(CH_2)_p$—$NQ^1C(O)NQ^1Q^2$; —(Y)—$(CH_2)_pOQ^1$; —(Y)—$(CH_2)_pNQ^1Q^2$; —(Y)—$(CH_2)_p$—NH—$C(NHQ^3)$=$NQ^4$; —(Y)—$(CH_2)_p$—NH—CH=$NQ^3$; —(Y)—$(CH_2)_p$—$C(NHQ^3)$=$NQ^4$; or $R^3$, unsubstituted or substituted by one or more $T^2$, independently represents -$C_1$-$C_6$-alkyl; —$C_1$-$C_6$-fluoroalkyl; —$C_3$-$C_6$-cycloalkyl; —$C_3$-$C_6$-cyclofluoroalkyl; —$(CH_2)_m$-(aromatic, totally or partially unsaturated, 4- to 6-membered heterocycle comprising at least one nitrogen atom) or —(Y)—$(CH_2)_m$-(aromatic, totally or partially unsaturated, 4- to 6-membered heterocycle comprising at least one nitrogen atom);

T and $T^1$, identical or different, independently represent a fluorine atom; O—$C_1$-$C_6$-fluoroalkyl; —$(CH_2)_m$—$C_3$-$C_6$-cyclofluoroalkyl; —$(CH_2)_m$—CN; —$(CH_2)_mOC(O)Q^1$; —$(CH_2)_m$—$C(O)OQ^1$; —$(CH_2)_m$—$OC(O)OQ^1$; —$(CH_2)_m$—$OC(O)NQ^1Q^2$; —$(CH_2)_m$—$C(O)NQ^1Q^2$; —$(CH_2)_m$—$C(O)NQ^1OQ^2$; —$(CH_2)_m$—$C(O)NQ^1$-$NQ^1Q^2$; —$(CH_2)_m$—$NQ^1C(O)Q^2$; —$(CH_2)_m$—$NQ^1C(O)OQ^2$; —$(CH_2)_m$—$NQ^1C(O)NQ^1Q^2$; —$(CH_2)_mOQ^1$; —$(CH_2)_mNQ^1Q^2$; —$(CH_2)_m$—NH—$C(NHQ^3)$=$NQ^4$; —$(CH_2)_m$—NH—CH=$NQ^3$; —$(CH_2)_m$—$C(NHQ^3)$=$NQ^4$; -(L)-$(CH_2)_p$—CN; -(L)-$(CH_2)_nOC(O)Q^1$; -(L)-$(CH_2)_pC(O)OQ^1$; -(L)-$(CH_2)_nOC(O)OQ^1$; -(L)-$(CH_2)_n$—$OC(O)NQ^1Q^2$; -(L)-$(CH_2)_p$—$C(O)NQ^1Q^2$; -(L)-$(CH_2)_p$—$C(O)NQ^1OQ^2$; -(L)-$(CH_2)_p$—$C(O)NQ^1$-$NQ^1Q^2$; -(L)-$(CH_2)_n$—$NQ^1C(O)Q^2$; -(L)-$(CH_2)_n$—$NQ^1C(O)OQ^2$; -(L)-$(CH_2)_n$—$NQ^1C(O)NQ^1Q^2$; -(L)-$(CH_2)_nOQ^1$; -(L)-$(CH_2)_nNQ^1Q^2$; -(L)-$(CH_2)_n$—NH—$C(NHQ^3)$=$NQ^4$; -(L)-$(CH_2)_n$—NH—CH=$NQ^3$; -(L)-$(CH_2)_n$—$C(NHQ^3)$=$NQ^4$; or T and $T^1$, identical or different, unsubstituted or substituted by one or more $T^3$, independently represent $C_1$-$C_6$-alkyl; $C_1$-$C_6$-fluoroalkyl; —$(CH_2)_m$—$C_3$-$C_6$-cycloalkyl; -(L)-$C_1$-$C_6$-alkyl; -(L)-$C_1$-$C_6$-fluoroalkyl; -(L)-$C_3$-$C_6$-cycloalkyl; -(L)-$C_3$-$C_6$-cyclofluoroalkyl; —$(CH_2)_m$-heterocycle; -(L)-$(CH_2)_p$-heterocycle;

$Q^1$ and $Q^2$, identical or different, independently represent a hydrogen atom; —$(CH_2)_nNHQ^3$; —$(CH_2)_n$—NH—$C(NHQ^3)$=$NQ^4$; $(CH_2)_n$—NH—CH=$NQ^3$; $(CH_2)_p$—$C(NHQ^3)$=$NQ^4$; —$(CH_2)_nOQ^3$; —$(CH_2)_pCONHQ^3$; —$(CH_2)_n$—$NHCONHQ^3$ or $Q^1$ and $Q^2$, identical or different, unsubstituted or substituted by one or more $T^3$, independently represent a $C_1$-$C_3$-alkyl; —$(CH_2)_m$-(4-, 5- or 6-membered heterocycle); or $Q^1$, $Q^2$ and the nitrogen atom to which they are bonded, form an unsubstituted or substituted by one or more $T^3$, saturated or partially unsaturated, 4-, 5- or 6-membered N comprising heterocycle optionally comprising 1, 2 or 3 further heteroatoms, preferably chosen among O, N, $NR_3$, S, SO, $SO_2$;

$Q^3$ and $Q^4$, identical or different, independently represent a hydrogen atom or a $C_1$-$C_3$-alkyl;

$T^2$ and $T^3$, identical or different, independently represent a fluorine atom; $C_1$-$C_6$-alkyl; $C_1$-$C_6$-fluoroalkyl; O—$C_1$-$C_6$-fluoroalkyl; —$(CH_2)_m$—$C_3$-$C_6$-cycloalkyl; —$(CH_2)_m$—$C_3$-$C_6$-cyclofluoroalkyl; —$(CH_2)_m$—CN; —$(CH_2)_m$OC(O)$Q^3$; —$(CH_2)_m$—C(O)O$Q^3$; —$(CH_2)_m$—OC(O)O$Q^3$; —$(CH_2)_m$—OC(O)N$Q^3Q^4$; —$(CH_2)_m$—C(O)N$Q^3Q^4$; —$(CH_2)_m$—C(O)N$Q^3$O$Q^4$; —$(CH_2)_m$—C(O)N$Q^3$-N$Q^3Q^4$; —$(CH_2)_m$—N$Q^3$C(O)$Q^4$; —$(CH_2)_m$—N$Q^3$C(O)O$Q^4$; —$(CH_2)_m$—N$Q^3$C(O)N$Q^3Q^4$; —$(CH_2)_m$O$Q^3$; —$(CH_2)_m$N$Q^3Q^4$; —$(CH_2)_m$—NH—C(NH$Q^3$)=N$Q^4$; —$(CH_2)_m$—NH—CH=N$Q^3$; —$(CH_2)_m$—C(NH$Q^3$)=N$Q^4$; -(L)-$C_1$-$C_6$-alkyl; -(L)-$C_1$-$C_6$-fluoroalkyl; -(L)-$(CH_2)_p$—$C_3$-$C_6$-cycloalkyl; -(L)-$(CH_2)_p$—$C_3$-$C_6$-cyclofluoroalkyl; -(L)-$(CH_2)_p$—CN; -(L)-$(CH_2)_p$OC(O)$Q^3$; -(L)-$(CH_2)_p$—C(O)O$Q^3$; -(L)-$(CH_2)_n$—OC(O)O$Q^3$; -(L)-$(CH_2)_n$—OC(O)N$Q^3Q^4$; -(L)-$(CH_2)_p$—C(O)N$Q^3Q^4$; -(L)-$(CH_2)_p$—C(O)N$Q^3$O$Q^4$; -(L)-$(CH_2)_p$—C(O)N$Q^3$-N$Q^3Q^4$; -(L)-$(CH_2)_n$—N$Q^3$C(O)$Q^4$; -(L)-$(CH_2)_n$—N$Q^3$C(O)O$Q^4$; -(L)-$(CH_2)_n$—N$Q^3$C(O)N$Q^3Q^4$; -(L)-$(CH_2)_n$O$Q^3$; -(L)-$(CH_2)_n$N$Q^3Q^4$; -(L)-$(CH_2)_n$—NH—C(NH$Q^3$)=N$Q^4$; -(L)-$(CH_2)_n$—NH—CH=N$Q^3$; -(L)-$(CH_2)_n$—C(NH$Q^3$)=N$Q^4$;

Y, identical or different, independently represents C=O or $S(O)_2$;

L, identical or different, independently represents O, S, $N(R^3)$, S(O) or $S(O)_2$;

m independently represents 0, 1, 2, 3 or 4;

n independently represents 2, 3 or 4;

p independently represents 1, 2, 3 or 4 when Y is C=O or 2, 3 or 4 when Y is $S(O)_2$;

wherein any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a $S(O)_2$ group;

any nitrogen atom present within a heterocycle or present within group wherein it is trisubstituted thus forming a tertiary amino group, can be further quaternized by a methyl group;

and a pharmaceutically acceptable salt, a zwitterion, an optical isomer, a racemate, a diastereoisomer, an enantiomer, a geometric isomer or a tautomer thereof.

Preferably, the heterocycle $R^1$ and W are both monocycle and are not fused with another ring.

Preferably, the compound according to the invention is selected from the compounds of formulae (A) and (B)

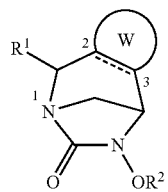

(A)

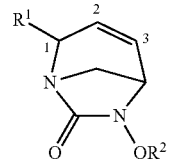

(B)

Preferably, in the compounds of the invention, W, unsubstituted or substituted by one or more T, represents
a phenyl group; or
a 5-membered aromatic heterocycle comprising at least one heteroatom selected from the group consisting of O, N, $N(R^3)$, S, S(O) or $S(O)_2$; or
a 6-membered aromatic heterocycle comprising 1, 2 or 3 nitrogen atom.

Also preferably, the compound according to the invention is selected from the compounds of formulae (A1) to (A23)

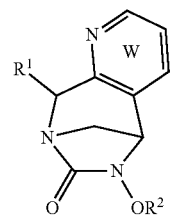

(A1)

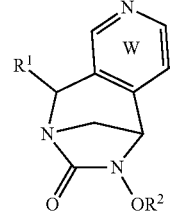

(A2)

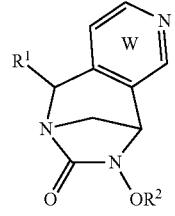

(A3)

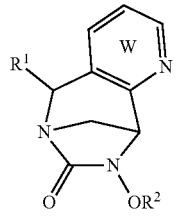

(A4)

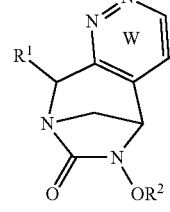

(A5)

(A6) 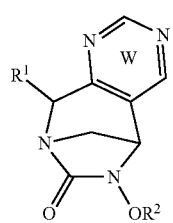
(A7) 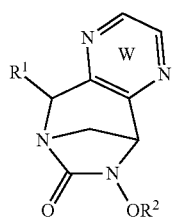
(A8) 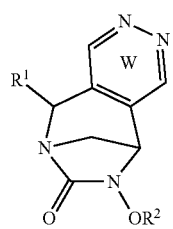
(A9) 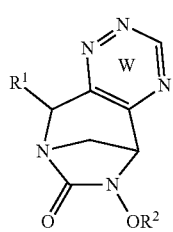
(A10) 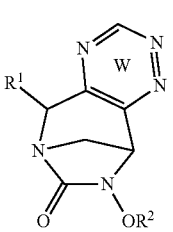
(A11) 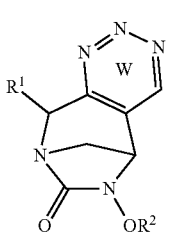
(A12) 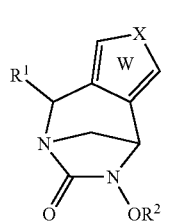
(A13) 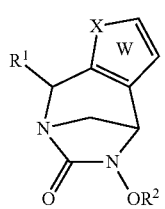
(A14) 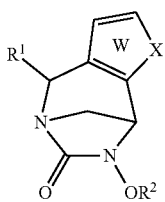
(A15) 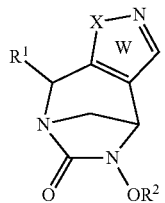
(A16) 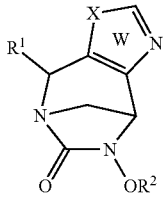
(A17) 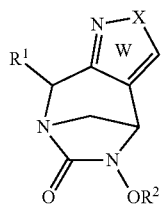
(A18) 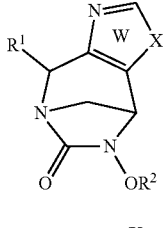
(A19) 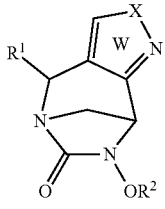

(A20) 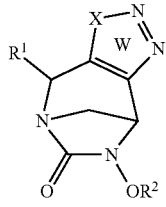

(A21) 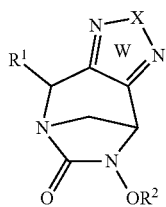

(A22) 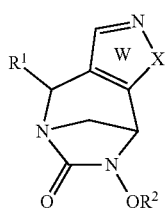

(A23) 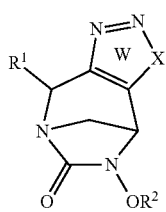

X represents O; N(R³); S; S(O) or S(O)₂;

W, unsubstituted or substituted by one or more T, R¹, R², R³ and T are defined above.

The compound according to the invention can also selected from the compounds of formulae (A24) to (A26)

(A24) 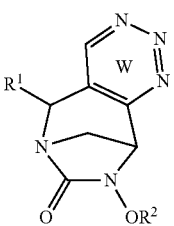

(A25)

(A26)

W, unsubstituted or substituted by one or more T, R¹, R², R³ and T are defined above.

More preferably, the compound according to the invention is selected from the compounds of formulae (I*), (A*), (B*)

(I*)

(A*)

(B*)

Preferably, the compounds of the invention are compounds of formula (A), preferably (A*). Preferably, the compounds of the invention are compounds of formula (B), preferably (B*). The invention also provides compounds of formula (A1*) to (A23*) respectively corresponding to the stereoisomers of the compounds of formulae (A1) to (A23).

(A1*)

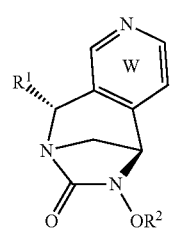 (A2*)
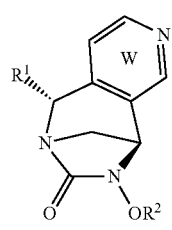 (A3*)
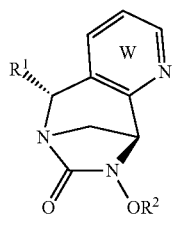 (A4*)
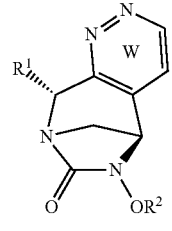 (A5*)
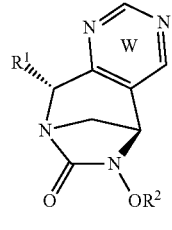 (A6*)
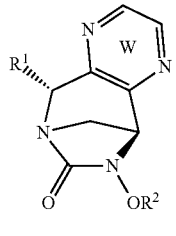 (A7*)
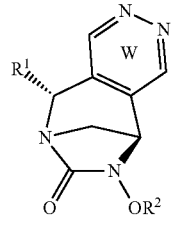 (A8*)
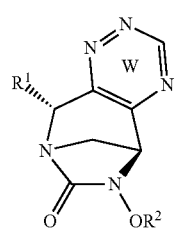 (A9*)
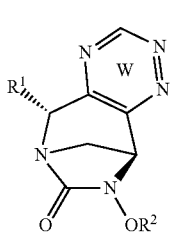 (A10*)
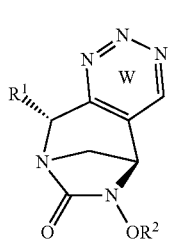 (A11*)
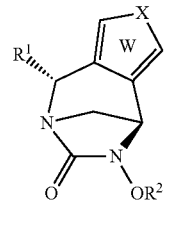 (A12*)
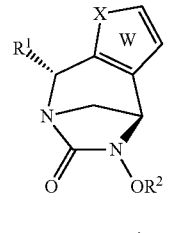 (A13*)
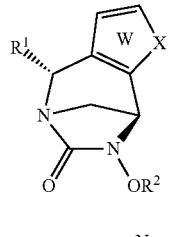 (A14*)
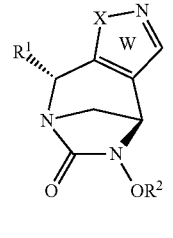 (A15*)

(A16*) 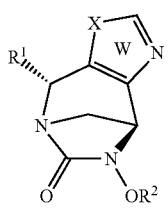

(A17*) 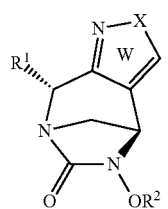

(A18*) 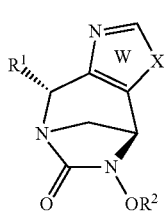

(A19*) 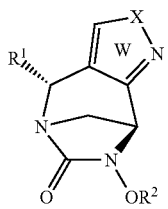

(A20*) 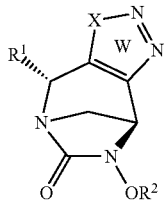

(A21*) 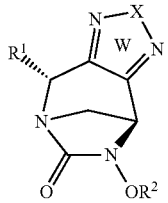

(A22*) 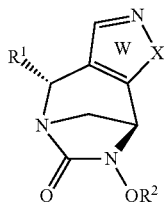

(A23*) 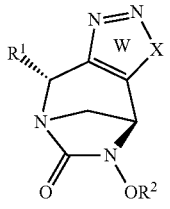

X represents O; N(R³); S; S(O) or S(O)₂;
W, unsubstituted or substituted by one or more T, R¹, R², R³ and T are defined above.

The compound according to the invention can also be selected from the compounds of formulae (A24*) to (A26*) respectively corresponding to the stereoisomers of the compounds of formulae (A24) to (A26).

(A24*) 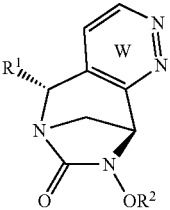

(A25*) 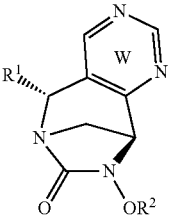

(A26*) 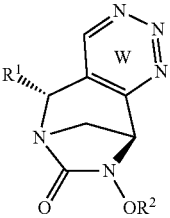

W, unsubstituted or substituted by one or more T, R¹, R², R³ and T are defined above.

Preferably, the present invention concerns compounds of formula (I) wherein W is a 6-membered aromatic heterocycle comprising one nitrogen atom or a 5-membered aromatic heterocycle, preferably, the compounds of the invention is of formula A1, A4 and A12 to A23 and A1*, A4* and A12* to A23*.

Preferably, the present invention concerns compounds of formula (I) wherein W is a 6-membered aromatic heterocycle comprising one nitrogen atom, preferably, the compounds of the invention is of formula A1, A4 and A1* and A4*.

Preferably, the present invention concerns compounds wherein W is a 5-membered aromatic heterocycle, preferably compounds of formula A12 to A23 and A12* to A23*.

Preferably, in the compounds of formula (I), (I*), (A), (A*), (B), (B*), (A1) to (A26) and (A1*) to (A26*), R¹ is chosen among oxazole, isoxazole, thiazole, isothiazole, pyrazole, imidazole, imidazoline, oxadiazole, thiadiazole, triazole, tetrazole, unsubstituted or substituted by one or more $T^1$.

Preferably, in the compounds of the invention $Q^1$, $Q^2$, identical or different, represent H, $-(CH_2)_nNH_2$; $-(CH_2)_n-NH-C(NH_2)=NH$; $-(CH_2)_nOH$; $-(CH_2)_pCONH_2$; $-(CH_2)_n-NHCONH_2$. Preferably, in the compounds of the invention $Q^3$ and $Q^4$ represent H.

Preferably, in the compounds of formula (I), (I*), (A), (A*), (B), (B*), (A1) to (A26) and (A1*) to (A26*), $R^3$ is chosen among hydrogen; $-(CH_2)_m-CN$; $-(CH_2)_m-C(O)OQ^1$; $-(CH_2)_m-C(O)NQ^1Q^2$; $-(CH_2)_m-C(O)NQ^1OQ^2$; $-(CH_2)_m-C(O)NQ^1-NQ^1Q^2$; $-(CH_2)_n-NQ^1C(O)NQ^1Q^2$; $-(CH_2)_nOQ^1$; $-(CH_2)_nNQ^1Q^2$; $-(CH_2)_n-NH-C(NHQ^3)=NQ^4$; $-(Y)-C_1-C_3$-alkyl; $-(Y)-CF_3$; $-(Y)-(CH_2)_p-CN$; $-(Y)-(CH_2)_p-C(O)OQ^1$; $-(Y)-(CH_2)_p-C(O)NQ^1Q^2$; $-(Y)-(CH_2)_p-C(O)NQ^1OQ^2$; $-(Y)-(CH_2)_p-C(O)NQ^1-NQ^1Q^2$; $-(Y)-(CH_2)_p-NQ^1C(O)Q^2$; $-(Y)-(CH_2)_p-NQ^1C(O)NQ^1Q^2$; $-(Y)-(CH_2)_pOQ^1$; $-(Y)-(CH_2)_pNQ^1Q^2$; $-(Y)-(CH_2)_n-NH-C(NHQ)=NQ^4$; Or $C_1-C_3$-alkyl; $-CF_3$; $-(CH_2)_m$-(aromatic, totally or partially unsaturated, 4- to 6-membered heterocycle comprising at least one nitrogen atom) or $-(Y)-(CH_2)_m$-(aromatic, totally or partially unsaturated, 4- to 6-membered heterocycle comprising at least one nitrogen atom). Preferably, $R^3$ is chosen among hydrogen; $-(CH_2)_m-CN$; $-(CH_2)_m-C(O)OH$; $-(CH_2)_m-C(O)NH_2$; $-(CH_2)_m-C(O)NHOH$; $-(CH_2)_m-C(O)NH-NH_2$; $-(CH_2)_n-NHC(O)NH_2$; $-(CH_2)_nOH$; $-(CH_2)_nNH_2$; $-(CH_2)_n-NH-C(NH_2)=NH$; $-(Y)-C_1-C_3$-alkyl; $-(Y)-CF_3$; $-(Y)-(CH_2)_p-CN$; $-(Y)-(CH_2)_p-C(O)OH$; $-(Y)-(CH_2)_p-C(O)NH_2$; $-(Y)-(CH_2)_p-C(O)NHOH$; $-(Y)-(CH_2)_p-C(O)NH-NH_2$; $-(Y)-(CH_2)_p-NHC(O)H$; $-(Y)-(CH_2)_p-NHC(O)NH_2$; $-(Y)-(CH_2)_pOH$; $-(Y)-(CH_2)_pNH_2$; $-(Y)-(CH_2)_n-NH-C(NH_2)=NH$; or $C_1-C_3$-alkyl; $-CF_3$; $-(CH_2)_m$-(aromatic, totally or partially unsaturated, 4- to 6-membered heterocycle comprising at least one nitrogen atom) or $-(Y)-(CH_2)_m$-(aromatic, totally or partially unsaturated, 4- to 6-membered heterocycle comprising at least one nitrogen atom).

Preferably, in the compounds of formula (I), (I*), (A), (A*), (B), (B*), (A1) to (A26) and (A1*) to (A26*), T and $T^1$, identical or different, represent F; $-OCF_3$; $-(CH_2)_m-CN$; $-(CH_2)_m-C(O)OQ^1$; $-(CH_2)_m-C(O)NQ^1Q^2$; $-(CH_2)_m-C(O)NQ^1OQ^2$; $-(CH_2)_m-C(O)NQ^1-NQ^1Q^2$; $-(CH_2)_m-NQ^1C(O)NQ^1Q^2$; $-(CH_2)_mOQ^1$; $-(CH_2)_mNQ^1Q^2$; $-(CH_2)_m-NH-C(NHQ^3)=NQ^4$; -(L)-(CH_2)_p-CN$; -(L)-(CH_2)_p-C(O)OQ^1$; -(L)-(CH_2)_p-C(O)NQ^1Q^2$; -(L)-(CH_2)_p-C(O)NQ^1OQ^2$; -(L)-(CH_2)_p-C(O)NQ^1-NQ^1Q^2$; -(L)-(CH_2)_n-NQ^1C(O)NQ^1Q^2$; -(L)-(CH_2)_nOQ^1$; -(L)-(CH_2)_nNQ^1Q^2$; -(L)-(CH_2)_n-NH-C(NHQ^3)=NQ^4$; or T and $T^1$, identical or different, unsubstituted or substituted by one or more $T^3$, independently represent $C_1-C_3$-alkyl; $C_1-C_3$-fluoroalkyl; -(L)-$C_1-C_3$-alkyl; -(L)-$C_1-C_3$-fluoroalkyl; $-(CH_2)_m$-heterocycle; -(L)-$(CH_2)_p$-heterocycle. Preferably T and $T^1$, identical or different, represent F; $-OCF_3$; $-(CH_2)_m-CN$; $-(CH_2)_m-C(O)OH$; $-(CH_2)_m-C(O)NH_2$; $-(CH_2)_m-C(O)NHOH$; $-(CH_2)_m-C(O)NH-NH_2$; $-(CH_2)_m-NHC(O)NH_2$; $-(CH_2)_mOH$; $-(CH_2)_mNH_2$; $-(CH_2)_m-NH-C(NHQ^3)=NQ^4$; -(L)-(CH_2)_p-CN$; -(L)-(CH_2)_p-C(O)OH$; -(L)-(CH_2)_p-C(O)NH_2$; -(L)-(CH_2)_p-C(O)NHOH$; -(L)-(CH_2)_p-C(O)NH-NH_2$; -(L)-(CH_2)_n-NHC(O)NH_2$; -(L)-(CH_2)_nOH$; -(L)-(CH_2)_nNH_2$; -(L)-(CH_2)_n-NH-C(NHQ^3)=NQ^4$; or T and $T^1$, identical or different, unsubstituted or substituted by one or more $T^3$, independently represent $C_1-C_3$-alkyl; $C_1-C_3$-fluoroalkyl; -(L)-$C_1-C_3$-alkyl; -(L)-$C_1-C_3$-fluoroalkyl; $-(CH_2)_m$-heterocycle; -(L)-$(CH_2)_p$-heterocycle.

Preferably, in the compounds of formula (I), (I*), (A), (A*), (B), (B*), (A1) to (A26) and (A1*) to (A26*), $T^2$ and $T^3$, identical or different, represent F; Me; CF3; $-OCF_3$; $-(CH_2)_m-CN$; $-(CH_2)_m-C(O)OQ^3$; $-(CH_2)_m-C(O)NQ^3Q^4$; $-(CH_2)_m-C(O)NQ^3OQ^4$; $-(CH_2)_m-C(O)NQ^3-NQ^3Q^4$; $-(CH_2)_m-NQ^3C(O)NQ^3Q^4$; $-(CH_2)_mOQ^3$; $-(CH_2)_mNQ^3Q^4$; $-(CH_2)_m-NH-C(NHQ^3)=NQ^4$; -(L)-Me; -(L)-$C_1-C_3$-fluoroalkyl; -(L)-(CH_2)_p-CN-(L)-(CH_2)_p-C(O)OQ^3$; -(L)-(CH_2)_p-C(O)NQ^3Q^4$; -(L)-(CH_2)_p-C(O)NQ^3OQ^4$; -(L)-(CH_2)_p-C(O)NQ^3-NQ^3Q^4$; -(L)-(CH_2)_n-NQ^3C(O)NQ^3Q^4$; -(L)-(CH_2)_nOQ^3$; -(L)-(CH_2)_nNQ^3Q^4$; -(L)-(CH_2)_n-NH-C(NHQ^3)=NQ^4$. Preferably, $T^2$ and $T^3$, identical or different, represent F; Me; CF3; $-OCF_3$; $-(CH_2)_m-CN$; $-(CH_2)_m-C(O)OH$; $-(CH_2)_m-C(O)NH_2$; $-(CH_2)_m-C(O)NHOH$; $-(CH_2)_m-C(O)NH-NH_2$; $-(CH_2)_m-NHC(O)NH_2$; $-(CH_2)_mOH$; $-(CH_2)_m-NH-C(NH_2)=NH$; -(L)-Me; -(L)-$C_1-C_3$-fluoroalkyl; -(L)-(CH_2)_p-CN-(L)-(CH_2)_p-C(O)OH$; -(L)-(CH_2)_p-C(O)NH_2$; -(L)-(CH_2)_p-C(O)NHOH$; -(L)-(CH_2)_p-C(O)NH-NH_2$; -(L)-(CH_2)_n-NHC(O)NH_2$; -(L)-(CH_2)_nOH$; -(L)-(CH_2)_nNH_2$; -(L)-(CH_2)_n-NH-C(NH_2)=NH$.

Preferably, in the compounds of formula (I), (I*), (A), (A*), (B), (B*), (A1) to (A26) and (A1*) to (A26*), $R^2$ represents $SO_3H$ Preferably, in the compounds of formula (I), (I*), (A), (A*), (B), (B*), (A1) to (A26) and (A1*) to (A26*):

$R^1$ is chosen among oxazole, isoxazole, thiazole, isothiazole, pyrazole, imidazole, imidazoline, oxadiazole, thiadiazole, triazole, tetrazole, unsubstituted or substituted by one or more $T^1$; and $R^3$ is chosen among hydrogen; $-(CH_2)_m-CN$; $-(CH_2)_m-C(O)OQ^1$; $-(CH_2)_m-C(O)NQ^1Q^2$; $-(CH_2)_m-C(O)NQ^1OQ^2$; $-(CH_2)_m-C(O)NQ^1-NQ^1Q^2$; $-(CH_2)_n-NQ^1C(O)NQ^1Q^2$; $-(CH_2)_nOQ^1$; $-(CH_2)_nNQ^1Q^2$; $-(CH_2)_n-NH-C(NHQ^3)=NQ^4$; $-(Y)-C_1-C_3$-alkyl; $-(Y)-CF_3$; $-(Y)-(CH_2)_p-CN$; $-(Y)-(CH_2)_p-C(O)OQ^1$; $-(Y)-(CH_2)_p-C(O)NQ^1Q^2$; $-(Y)-(CH_2)_p-C(O)NQ^1OQ^2$; $-(Y)-(CH_2)_p-C(O)NQ^1-NQ^1Q^2$; $-(Y)-(CH_2)_p-NQ^1C(O)Q^2$; $-(Y)-(CH_2)_p-NQ^1C(O)NQ^1Q^2$; $-(Y)-(CH_2)_pOQ^1$; $-(Y)-(CH_2)_pNQ^1Q^2$; $-(Y)-(CH_2)_n-NH-C(NHQ^3)=NQ^4$; or $C_1-C_3$-alkyl; $-CF_3$; $-(CH_2)_m$-(aromatic, totally or partially unsaturated, 4- to 6-membered heterocycle comprising at least one nitrogen atom) or $-(Y)-(CH_2)_m$-(aromatic, totally or partially unsaturated, 4- to 6-membered heterocycle comprising at least one nitrogen atom). Preferably, $R^3$ is chosen among hydrogen; $-(CH_2)_m-CN$; $-(CH_2)_m-C(O)OH$; $-(CH_2)_m-C(O)NH_2$; $-(CH_2)_m-C(O)NHOH$; $-(CH_2)_m-C(O)NH-NH_2$; $-(CH_2)_n-NHC(O)NH_2$; $-(CH_2)_nOH$; $-(CH_2)_nNH_2$; $-(CH_2)_n-NH-C(NH_2)=NH$; $-(Y)-C_1-C_3$-alkyl; $-(Y)-CF_3$; $-(Y)-(CH_2)_p-CN$; $-(Y)-(CH_2)_p-C(O)OH$; $-(Y)-(CH_2)_p-C(O)NH_2$; $-(Y)-(CH_2)_p-C(O)NHOH$; $-(Y)-(CH_2)_p-C(O)NH-NH_2$; $-(Y)-(CH_2)_p-NHC(O)H$; $-(Y)-(CH_2)_p-NHC(O)NH_2$; $-(Y)-(CH_2)_pOH$; $-(Y)-(CH_2)_pNH_2$; $-(Y)-(CH_2)_n-NH-C(NH_2)=NH$; or $C_1-C_3$-alkyl; $-CF_3$; $-(CH_2)_m$-(aromatic, totally or partially unsaturated, 4- to 6-membered heterocycle comprising at least one nitrogen atom) or $-(Y)-(CH_2)_m$-(aromatic, totally or partially unsaturated, 4- to 6-membered heterocycle comprising at least one nitrogen atom); and T and $T^1$, identical or different, represent F; —OCF3; —$(CH_2)_m$—CN; —$(CH_2)_m$—C(O)OQ$^1$; —$(CH_2)_m$—C(O)NQ$^1$Q$^2$; —$(CH_2)_m$—C(O)NQ$^1$OQ$^2$; —$(CH_2)_m$—C(O)NQ$^1$-NQ$^1$Q$^2$; —$(CH_2)_m$—NQ$^1$C(O)NQ$^1$Q$^2$; —$(CH_2)_m$OQ$^1$; —$(CH_2)_m$NQ$^1$Q$^2$; —$(CH_2)_m$—NH—C(NHQ$^3$)=NQ$^4$; -(L)-$(CH_2)_p$—CN; -(L)-$(CH_2)_p$—C(O)OQ$^1$; -(L)-$(CH_2)_p$—C(O)NQ$^1$Q$^2$; -(L)-$(CH_2)_p$—C(O)NQ$^1$OQ$^2$; -(L)-$(CH_2)_p$—C(O)NQ$^1$-NQ$^1$Q$^2$; -(L)-$(CH_2)_n$—NQ$^1$C(O)NQ$^1$Q$^2$; -(L)-$(CH_2)_n$OQ$^1$; -(L)-$(CH_2)_n$ NQ$^1$Q$^2$; -(L)-$(CH_2)_n$—NH—C(NHQ$^3$)=NQ$^4$; or T and $T^1$, identical or different, unsubstituted or substituted by one or more $T^3$, independently represent $C_1$-$C_3$-alkyl; $C_1$-$C_3$-fluoroalkyl; -(L)-$C_1$-$C_3$-alkyl; -(L)-$C_1$-$C_3$-fluoroalkyl; —$(CH_2)_m$-heterocycle; -(L)-$(CH_2)_p$-heterocycle. Preferably T and $T^1$, identical or different, represent F; —OCF3; —$(CH_2)_m$—CN; —$(CH_2)_m$—C(O)OH; —$(CH_2)_m$—C(O)NH$_2$; —$(CH_2)_m$—C(O)NHOH; —$(CH_2)_m$—C(O)NH—NH$_2$; —$(CH_2)_m$—NHC(O)NH$_2$; —$(CH_2)_m$OH; —$(CH_2)_m$NH$_2$; —$(CH_2)_m$—NH—C(NHQ$^3$)=NQ$^4$; -(L)-$(CH_2)_p$—CN; -(L)-$(CH_2)_p$—C(O)OH; -(L)-$(CH_2)_p$—C(O)NH$_2$; -(L)-$(CH_2)_p$—C(O)NHOH; -(L)-$(CH_2)_p$—C(O)NH—NH$_2$; -(L)-$(CH_2)_n$—NHC(O)NH$_2$; -(L)-$(CH_2)_n$OH; -(L)-$(CH_2)_n$NH$_2$; -(L)-$(CH_2)_n$—NH—C(NHQ$^3$)=NQ$^4$; or T and $T^1$, identical or different, unsubstituted or substituted by one or more $T^3$, independently represent $C_1$-$C_3$-alkyl; $C_1$-$C_3$-fluoroalkyl; -(L)-$C_1$-$C_3$-alkyl; -(L)-$C_1$-$C_3$-fluoroalkyl; —$(CH_2)_m$-heterocycle; -(L)-$(CH_2)_p$-heterocycle; and $T^2$ and $T^3$, identical or different, represent F; Me; CF3; —OCF$_3$; —$(CH_2)_m$—CN; —$(CH_2)_m$—C(O)OQ$^3$; —$(CH_2)_m$—C(O)NQ$^3$Q$^4$; —$(CH_2)_m$—C(O)NQ$^3$OQ$^4$; —$(CH_2)_m$—C(O)NQ$^3$-NQ$^3$Q$^4$; —$(CH_2)_m$—NQ$^3$C(O)NQ$^3$Q$^4$; —$(CH_2)_m$OQ$^3$; —$(CH_2)_m$NQ$^3$Q$^4$; —$(CH_2)_m$—NH—C(NHQ$^3$)=NQ$^4$; -(L)-Me; -(L)-$C_1$-$C_3$-fluoroalkyl; -(L)-$(CH_2)_p$—CN-(L)-$(CH_2)_p$—C(O)OQ$^3$; -(L)-$(CH_2)_p$—C(O)NQ$^3$Q$^4$; -(L)-$(CH_2)_p$—C(O)NQ$^3$OQ$^4$; -(L)-$(CH_2)_p$—C(O)NQ$^3$-NQ$^3$Q$^4$; -(L)-$(CH_2)_n$—NQ$^3$C(O)NQ$^3$Q$^4$; -(L)-$(CH_2)_n$OQ$^3$; -(L)-$(CH_2)_n$NQ$^3$Q$^4$; -(L)-$(CH_2)_n$—NH—C(NHQ$^3$)=NQ$^4$. Preferably, $T^2$ and $T^3$, identical or different, represent F; Me; CF3; —OCF$_3$; —$(CH_2)_m$—CN; —$(CH_2)_m$—C(O)OH; —$(CH_2)_m$—C(O)NH$_2$; —$(CH_2)_m$—C(O)NHOH; —$(CH_2)_m$—C(O)NH—NH$_2$; —$(CH_2)_m$—NHC(O)NH$_2$; —$(CH_2)_m$OH; —$(CH_2)_m$NH$_2$; —$(CH_2)_m$—NH—C(NH$_2$)=NH; -(L)-Me; -(L)-$C_1$-$C_3$-fluoroalkyl; -(L)-$(CH_2)_p$—CN-(L)-$(CH_2)_p$—C(O)OH; -(L)-$(CH_2)_p$—C(O)NH$_2$; -(L)-$(CH_2)_p$—C(O)NHOH; -(L)-$(CH_2)_p$—C(O)NH—NH$_2$; -(L)-$(CH_2)_n$—NHC(O)NH$_2$; -(L)-$(CH_2)_n$OH; -(L)-$(CH_2)_n$NH$_2$; -(L)-$(CH_2)_n$—NH—C(NH$_2$)=NH; and preferably $R^2$ represents SO$_3$H or CF$_2$COOH, preferably SO$_3$H.

Preferably, in the compounds of formula (I), (I*), (A), (A*) (A1) to (A26), (A1*) to (A26*), (B) or (B*) of the invention $R^1$ represents a 5-membered heterocycle comprising at least two nitrogen atom and optionally one other heteroatom, especially chosen among O, N, NR$_3$, S, SO, SO$_2$, preferably O.

W is a 5-membered aromatic heterocycle comprising at least one nitrogen atom and optionally one other heteroatom, especially chosen among O, N, NR$_3$, S, SO, SO$_2$, preferably S.

Preferably, in the compounds of formula (I), (I*), (A), (A*) (A1) to (A26), (A1*) to (A26*), of the invention $R^1$ represents a 5-membered heterocycle comprising at least two nitrogen atom and optionally one other heteroatom, especially chosen among O, N, NR$_3$, S, SO, SO$_2$, preferably O and W is a 5-membered aromatic heterocycle comprising at least one nitrogen atom and optionally one other heteroatom, especially chosen among O, N, NR$_3$, S, SO, SO$_2$, preferably S.

Preferably, in the compounds of formula (I), (I*), (A), (A*) (A1) to (A26), (A1*) to (A26*), of the invention $R^1$ represents a 5-membered heterocycle comprising at least two nitrogen atom and optionally one other heteroatom, especially chosen among O, N, NR$_3$, S, SO, SO$_2$, preferably O and W is a 5-membered aromatic heterocycle comprising at least one nitrogen atom and optionally one other heteroatom, especially chosen among O, N, NR$_3$, S, SO, SO$_2$, preferably S and $R^2$ represents SO$_3$H.

The term "alkyl", as used herein, refers to an aliphatic-hydrocarbon group which may be straight or branched, having 1 to 3 carbon atoms in the chain unless specified otherwise. Preferred alkyl groups have 1 or 2 carbon atoms in the chain. Specific examples of alkyl groups include, but are not limited to, methyl, ethyl, n-propyl, iso propyl. Preferably, the alkyl group is methyl or ethyl.

The term "fluoroalkyl", as used herein, refers to an alkyl group substituted with at least one fluorine atom. The term "alkyl" is as defined above. Specific examples of fluoroalkyl groups include but are not limited to trifluoromethyl, difluoromethyl, fluoromethyl.

The term "cycloalkyl" refers to a saturated monocyclic or bicyclic non-aromatic hydrocarbon ring of 3 to 6 carbon atoms, preferably 3 to 4 carbon atoms, which can comprise one or more unsaturation. Specific examples of monocyclic cycloalkyl groups include cyclopropyl, cyclobutyl, cyclopentyl, cyclohexyl. Preferably, the cycloalkyl group is cyclopropyl or cyclobutyl.

The term "fluorocycloalkyl" refers to a cycloalkyl group substituted with at least one fluorine atom. The term "cycloalkyl" is as defined above. Specific examples of fluorocycloalkyl groups include fluorocyclopropyl, difluorocyclopropyl, fluorocyclobutyl, difluorocyclobutyl.

The term "heterocycle", as used herein and without contrary definition specifically mentioned, either alone or in combination with another radical, refers to a monocyclic saturated, partially or totally unsaturated or aromatic hydrocarbon radical, preferably to a 4- to 10-membered hydrocarbon radical, comprising at least one heteroatom, such as N, O, S, S(O) or S(O)$_2$. Preferably, the heterocycle is a monocyclic saturated, partially or totally unsaturated or aromatic hydrocarbon radical, preferably a 4- to 6-membered hydrocarbon radical, comprising at least one nitrogen atom and at least one further heteroatom, such as N, O, S, S(O) or S(O)$_2$. The carbon atoms of the heterocycle can also be oxidized to form a C(O) group. Suitable heterocycles are also disclosed in the Handbook of Chemistry and Physics, 76$^{th}$ Edition, CRC Press, Inc., 1995-1996, pages 2-25 to 2-26. Exemplary heterocycle groups include, but are not limited to, azetidinyl, oxetanyl, oxazolyl, oxazolidinyl, oxadiazolyl, pyrrolyl, pyrrolidinyl, pyridyl, tetrahydropyridinyl, piperidinyl, morpholinyl, pyrazolyl, pyrimidinyl, pyrazinyl, tetrazolyl, imidazolyl, thienyl, thiazolyl, furanyl, thiadiazolyl, isothiazolyl, triazolyl, tetrazolyl, pyrazolyl, isoxazolyl, 2-pyrrolidinonyl, imidazol-2,4-dione, 1,2,4-oxadiazol-5-one, 1,5-dihydropyrrolyl-2-one, pyrazinone, pyridazinone, pyridone, pyrimidone, dioxanyl, pyrrolidinyl, imidazolidinyl, pyranyl, tetrahydrofuranyl, dioxolanyl, tetrahydropyranyl. Preferably, in the compounds according to the invention, the heterocycle is linked to the structure of the compounds by a carbon atom of the heterocycle (also said carbon-linked heteroatom).

Moreover some compounds according to this invention may contain a basic amino group and thus may form an inner zwitterionic salt (or zwitterion) with the acidic group $(R^2)$—$OSO_3H$, —$OCFHCO_2H$ or —$OCF_2CO_2H$ and such inner zwitterionic salts are also included in this invention.

The expression "optionally substituted" means "non-substituted or substituted by chemical groups that are further defined" or "unsubstituted or substituted chemical groups that are further defined".

The term "racemate" is employed herein to refer to an equal amount of two specific enantiomers.

The term "enantiomer" is employed herein to refer to one of the two specific stereoisomers which is a non-superimposable mirror image with one other but is related to one other by reflection.

The compounds according to the invention may include one or more asymmetric carbon atoms and may thus exist in the form of optical isomers as well as in the form of racemic or non-racemic mixtures thereof. The compounds according to the invention can be used as a single isomer or as a mixture of stereochemical isomeric forms. Diastereoisomers, i.e., non-superimposable stereochemical isomers can be separated by conventional means such as chromatography, distillation, crystallization or sublimation. The optical isomers (enantiomers) can be obtained by using optically active starting materials, by resolution of the racemic mixtures according to conventional processes, for example by formation of diastereoisomeric salts by treatment with an optically active acid or base or by using chiral chromatography column.

As used herein, the expression "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention can be synthesized from the parent compound which comprises a basic or an acidic moiety, by conventional chemical methods. Furthermore, the expression "pharmaceutically acceptable salt" refers to relatively non-toxic, inorganic and organic acid or base addition salts of the compounds of the present invention. These salts can be prepared in situ during the final isolation and purification of the compounds. In particular, the acid addition salts can be prepared by separately reacting the purified compound in its purified form with an organic or inorganic acid and by isolating the salt thus formed. Among the examples of acid addition salts are the hydrobromide, hydrochloride, hydroiodide, sulfamate, sulfate, bisulfate, phosphate, nitrate, acetate, propionate, succinate, oxalate, valerate, oleate, palmitate, stearate, laurate, borate, benzoate, lactate, tosylate, citrate, maleate, fumarate, tartrate, naphthylate, mesylate, glucoheptanate, glucoronate, glutamate, lactobionate, malonate, salicylate, methylenebis-b-hydroxynaphthoate, gentisic acid, isethionate, di-p-toluoyltartrate, ethanesulfonate, benzenesulfonate, cyclohexyl sulfamate, quinateslaurylsulfonate salts, and the like. Examples of base addition salts include ammonium salts such as tromethamine, meglumine, epolamine, etc, metal salts such as sodium, lithium, potassium, calcium, zinc or magnesium salts with organic bases such as dicyclohexylamine salts, N-methyl-D-glucamine. Lists of suitable salts may be found in Remington's Pharmaceutical Sciences, 17$^{th}$ ed., Mack Publishing Company, Easton, Pa., 1985, p. 1418, P. H. Stahl, C. G. Wermuth, Handbook of Pharmaceutical salts—Properties, Selection and Use, Wiley-VCH, 2002 and S. M. Berge et al. "Pharmaceutical Salts" J. Pharm. Sci, 66: p. 1-19 (1977).

Compounds according to the invention also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described above and are not limited to $^{2}H$, $^{3}H$, $^{11}C$, $^{13}C$, $^{14}C$, $^{18}F$, $^{19}F$, $^{13}N$, $^{15}N$, $^{33}S$, $^{34}S$, $^{35}S$, $^{36}S$, $^{17}O$ or $^{18}O$. Isotopically-labeled compounds are useful in drug and/or substrate tissue distribution studies. Substitution with heavier isotopes such as deuterium ($^{2}H$) affords greater metabolic stability (for example increased in vivo half-life or reduced dosage requirements). Isotopically-labeled compounds are prepared by any suitable method or by processes using an appropriate isotopically-labeled reagent in replacement of the non-labeled reagent otherwise employed.

The invention provides compounds having antibacterial properties and/or compounds acting as β-lactamase inhibitors.

The invention also provides a process for the preparation of a compound according to the invention. In particular the invention provides a process for the preparation of compound selected from compounds of formulae (I), (A), (B), (A1) to (A26), (I*), (A*), (B*), (A1*) to (A26*) according to the invention.

The invention also provides the use of the compounds according to the invention in the control of bacteria. The compound according to the invention is then usually used in combination with at least one pharmaceutically acceptable excipient.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also provides a composition, preferably a pharmaceutical composition, comprising at least one compound according to the invention in mixture with a pharmaceutically acceptable excipient. The composition according to the invention may thus comprise at least one compound selected from compounds of formulae (I), (A), (B), (A1) to (A26), (I*), (A*), (B*), (A1*) to (A26*) in mixture with a pharmaceutically acceptable excipient.

The term "pharmaceutically acceptable carrier" or "pharmaceutically acceptable excipient" is employed for any excipient, solvent, dispersion medium, absorption retardant, diluent or adjuvant etc., such as preserving or antioxidant agents, fillers, binders, disintegrating agents, wetting agents, emulsifying agents, suspending agents, solvents, dispersion media, coatings, antibacterial agents, isotonic and absorption delaying agents and the like, that does not produce a secondary reaction, for example an allergic reaction, in humans or animals. Typical, non-limiting examples of excipients include mannitol, lactose, magnesium stearate, sodium saccharide, talcum, cellulose, sodium croscarmellose, glucose, gelatin, starch, lactose, dicalcium phosphate, sucrose, kaolin, magnesium carbonate, wetting agents, emulsifying agents, solubilizing agents, sterile water, saline, pH buffers, non-ionic surfactants, lubricants, stabilizing agents, binding agents and edible oils such as peanut oil, sesame oils and the like. In addition, various excipients commonly used in the art may be included. Pharmaceutically acceptable carriers or excipients are well known to a person skilled in the art, and include those described in Remington's Pharmaceutical Sciences (Mack Publishing Company, Easton, USA, 1985), Merck Index (Merck & Company, Rahway, N.J.), Gilman et al (Eds. The pharmacological basis of therapeutics, 8$^{th}$ Ed., Pergamon press, 1990). Except insofar as any conventional media or adjuvant is incompatible with the active ingredient according to the invention, its use in the therapeutic compositions is contemplated.

The expression "antibacterial agent" as used herein, refers to any substance, compound or their combination capable of inhibiting, reducing or preventing growth of bacteria, inhibiting or reducing ability of bacteria to produce infection in a subject, or inhibiting or reducing ability of bacteria to multiply or remain infective in the environment, or decreasing infectivity or virulence of bacteria.

The antibacterial agent can be selected among the following families: aminoglycosides, beta-lactams, glycylcyclines, tetracyclines, quinolones, fluoroquinolones, glycopeptides, lipopeptides, macrolides, ketolides, lincosamides, streptogramins, oxazolidinones and polymyxins alone or in mixture. Preferably, the further antibacterial agent is selected among the beta-lactam families, and more preferably among penicillin, cephalosporins, penems, carbapenems and monobactam, alone or in mixture.

Among the penicillin the antibacterial agent is preferably selected in the group consisting of amoxicillin, ampicillin, azlocillin, mezocillin, apalcillin, hetacillin, bacampicillin, carbenicillin, sulbenicillin, temocillin, ticarcillin, piperacillin, mecillinam, pivmecillinam, methicillin, ciclacillin, talampacillin, aspoxicillin, oxacillin, cloxacillin, dicloxacillin, flucloxacillin, nafcillin, and pivampicillin, alone or in mixture.

Among the cephalosporin, the antibacterial agent is preferably selected in the group consisting of cefatriazine, cefazolin, cefoxitin, cephalexin, cephradine, ceftizoxime, cephacetrile, cefbuperazone, cefprozil, ceftobiprole, ceftobiprole medocaril, ceftaroline, ceftaroline fosaminyl, cefalonium, cefminox, ceforanide, cefotetan, ceftibuten, cefcapene pivoxil, cefditoren pivoxil, cefdaloxime cefroxadine, ceftolozane and S-649266, cephalothin, cephaloridine, cefaclor, cefadroxil, cefamandole, cefazolin, cephalexin, cephradine, ceftizoxime, cephacetrile, cefotiam, cefotaxime, cefsulodin, cefoperazone, cefmenoxime, cefmetazole, cephaloglycin, cefonicid, cefodizime, cefpirome, ceftazidime, ceftriaxone, cefpiramide, cefbuperazone, cefozopran, cefepime, cefoselis, cefluprenam, cefuzonam, cefpimizole, cefclidine, cefixime, ceftibuten, cefdinir, cefpodoxime axetil, cefpodoxime proxetil, cefteram pivoxil, cefetamet pivoxil, cefcapene pivoxil, cefditoren pivoxil, cefuroxime, cefuroxime axetil, loracarbef, and latamoxef, alone or in mixture.

Among the carbapenem, the antibacterial agent is preferably selected in the group consisting of imipenem, doripenem, meropenem, biapenem, ertapenem and panipenem, alone or in mixture.

Among the monobactam, the antibacterial agent is preferably selected in the group consisting of aztreonam, tigemonam, carumonam, BAL30072 and nocardicin A, alone or in mixture.

The present invention also provides a kit comprising:
a pharmaceutical composition according to the invention, and
at least one other composition comprising one or more antibacterial agents, preferably at least one of these antibacterial agents is a beta-lactam.

The two compositions can each be prepared separately with one specific pharmaceutically acceptable carrier, and can then be mixed, especially extemporaneously.

The present invention also refers to a compound selected within the compounds of formulae (I), (A), (B), (A1) to (A26), (I*), (A*), (B*) and (A1*) to (A26*) according to the invention for its use as a medicine.

The present invention also refers to a compound selected within the compounds of formulae (I), (A), (B), (A1) to (A26), (I*), (A*), (B*) and (A1*) to (A26*) according to the invention for its use for the preparation of a medicine.

The present invention also refers to a compound selected within the compounds of formulae (I), (A), (B), (A1) to (A26), (I*), (A*), (B*) and (A1*) to (A26*) according to the invention for its use as an antibacterial agent.

The present invention also refers to the use of a compound selected within the compounds of formulae (I), (A), (B), (A1) to (A26), (I*), (A*), (B*) and (A1*) to (A26*) according to the invention or to the use of a pharmaceutical composition according to the invention for the preparation of an antibacterial agent comprising medicine.

The present invention also refers to the use of a compound selected within the compounds of formulae (I), (A), (B), (A1) to (A26), (I*), (A*), (B*) and (A1*) to (A26*) according to the invention or to the use of a pharmaceutical composition according to the invention for the preparation of a beta-lactamase inhibitor comprising medicine.

The present invention also refers to the use of a compound selected within the compounds of formulae (I), (A), (B), (A1) to (A26), (I*), (A*), (B*) and (A1*) to (A26*) according to the invention or to the use of a pharmaceutical composition according to the invention for the preparation of a medicine comprising an antibacterial agent and a beta-lactamase inhibitor.

The present invention also refers to the use of a compound selected within the compounds of formulae (I), (A), (B), (A1) to (A26), (I*), (A*), (B*) and (A1*) to (A26*) according to the invention or to the use of a pharmaceutical composition according to the invention or to the use of a kit according to the invention for the treatment or for the prevention of at least one bacterial infection.

The present invention also refers to the use of a compound selected within the compounds of formulae (I), (A), (B), (A1) to (A26), (I*), (A*), (B*) and (A1*) to (A26*) according to the invention or to the use of a pharmaceutical composition according to the invention or to the use of a kit according to the invention for the preparation of a medicine useful in the treatment or in the prevention of at least one bacterial infection.

The terms "prevention", "prevent" and "preventing" as used herein are intended to mean the administration of a compound or composition according to the invention in order to prevent infection by bacteria or to prevent occurrence of related infection and/or diseases. The terms "prevention", "prevent" and "preventing" also encompass the administration of a compound or composition according to the present invention in order preventing at least one bacterial infection, by administration to a patient susceptible to be infected, or otherwise at a risk of being infected by this bacteria.

The terms "treatment", "treat" and "treating" as used herein are intended to mean in particular the administration of a treatment comprising a compound or composition according to the invention to a patient suffering from an infection. The terms "treatment", "treat" and "treating" as used herein, also refer to administering a compound or composition according to the invention, optionally in combination with one or more further antibacterial agent, in order:
to reduce or to eliminate either bacterial infection or one or more symptoms associated with a bacterial infection, or
to retard the progression of a bacterial infection or of one or more symptoms associated with a bacterial infection, or
to reduce the severity of a bacterial infection or of one or more symptoms associated with a bacterial infection, or to suppress the clinical manifestation of a bacterial infection, or to suppress the manifestation of adverse symptoms caused by a bacterial infection.

The expression "infection" or "bacterial infection" as used herein, include the presence of bacteria, in or on a subject, which, if its growth were inhibited, would result in a benefit to the subject. As such, the term "infection" or "bacterial infection" in addition to referring to the presence of bacteria also refer to normal flora, which is not desirable. The term "infection" includes infection caused by bacteria. Examples of such bacterial infections are urinary tract infection (UTI), kidney infections (pyelonephritis), gynecological and obstetrical infections, respiratory tract infection (RTI), acute exacerbation of chronic bronchitis (AECB), Community-acquired pneumonia (CAP), hospital-acquired pneumonia (HAP), ventilator associated pneumonia (VAP), intra-abdominal pneumonia (IAI), acute otitis media, acute sinusitis, sepsis, catheter-related sepsis, chancroid, chlamydia, skin infections, bacteremia.

The term "growth" as used herein, refers to the growth of one or more microorganisms and includes reproduction or population expansion of a microorganism, such as bacteria. The term also includes maintenance of on-going metabolic processes of a microorganism, including processes that keep the microorganism alive.

According to the invention, bacteria are chosen amongst gram-positive bacteria or gram-negative bacteria, preferably gram-negative bacteria. According to the invention, bacteria can be also chosen among bacteria producing "beta-lactamase" or "β-lactamase". These bacteria are well known by the person skilled in the art. The term "beta-lactamase" or "β-lactamase" as used herein, refers to any enzyme or protein or any other substance that is able to break down a beta-lactam ring. The term "beta-lactamase" or "β-lactamase" includes enzymes that are produced by bacteria and that have the ability to hydrolyze, either partially or completely, the beta-lactam ring present in a compound such as an antibacterial agent.

Among the gram-positive bacteria, the bacteria according to the invention is preferably chosen among *Staphylococcus, Streptococcus, Staphylococcus* species (including *Staphylococcus aureus, Staphylococcus epidermidis*), *Streptococcus* species (including *Streptococcus pneumonia, Streptococcus agalactiae*), *Enterococcus* species (including *Enterococcus faecalis* and *Enterococcus faecium*).

Among the gram-negative bacteria, the bacteria according to the invention is preferably chosen among *Acinetobacter* species (including *Acinetobacter baumannii*), *Citrobacter* species, *Escherichia* species (including *Escherichia coli*), *Haemophilus* influenza, *Morganella morganii, Klebsiella* species (including *Klebsiella pneumonia*), *Enterobacter* species (including *Enterobacter cloacae*), *Neisseria gonorrhoeae, Burkholderia* species (including *Burkholderia cepacia*), (*Proteus* species (including *Proteus mirabilis*), *Serratia* species (including *Serratia marcescens*), *Pseudomonas aeruginosa*.

The invention thus preferably refers to a compound selected within the compounds of formulae (I), (A), (B), (A1) to (A26), (I*), (A*), (B*) and (A1*) to (A26*) according to the invention or to a pharmaceutical composition according to the invention or to a kit according to the invention for its use for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to the use of a compound selected within the compounds of formulae (I), (A), (B), (A1) to (A26), (I*), (A*), (B*) and (A1*) to (A26*) according to the invention or to a pharmaceutical composition according to the invention for the preparation of a medicine for the treatment or for the prevention of a bacterial infection, preferably caused by bacteria producing one or more beta-lactamases. Preferably, the bacteria are chosen amongst gram-positive bacteria or gram-negative bacteria, more preferably gram-negative bacteria.

The present invention also refers to a kit according to the invention, for its simultaneous, separated or sequential administration to a patient in need thereof in the treatment or in the prevention of bacterial infections, preferably caused by bacteria producing one or more beta-lactamases. Preferably, the bacteria are chosen amongst gram-positive bacteria or gram-negative bacteria, more preferably gram-negative bacteria.

The present invention also refers to a compound selected within the compounds of formulae (I), (A), (B), (A1) to (A26), (I*), (A*), (B*) and (A1*) to (A26*) according to the invention for its use in combination with one or more further antibacterial agents, preferably at least one of the further antibacterial agents being a beta lactam compound, for the treatment or for the prevention of bacterial infections, preferably caused by bacteria producing one or more beta-lactamases. Preferably, the bacteria are chosen amongst gram-positive bacteria or gram-negative bacteria, more preferably gram-negative bacteria, and wherein a compound selected within the compounds of formulae (I), (A), (B), (A1) to (A26), (I*), (A*), (B*) and (A1*) to (A26*) according to the invention and the further antibacterial agent are administered simultaneously, separately or sequentially.

The present invention also refers to the use of a compound selected within the compounds of formulae (I), (A), (B), (A1) to (A26), (I*), (A*), (B*) and (A1*) to (A26*) according to the invention or of a pharmaceutical composition according to the invention or of a kit according to the invention for the prevention or for the treatment of bacterial infections, preferably of a bacterial infection, preferably caused by bacteria producing one or more beta-lactamases. Preferably, the bacteria are chosen amongst gram-positive bacteria or gram-negative bacteria, more preferably gram-negative bacteria.

The present invention also relates to a method for the treatment or prevention of bacterial infections, preferably caused by bacteria producing one or more beta-lactamases comprising the administration of a therapeutically effective amount of a compound selected within the compounds of formulae (I), (A), (B), (A1) to (A26), (I*), (A*), (B*) and (A1*) to (A26*) according to the invention, or of a pharmaceutical composition according to the invention or of a kit according to the invention to a patient in need thereof. Preferably, the bacteria are chosen amongst gram-positive bacteria or gram-negative bacteria, more preferably gram-negative bacteria.

The term "patient" means a person or an animal at risk of being infected by bacteria or, a person or an animal being infected by bacteria, preferably by gram-positive and by gram-negative bacteria, more preferably by gram-negative bacteria. As used herein, the term "patient" refers to a warm-blooded person or animal such as a mammal, preferably a human or a human child, who is afflicted with, or has the potential to be afflicted with one or more infections and conditions described herein. The identification of those subjects who are in need of treatment of herein-described diseases and conditions is well within the ability and knowledge of one skilled in the art. A veterinarian or a physician skilled in the art can readily identify, by the use of clinical tests, physical examination, medical or family history or biological and diagnostic tests, those subjects who are in need of such a treatment.

The expression "therapeutically effective amount" or "pharmaceutically effective amount" as used herein, refer to an amount of a compound according to the invention, which when administered to a patient in need thereof, is sufficient to effect treatment for disease-states, conditions, or disorders for which the compound has utility. Such an amount would be sufficient to elicit the biological or medical response of a tissue system, or patient that is sought by a researcher or a clinician. The amount of a compound according to the invention which constitutes a "therapeutically effective amount" will vary, notably depending on the compound itself and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient. Such a "therapeutically effective amount" can be determined by one of ordinary skilled in the art having regard to its own knowledge, and this disclosure. Preferably, the compound according to the invention is administered in an amount comprised between 0.1 to 30 g per day.

The compound according to the invention may be provided in an aqueous physiological buffer solution for parenteral administration. The compound of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described herein. The compound provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The pharmaceutical composition may be conveniently administered in unit dosage form and may be prepared by any method well-known in the pharmaceutical art, for example, as described in *Remington: The Science and Practice of Pharmacy*, 20$^{th}$ ed.; Gennaro, A. R., Ed.; Lippincott Williams & Wilkins: Philadelphia, Pa., 2000.

Preferred formulations include pharmaceutical compositions wherein a compound according to the present invention is formulated for oral or parenteral administration.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate or talc in any combination.

Liquid preparations for parenteral administration include sterile aqueous or non-aqueous solutions, suspensions and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compound. Intravenous vehicles can include fluid and nutrient replenishers, electrolyte replenishers, such as those based on Ringer's dextrose, and the like. Other potentially useful parenteral delivery systems for the active compound include ethylene-vinyl acetate copolymer particles, osmotic pumps, implantable infusion systems and liposomes.

Alternative modes of administration include formulations for inhalation, which include such means as dry powder, aerosol, or drops. They may be aqueous solutions comprising, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations.

Formulations suitable for transdermal administration can be presented as discrete patches and can be lipophilic emulsions or buffered, aqueous solutions, dissolved and/or dispersed in a polymer or an adhesive.

The present invention also relates to the following intermediate compounds, especially for the preparation of compounds of formula (I), (I*), (A), (A*), (A1) to (A26) and (A1*) to (A26*)

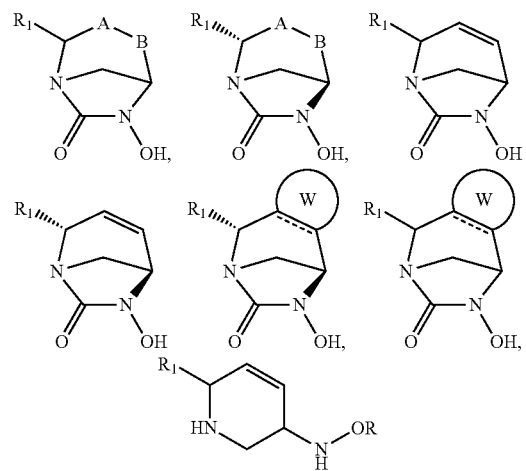

Wherein R[1], A, B and W have the definition given above and R is a protective group, for example chosen among allyl, benzyl, tertbutyldimethylsilyl (TBDMS).

All the preferencies of R1, A and B also applies for the above intermediate compounds.

The invention is further illustrated but not restricted by the description of the following examples.

EXAMPLES

Abbreviations or symbols used herein include:
ACHN: 1,1'-azobis(cyclohexanecarbonitrile)
ACN: acetonitrile
AcCl: acetyl chloride
AcOH: acetic acid
Bn: benzyl
BOC: tert-butoxycarbonyl
Boc$_2$O: tert-butoxycarbonyl anhydride
bs: broad singlet
CFU: colony-forming units
CLSI: clinical laboratory standards institute
d: doublet
DBU: 1,8-diazabicyclo[5.4.0]undec-7-ene
DCM: dichloromethane
dd: doublet of doublet
ddd: doublet of doublet of doublet
ddt: doublet of doublet of triplet
dt: doublet of triplet
DTA: di-tert-butylazodicarboxylate
DEAD: diethyl azodicarboxylate
DIAD: diisopropyl azodicarboxylate
DIPEA: diisopropylethylamine
DMF: N,N-dimethylformamide
DMAP: 4-dimethylaminopyridine
DMSO: dimethylsulfoxide
EtOAc: ethyl acetate
Et$_2$O: diethyl ether
h: hours
HATU: 1-[Bis(dimethylamino)methylene]-1H-1,2,3-triazolo[4,5-b]pyridinium 3-oxid hexafluorophosphate
IC$_{50}$: concentration of inhibitor responsible for 50% of inhibition
KOAc: potassium acetate
m: massif
min: minutes
MeOH: methanol
MIC: minimum inhibitory concentration
MS: mass spectrometry
MsCl: methanesulfonyl chloride
MTBE: methyl tert-butyl ether
NBS: N-bromosuccinimide
NMR: nuclear magnetic resonance spectroscopy
Nos: nosyl, nitrobenzenesulfonyl
Pd(dppf)Cl$_2$: [1,1'-bis(diphenylphosphino)ferrocene]dichloropalladium
Pd(PPh$_3$)$_4$: tetrakis(triphenylphosphine)palladium(0)
PEPPSI: [1,3-bis(2,6-diisopropylphenyl)imidazol-2-ylidene](3-chloropyridyl)palladium(II) dichloride
PG1: protective group 1
PG2: protective group 2
PhSH: thiophenol
PivCl: pivaloyl chloride
PPh$_3$: triphenylphosphine
Ppm: parts per million
q: quartet
dq: doublet of quartet
rt: room temperature
s: singlet
SEMCl: 2-(trimethylsilyl)ethoxymethyl chloride
t: triplet
td: triplet of doublet
TEA: trimethylamine
TFA: trifluoroacetic acid
THF: tetrahydrofuran
TLC: thin layer chromatography
TMSCN: trimethylsilyl cyanide
TMSI: iodotrimethylsilane The compounds of the present invention of formula (I) can be prepared by the following reaction Schemes 1-9 where A-B represents a ring W or CH=CH double bond.

Scheme 1

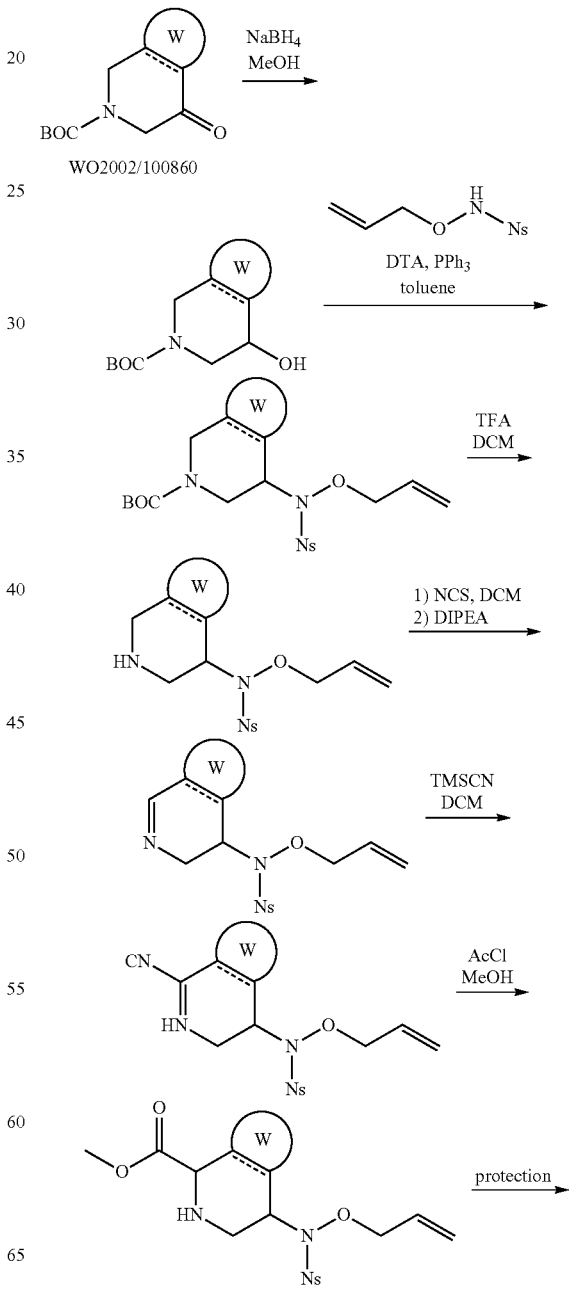

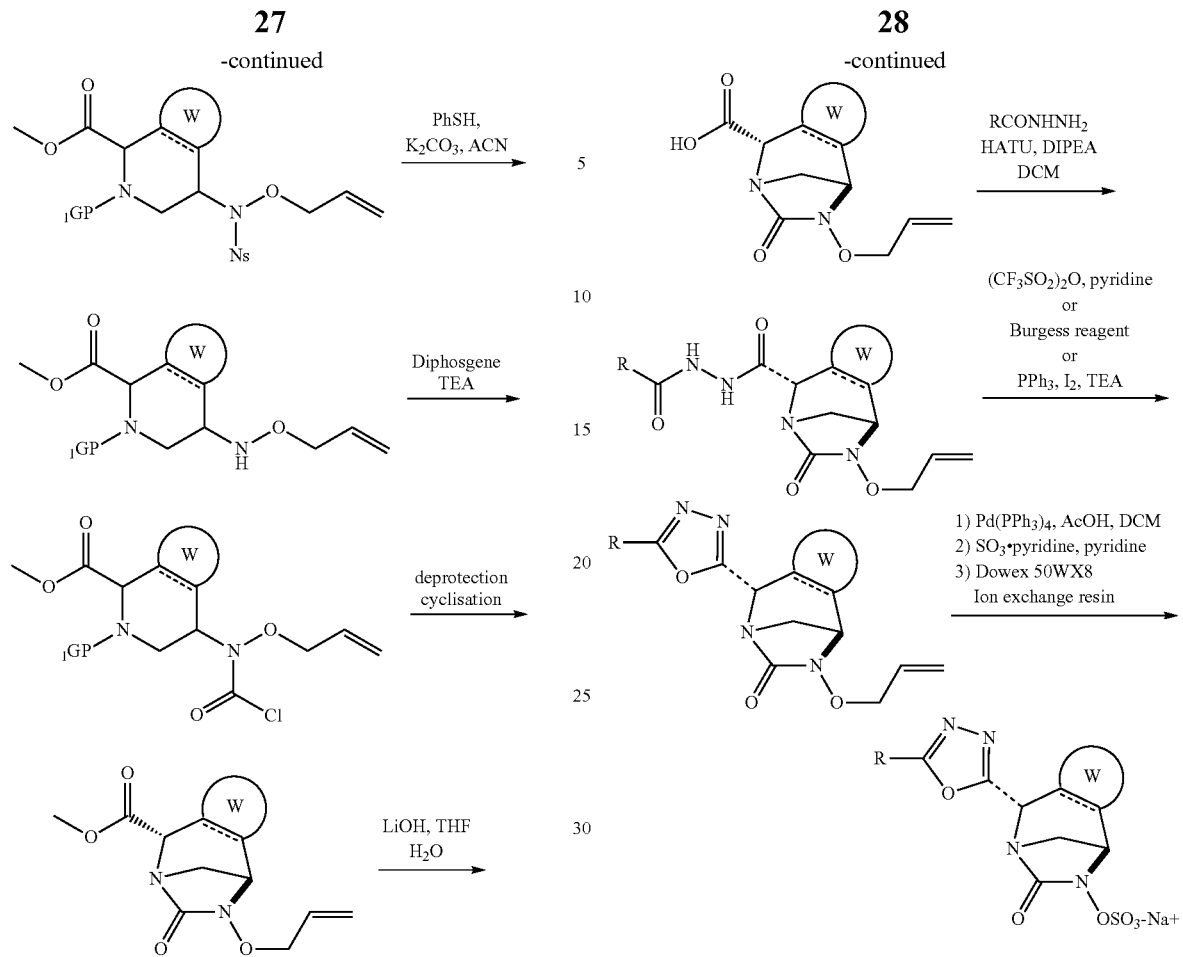
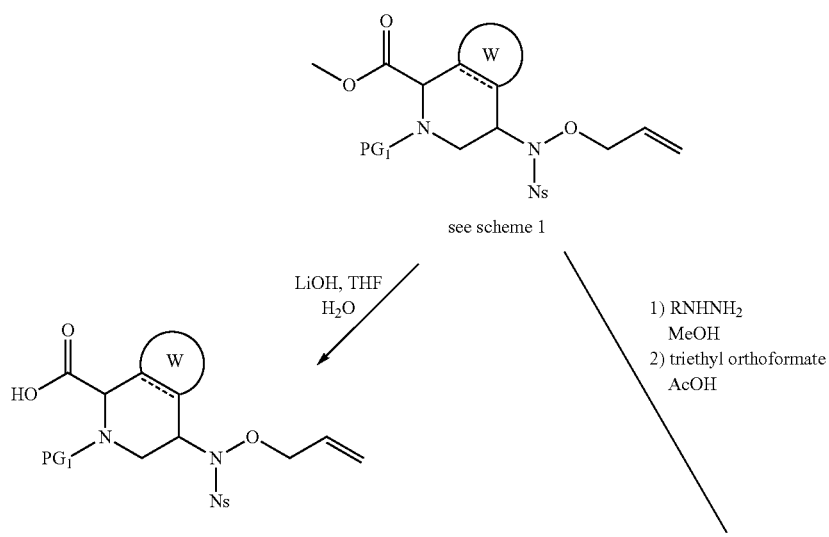
Scheme 2

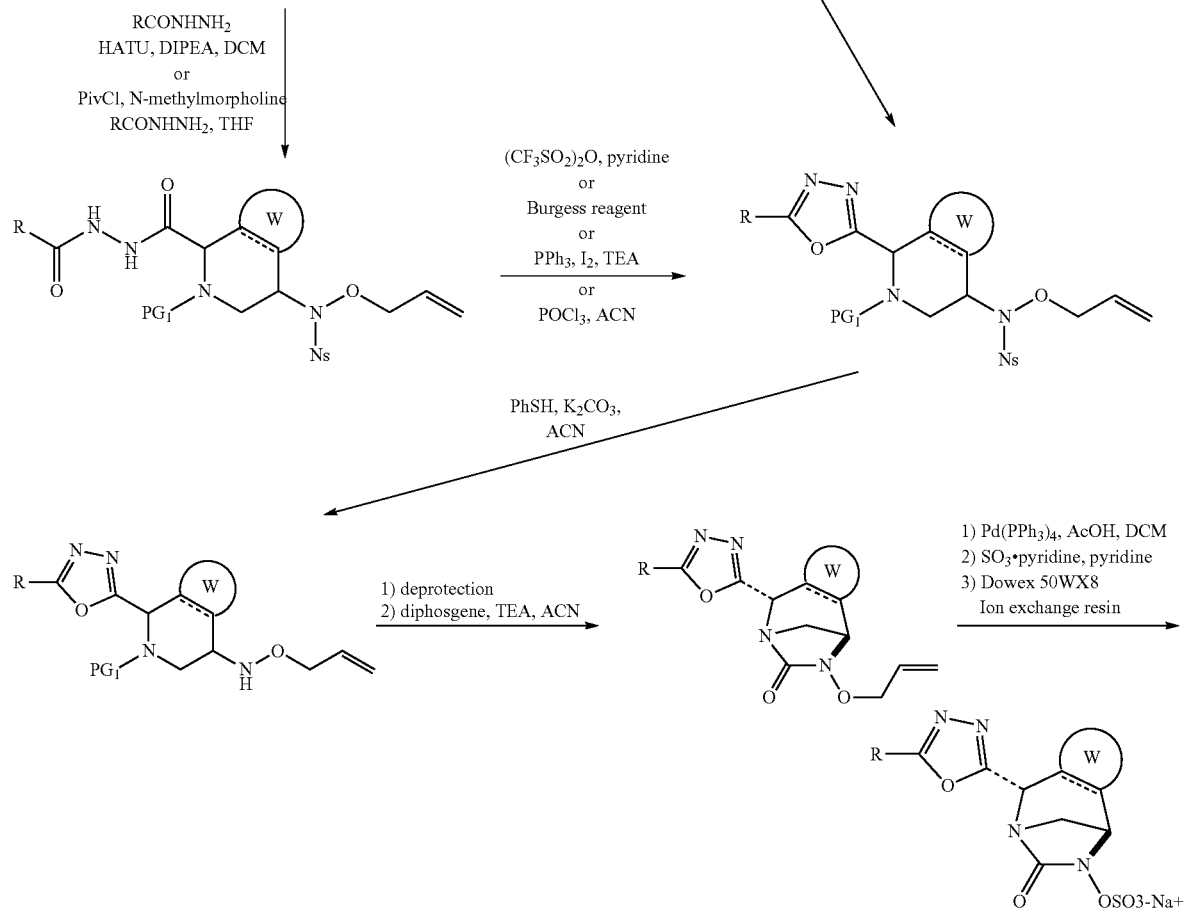
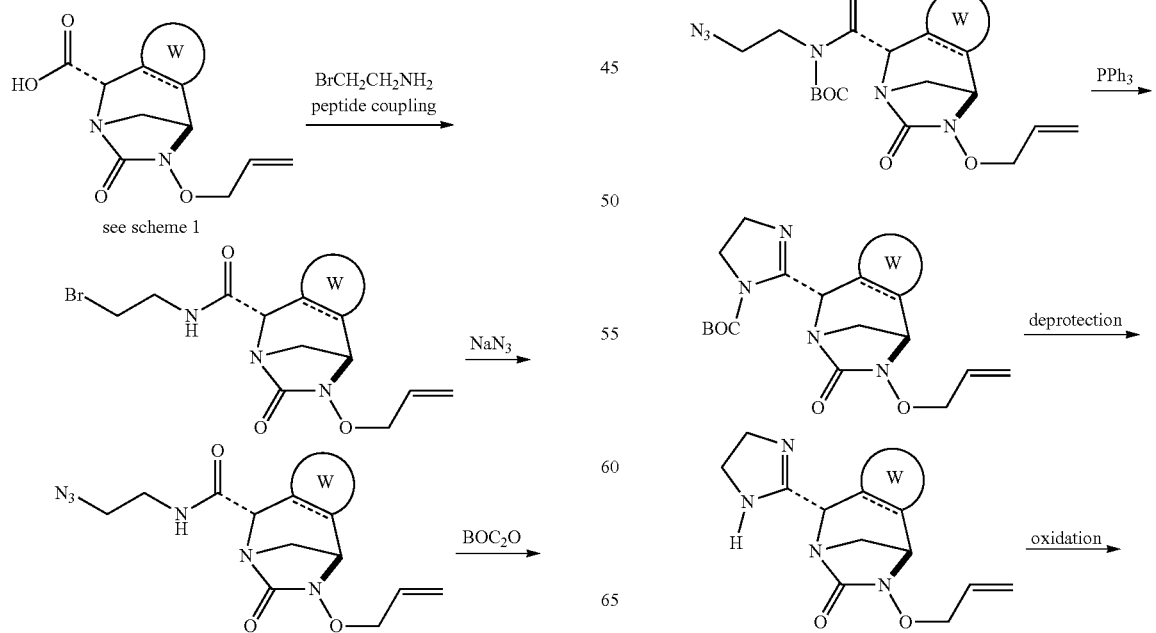
Scheme 3

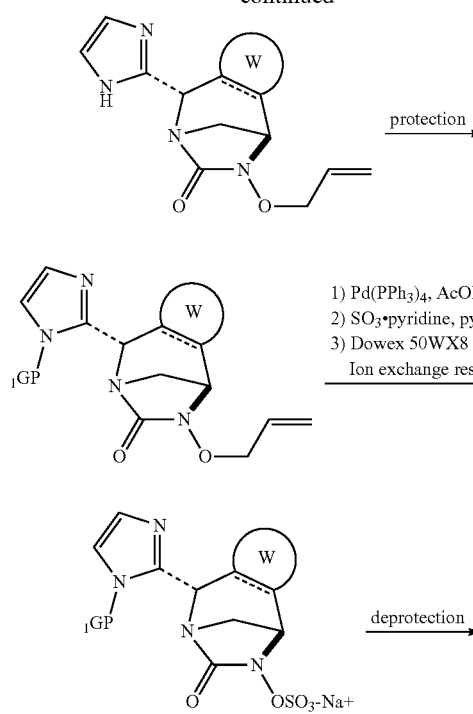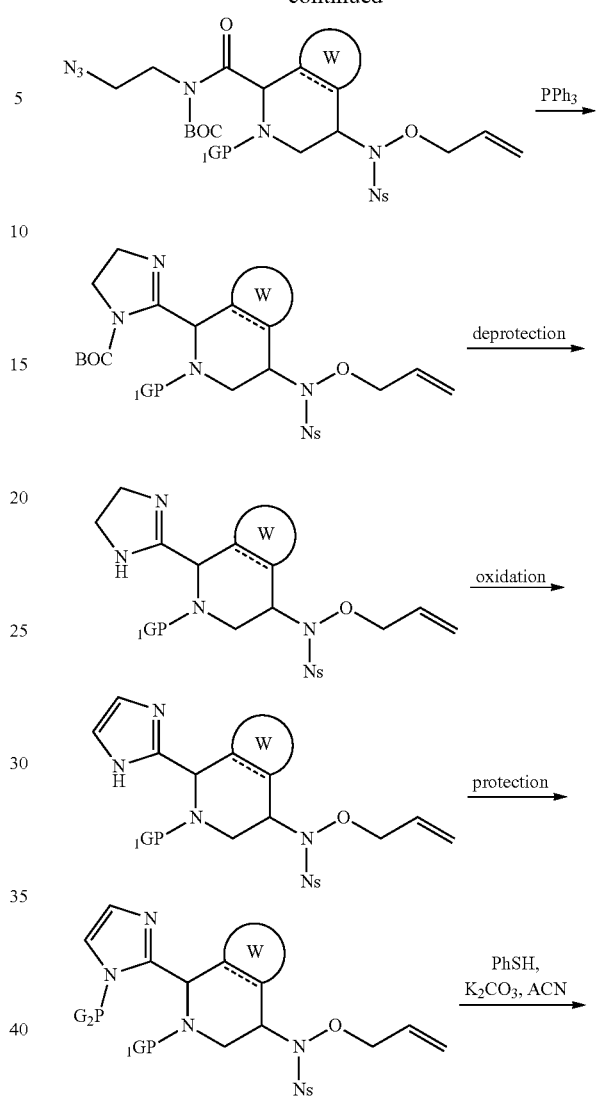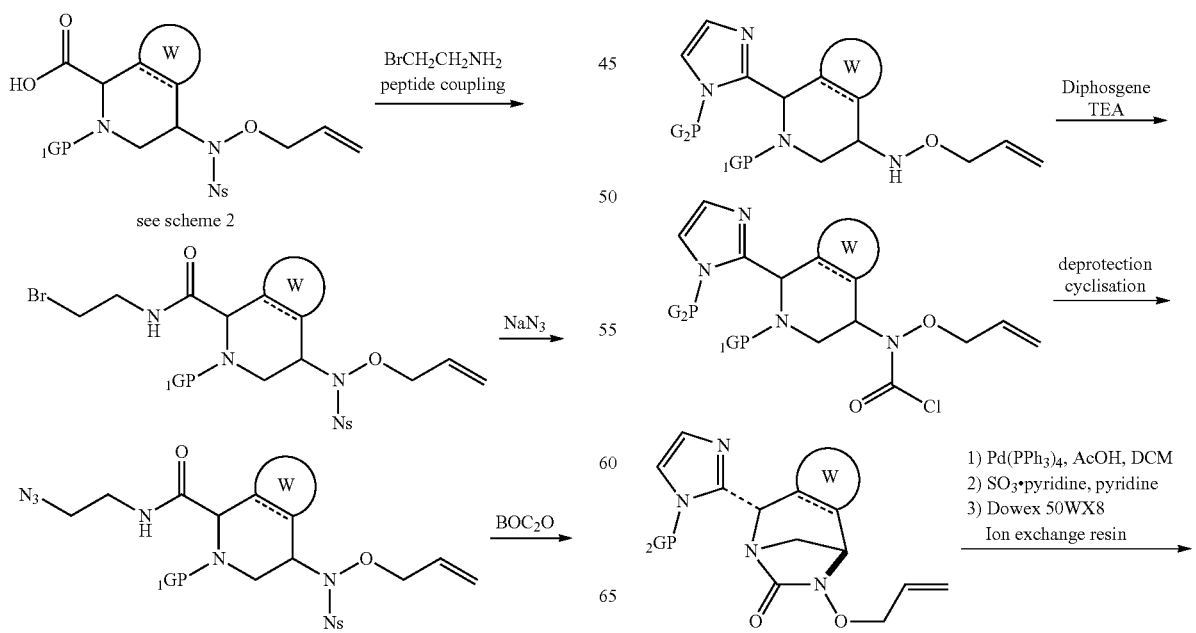

33
-continued
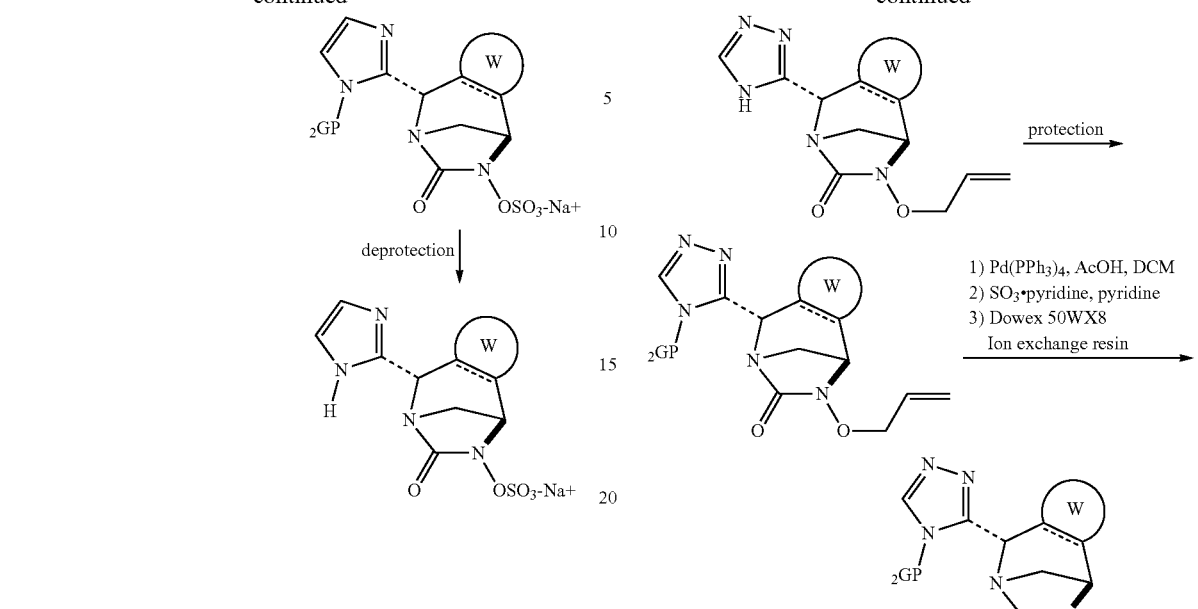
Scheme 5
34
-continued
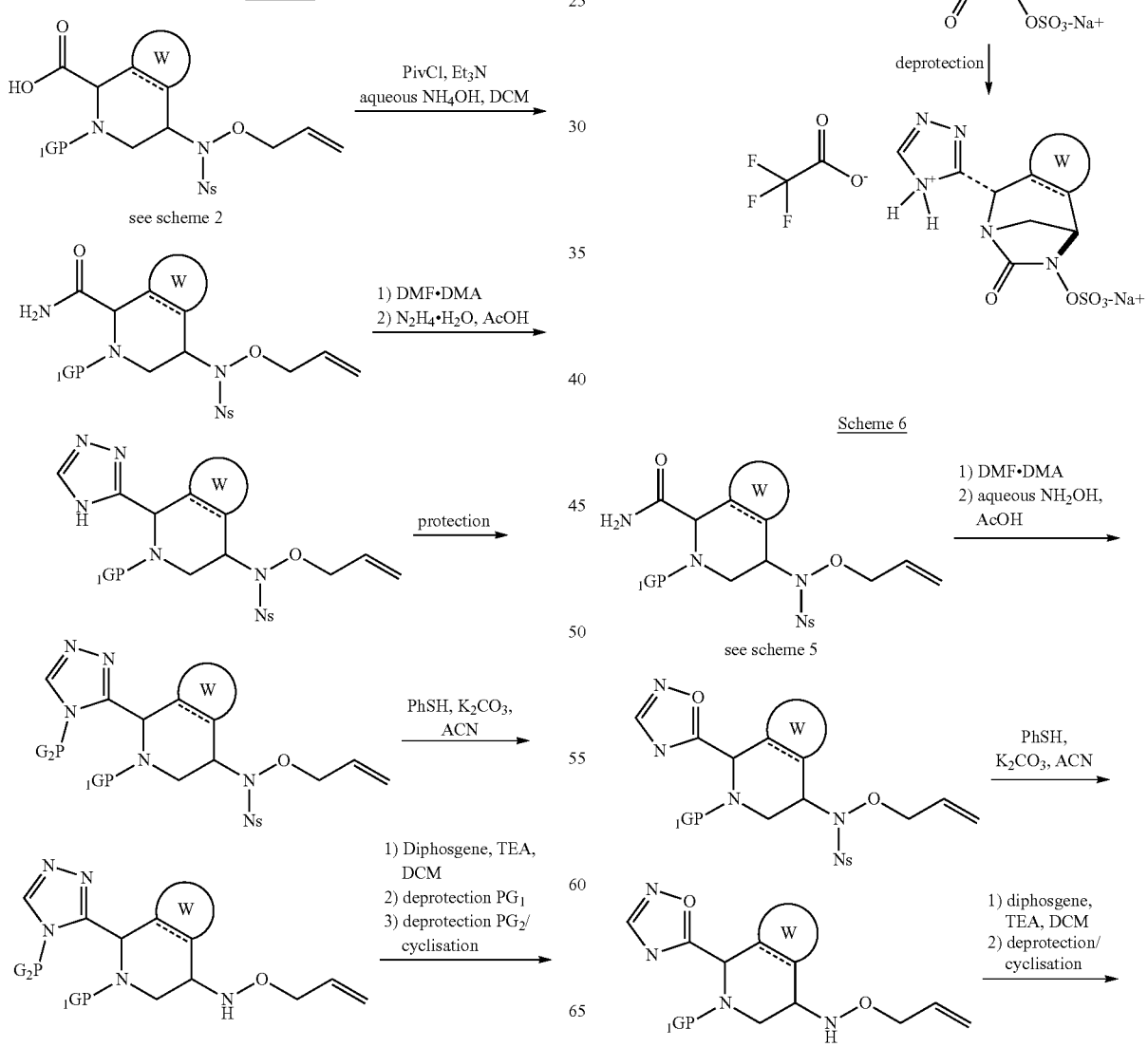
Scheme 6

35
-continued
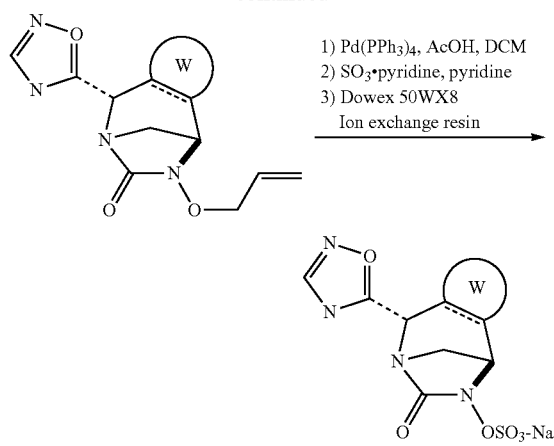
1) Pd(PPh₃)₄, AcOH, DCM
2) SO₃·pyridine, pyridine
3) Dowex 50WX8 Ion exchange resin
Scheme 7
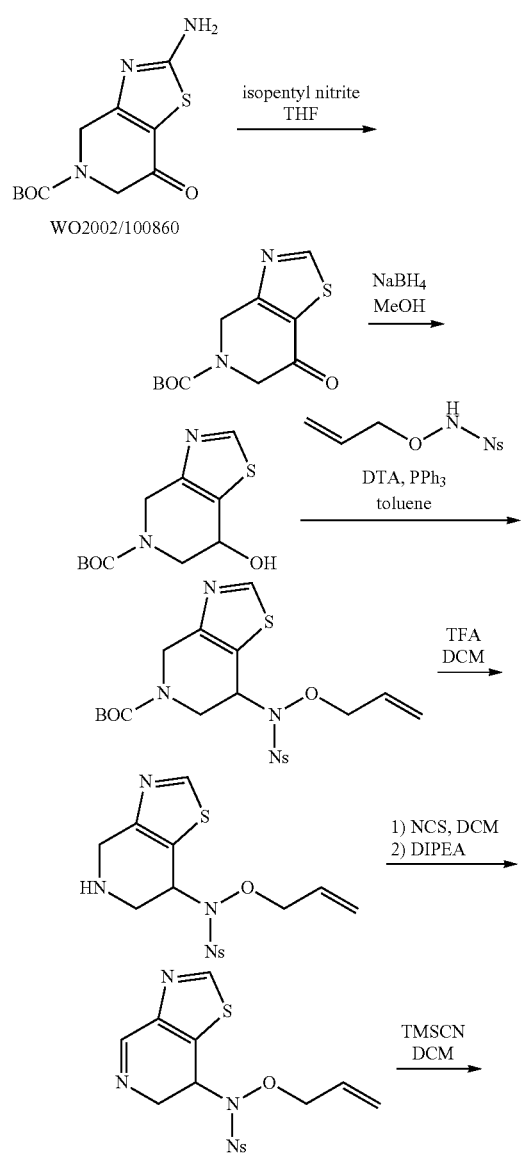
36
-continued
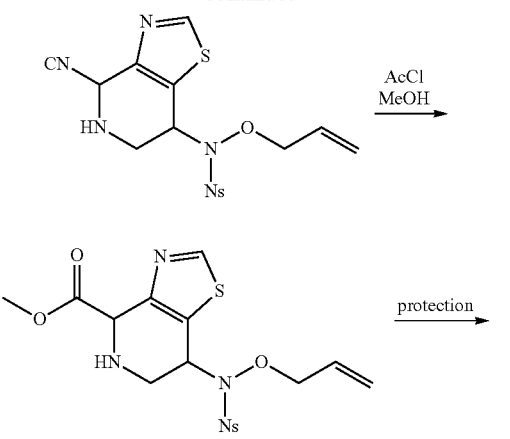
AcCl
MeOH
protection
PhSH, K₂CO₃, ACN
Diphosgene
TEA
deprotection
cyclisation
LiOH, THF
H₂O
RCONHNH₂
HATU, DIPEA
DCM
(CF₃SO₂)₂O, pyridine
or
Burgess reagent
or
PPh₃, I₂, TEA
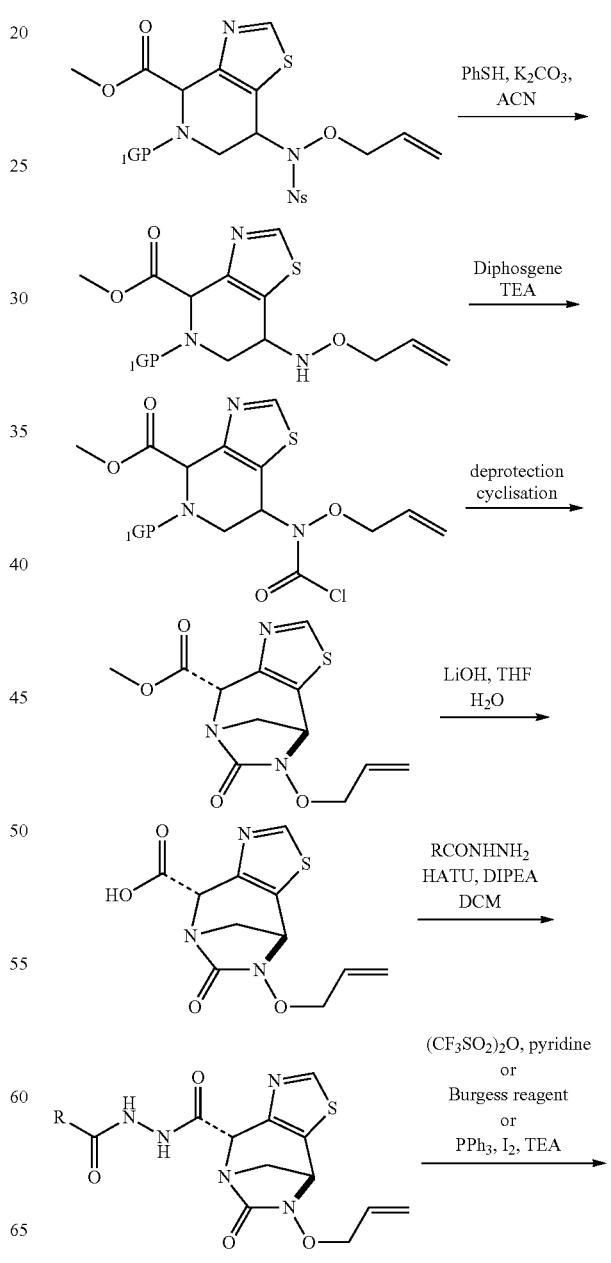

37
-continued
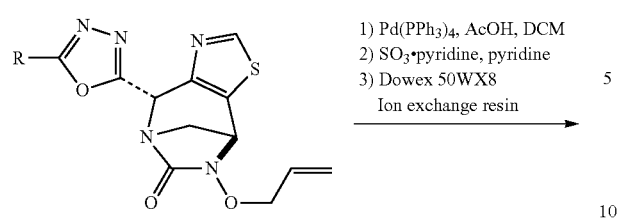
1) Pd(PPh₃)₄, AcOH, DCM
2) SO₃•pyridine, pyridine
3) Dowex 50WX8 Ion exchange resin
38
-continued
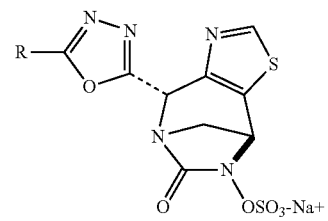
Scheme 8
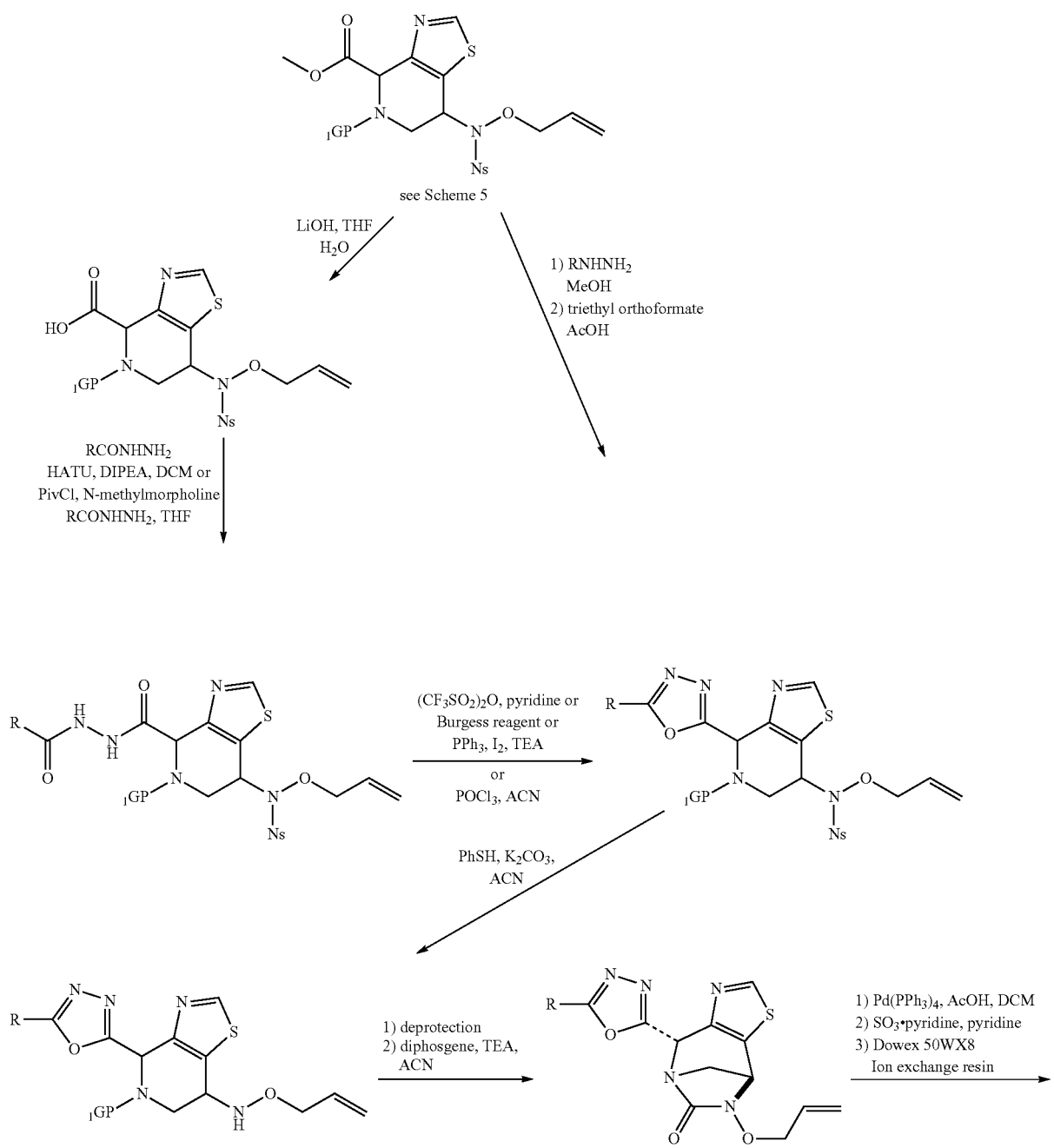

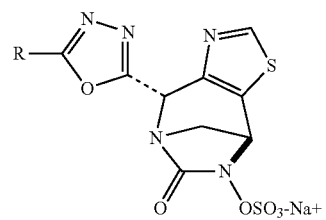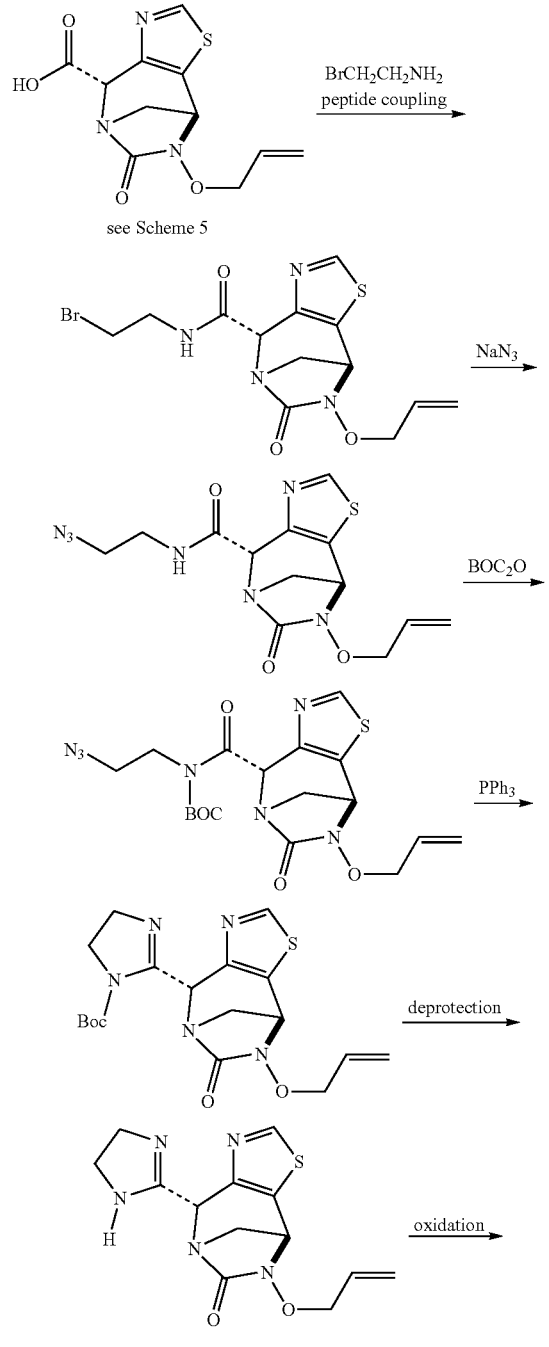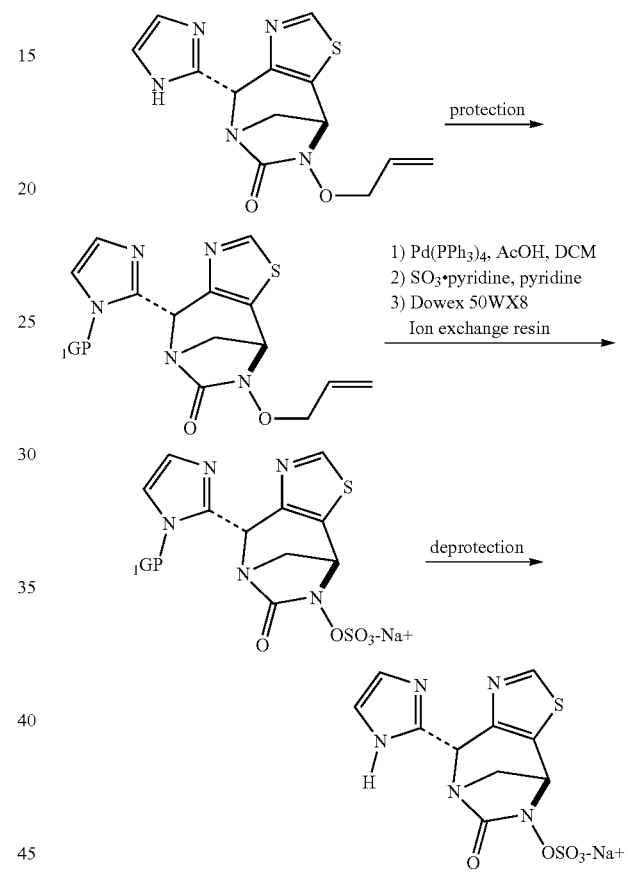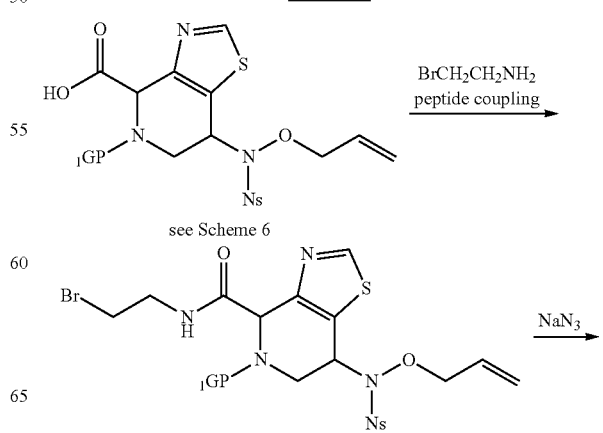

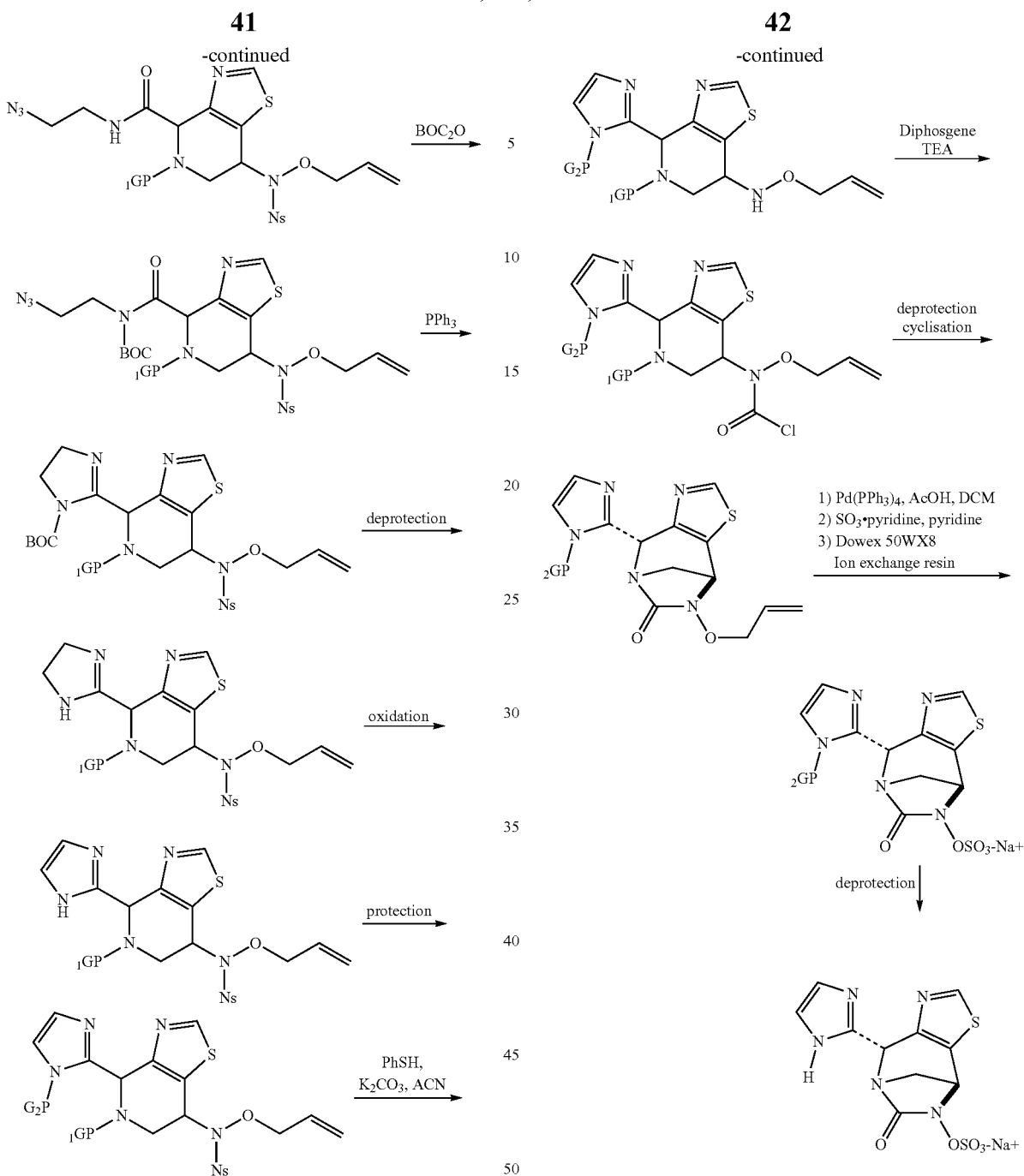
Scheme 11
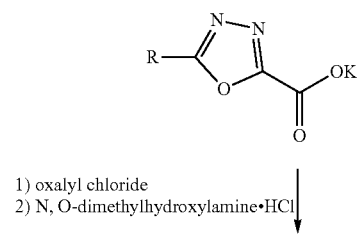
1) oxalyl chloride
2) N,O-dimethylhydroxylamine•HCl

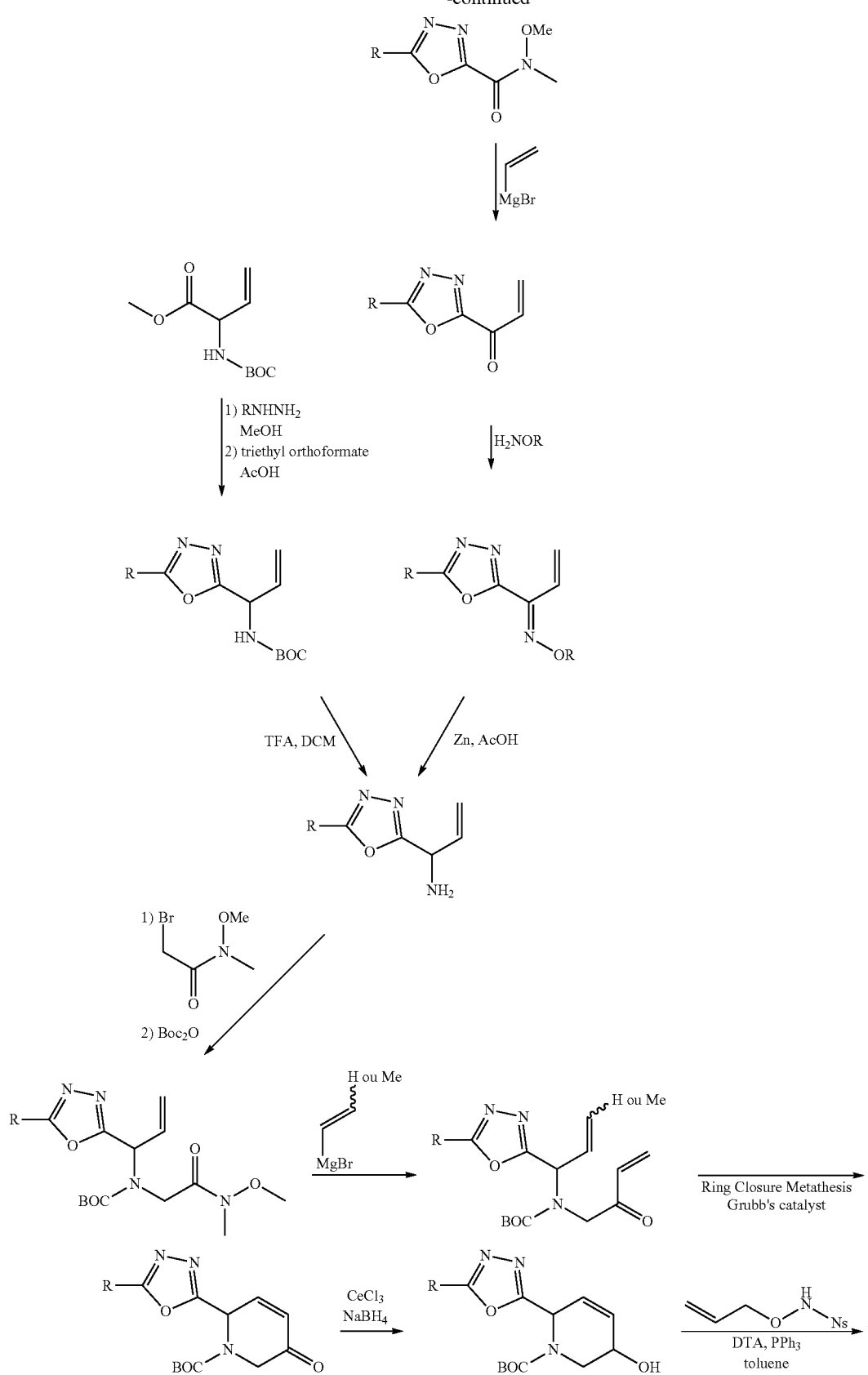

-continued
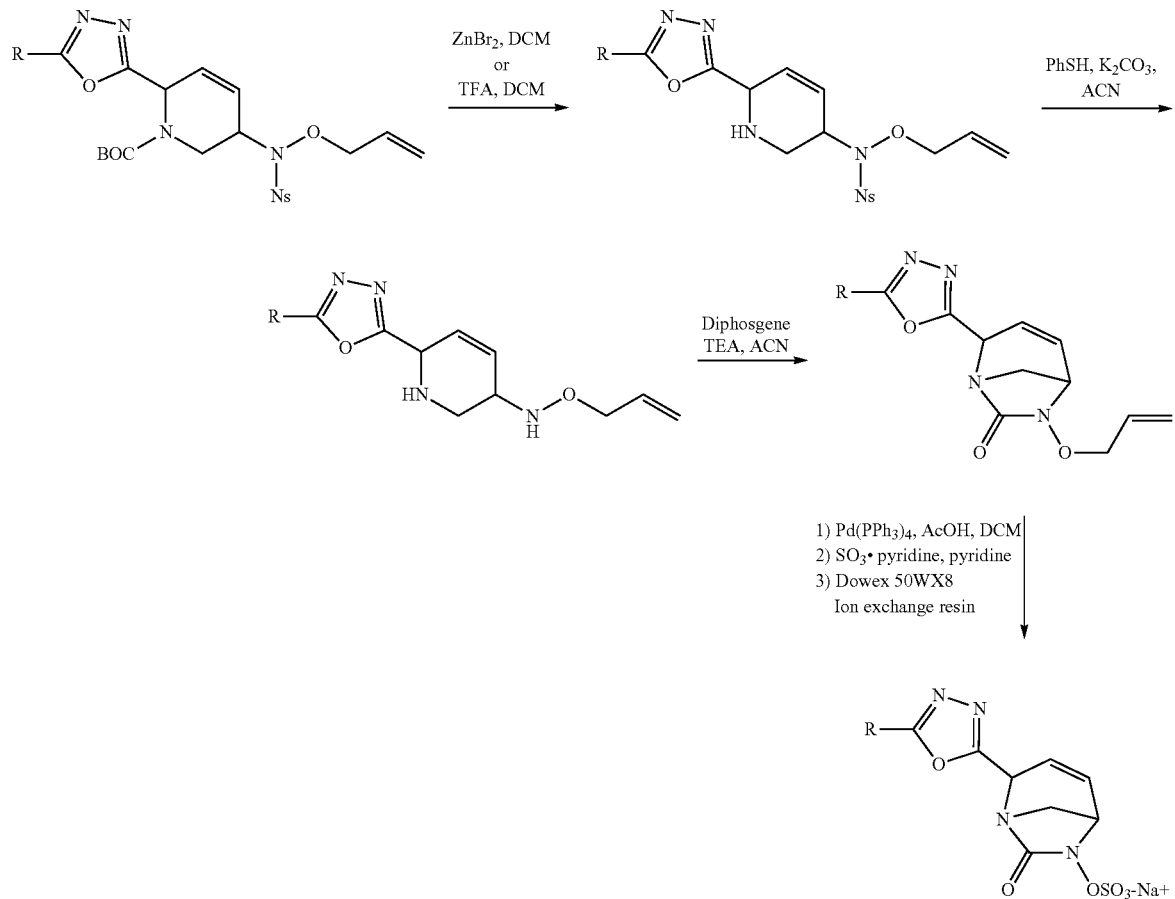
Scheme 12
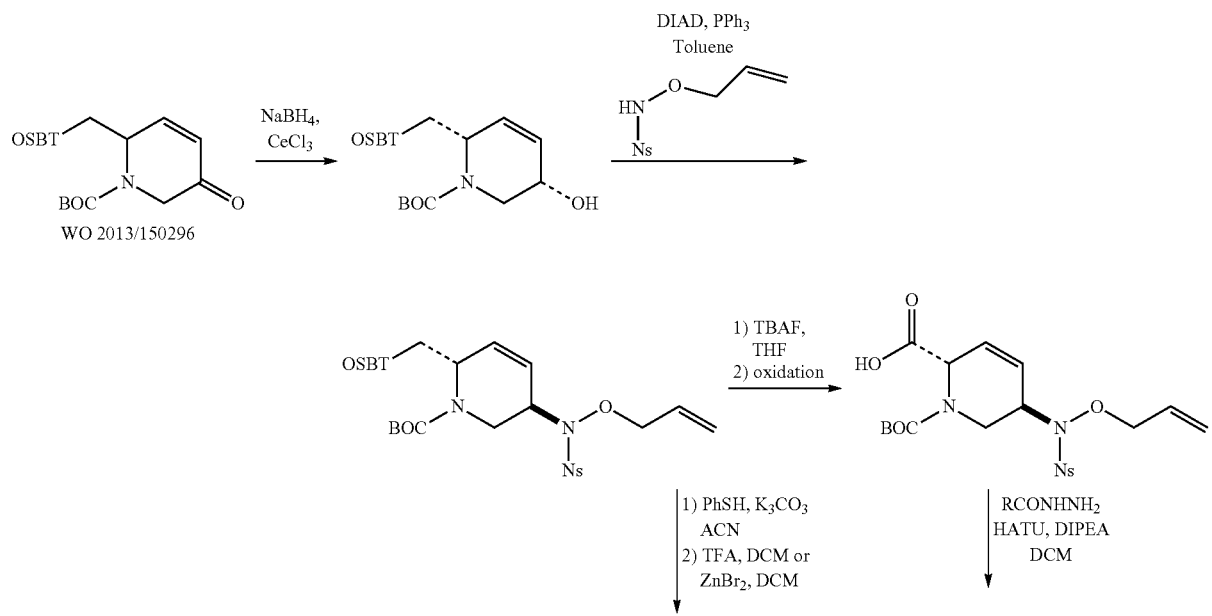

47 48
-continued
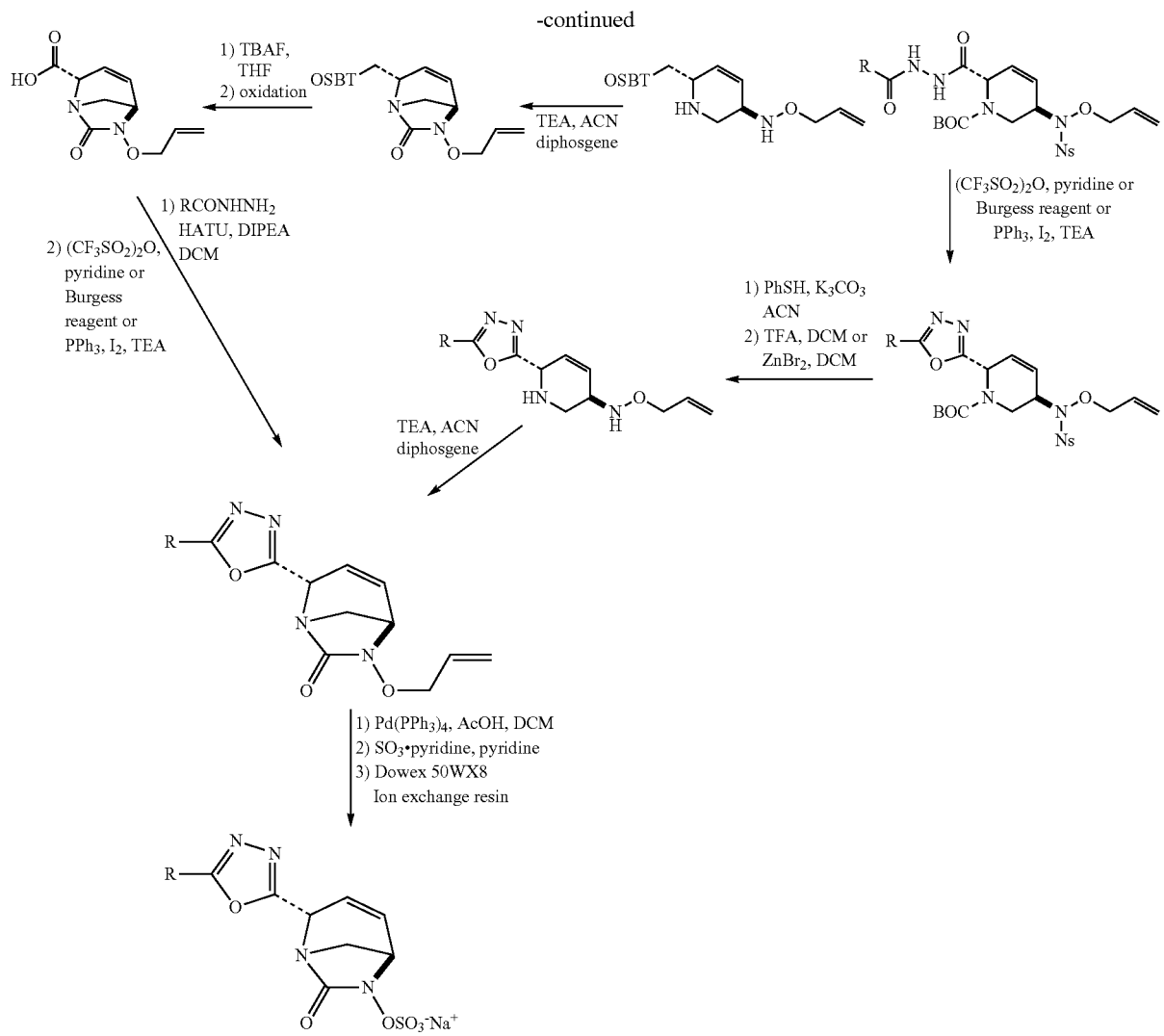
Example 1: Synthesis of Sodium and 2,2,2-trifluoroacetate [trans-7-(1H-imidazol-3-ium-2-yl)-9-oxo-3-thia-5,8,10-triaza-tricyclo[6.2.1.0$^{2,6}$]undeca-2(6),4-dien-10-yl]sulfate
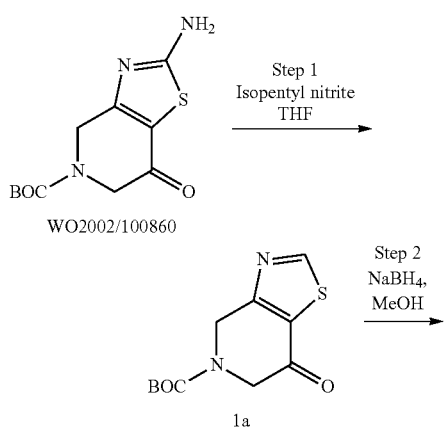
-continued
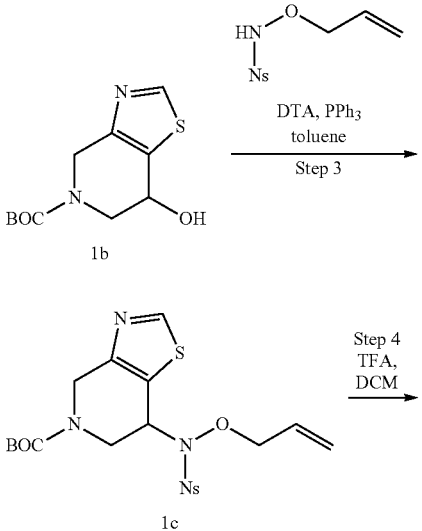

-continued
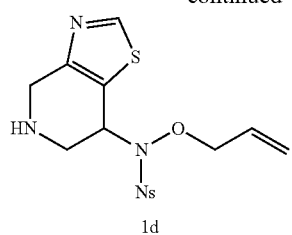
1d
Step 5
1) NCS, DCM
2) DIPEA, DCM
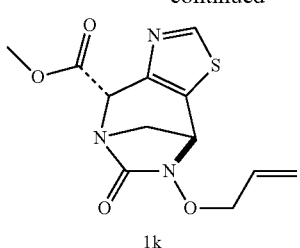
1k
LiOH, THF/H₂O
Step 12
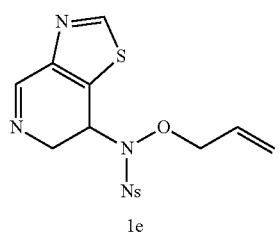
1e
Step 6
TMSCN, DCM
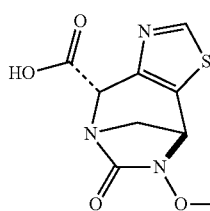
1l
Br-CH₂CH₂-NH₂ · HBr
Me-morpholine
PivCl, THF
Step 13
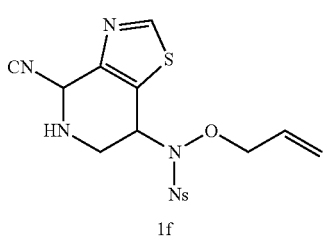
1f
Step 7
AcCl, MeOH
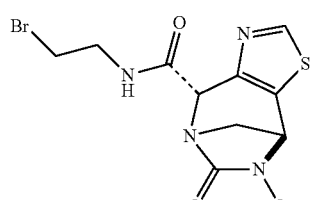
1m
NaN₃, NaI
Step 14
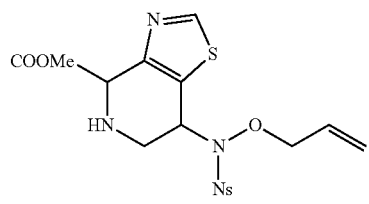
1g
Step 8
Benzylchloroformate
DIPEA, DCM
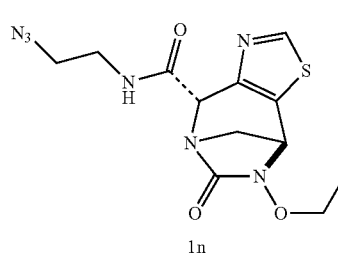
1n
Boc₂O, DMAP
ACN
Step 15
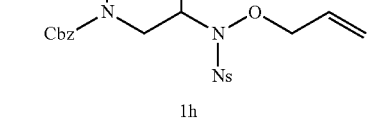
1h
Step 9
thiophenol, K₂CO₃
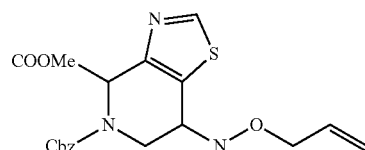
1i
Step 10
Diphosgene, TEA
ACN
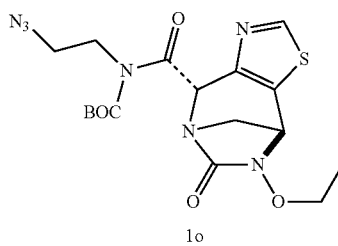
1o
Step 16
PPh₃, toluene
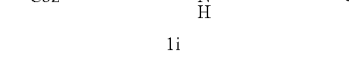
1j
Step 11
1) MeSO₃H
2) Et₃N, DCM
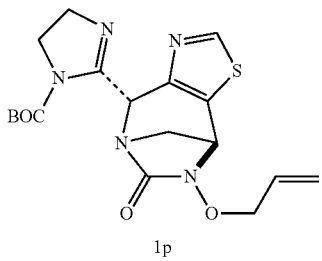
1p
Step 17
TFA, DCM -continued

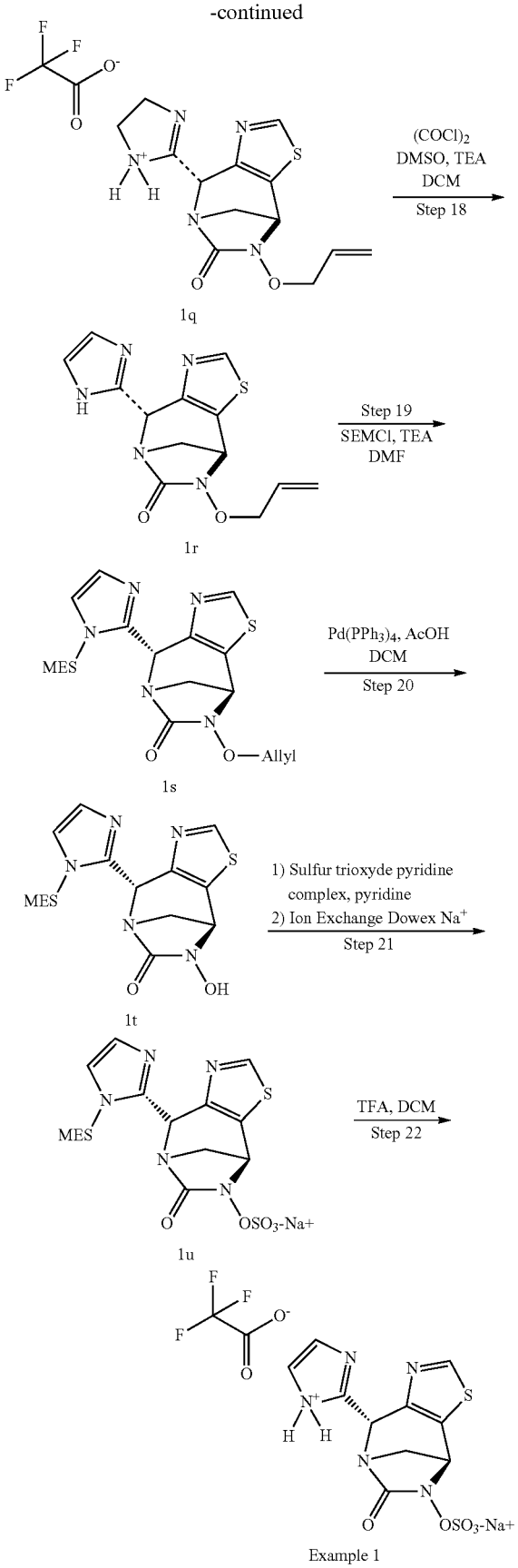

Example 1

Step 1: Preparation of Intermediate tert-butyl 7-oxo-4,6-dihydrothiazolo[4,5-c]pyridine-5-carboxylate (1a)

To a solution of tert-butyl 2-amino-7-oxo-4,6-dihydrothiazolo[4,5-c]pyridine-5-carboxylate (described in patent WO2002/100860) (15.87 g, 58.9 mmol) in anhydrous THF (500 mL) under inert atmosphere was added isopentyl nitrite (40 mL, 294 mmol) under 4 days. The solvent was evaporated in vacuo. The residue was solubilized in DCM and washed with water and brine. The organic layer was dried over $Na_2SO_4$ and evaporated in vacuo. The red solid was purified by flash chromatography on silica gel (DCM) to give tert-butyl 7-oxo-4,6-dihydrothiazolo[4,5-c]pyridine-5-carboxylate (1a) (10.83 g, 42.58 mmol, 72%) as an off-white solid.

MS m/z ([M+H]) 255.
$^1$H NMR (400 MHz, $CDCl_3$): δ (ppm) 1.49 (s, 9H), 4.35 (s, 2H), 4.95 (s, 2H), 9.08 (s, 1H).

Step 2: Preparation of Intermediate tert-butyl 7-hydroxy-6,7-dihydro-4H-thiazolo[4,5-c]pyridine-5-carboxylate (1b)

To a solution of tert-butyl 7-oxo-4,6-dihydrothiazolo[4,5-c]pyridine-5-carboxylate (1a) (27.2 g, 107 mmol) in MeOH (1550 mL) under inert atmosphere at 0° C. was portionwise added $NaBH_4$ (4.53 g, 120 mmol). The reaction mixture was stirred for 1 h at 0° C., then hydrolyzed with water and concentrated in vacuo. The residue was solubilized with DCM, washed with water and brine. The organic layer was dried over $Na_2SO_4$, evaporated in vacuo to give tert-butyl 7-hydroxy-6,7-dihydro-4H-thiazolo[4,5-c]pyridine-5-carboxylate (1b) (27.4 g, 106.9 mmol, quantitative yield) as a yellow solid without further purification.

MS m/z ([M+H]) 257.
$^1$H NMR (400 MHz, $CDCl_3$): δ (ppm) 1.49 (s, 9H), 3.69 (d, J=13.6 Hz, 1H), 3.97 (dd, J=13.6/4.6 Hz, 1H), 4.50 (d, J=17.1 Hz, 1H), 4.86 (d, J=14.5 Hz, 1H), 4.97 (bs, 1H), 8.75 (s, 1H).

Step 3: Preparation of Intermediate tert-butyl 7-[allyloxy-(2-nitrophenyl)sulfonyl-amino]-6,7-dihydro-4H-thiazolo[4,5-c]pyridine-5-carboxylate (1c)

To a solution of tert-butyl 7-hydroxy-6,7-dihydro-4H-thiazolo[4,5-c]pyridine-5-carboxylate (1b) (49.4 g, 193 mmol) in toluene (2.14 L) under inert atmosphere was added N-allyloxy-2-nitro-benzenesulfonamide (49.84 g, 193 mmol), $PPh_3$ (50.62 g, 193 mmol) and DTA (50.15 g, 218 mmol) portionwise. The reaction mixture was stirred for 24 h at rt. The precipitate was filtered off and the filtrate was concentrated in vacuo. The residue was purified by flash chromatography on silica gel (petroleum ether/acetone 100/0 to 60/40) to give tert-butyl 7-[allyloxy-(2-nitrophenyl)sulfonyl-amino]-6,7-dihydro-4H-thiazolo[4,5-c]pyridine-5-carboxylate (1c) (80.0 g, 161 mmol, 83%) as a yellow oil.

MS m/z ([M+H]) 497.
$^1$H NMR (400 MHz, $CDCl_3$): δ (ppm) 1.40 (s, 9H), 3.50 (bs, 1H), 4.00-4.50 (m, 4H), 4.75-5.05 (m, 3H), 5.25-5.60 (m, 2H), 7.64 (d, J=8.0 Hz, 1H), 7.73 (ddd, 7.8/7.8/1.5 Hz, 1H), 7.82 (ddd, J=7.8/7.8/1.5 Hz, 1H), 8.09 (d, J=8.0 Hz, 1H), 8.71 (s, 1H).

Step 4: Preparation of Intermediate N-allyloxy-2-nitro-N-(4,5,6,7-tetrahydrothiazolo[4,5-c]pyridin-7-yl)benzenesulfonamide (1d)

To a solution of tert-butyl 7-[allyloxy-(2-nitrophenyl)sulfonyl-amino]-6,7-dihydro-4H-thiazolo[4,5-c]pyridine-5- carboxylate (1c) (20.0 g, 40.28 mmol) in anhydrous DCM (37 mL) under inert atmosphere at 0° C. was dropwisely added TFA (37 mL, 483 mmol). After stirring for 2 h at rt, the reaction mixture was cooled at 0° C. and basified with ammonium hydroxide solution 28% until pH 8. The mixture was diluted with water and extracted with DCM. The organic layer was dried over $Na_2SO_4$, concentrated in vacuo to give N-allyloxy-2-nitro-N-(4,5,6,7-tetrahydrothiazolo[4,5-c]pyridin-7-yl)benzenesulfonamide (1d) (14.7 g, 37.0 mmol, 92%) as a yellow solid without further purification.

MS m/z ([M+H]) 397.

$^1$H NMR (400 MHz, $CDCl_3$): δ (ppm) 1.73 (bs, 1H), 3.03 (dd, J=14.7/4.9 Hz, 1H), 3.19 (bs, 1H), 3.88 (d, J=17.1 Hz, 1H), 4.02 (bs, 1H), 4.10 (d, J=17.1 Hz, 1H), 4.37 (dd, J=11.4/6.2 Hz, 1H), 5.02-5.13 (m, 2H), 5.14-5.20 (m, 1H), 5.47-5.59 (m, 1H), 7.65 (dd, J=7.7/1.4 Hz, 1H), 7.75 (ddd, J=7.7/7.7/1.4 Hz, 1H), 7.84 (ddd, J=7.7/7.7/1.5 Hz, 1H), 8.14 (dd, J=7.7/1.5 Hz, 1H), 8.77 (s, 1H).

Step 5: Preparation of Intermediate N-allyloxy-N-(6,7-dihydrothiazolo[4,5-c]pyridin-7-yl)-2-nitro-benzenesulfonamide (1e)

To a solution of N-allyloxy-2-nitro-N-(4,5,6,7-tetrahydrothiazolo[4,5-c]pyridin-7-yl)benzenesulfonamide (1d) (14.7 g, 37.0 mmol) in anhydrous DCM (225 mL) under inert atmosphere at 0° C. was dropwisely added a solution of N-chlorosuccinimide (6.43 g, 48.14 mmol) in DCM (225 mL). After stirring for 4 h at 0° C., DIPEA (24 mL, 138 mmol) was added and the reaction mixture was stirred for 18 h at rt. The reaction mixture was cooled at 0° C., washed with a tartaric acid solution (2 eq/DIPEA) and extracted with DCM. The organic layer was dried over $Na_2SO_4$ and concentrated in vacuo to give N-allyloxy-N-(6,7-dihydrothiazolo[4,5-c]pyridin-7-yl)-2-nitro-benzenesulfonamide (1e) (14.6 g, 37.0 mmol, quantitative yield) as an ochre solid without further purification.

MS m/z ([M+H]) 395.

Step 6: Preparation of Intermediate N-allyloxy-N-(4-cyano-4,5,6,7-tetrahydrothiazolo[4,5-c]pyridin-7-yl)-2-nitro-benzenesulfonamide (1f)

To a solution of N-allyloxy-N-(6,7-dihydrothiazolo[4,5-c]pyridin-7-yl)-2-nitro-benzenesulfonamide (1e) (14.6 g, 37.0 mmol) in anhydrous DCM (260 mL) under inert atmosphere at 0° C. was added TMSCN (47 mL, 377 mmol). The reaction mixture was stirred for 9 days at rt. The solvent was evaporated and the residue was purified by flash chromatography on silica gel (DCM/acetone 90/10) to give N-allyloxy-N-(4-cyano-4,5,6,7-tetrahydrothiazolo[4,5-c]pyridin-7-yl)-2-nitro-benzenesulfonamide (1f) (12.7 g, 30.0 mmol, 81%) as a beige solid.

MS m/z ([M+H]) 422.

$^1$H NMR (400 MHz, $CDCl_3$): δ (ppm) 2.33 (bs, 1H), 3.38 (bs, 2H), 4.04 (bs, 1H), 4.36 (dd, J=11.4/6.1 Hz, 1H), 4.98-5.21 (m, 4H), 5.44-5.54 (m, 1H), 7.68 (dd, J=7.8/1.3 Hz, 1H), 7.76 (ddd, J=7.7/7.7/1.3 Hz, 1H), 7.86 (ddd, J=7.8/7.8/1.4 Hz, 1H), 8.12 (dd, J=7.7/1.4 Hz, 1H), 8.83 (s, 1H).

Step 7: Preparation of Intermediate methyl 7-[allyloxy-(2-nitrophenyl)sulfonyl-amino]-4,5,6,7-tetrahydrothiazolo[4,5-c]pyridine-4-carboxylate (1q)

In MeOH (72 mL) at 0° C. under inert atmosphere was added AcCl (30 mL, 422 mmol). After stirring for 2 h at 0° C. then for 30 min at rt, a solution of N-allyloxy-N-(4-cyano-4,5,6,7-tetrahydrothiazolo[4,5-c]pyridin-7-yl)-2-nitro-benzenesulfonamide (1f) (12.7 g, 30.0 mmol) in MeOH (36 mL) was added. The mixture was heated at 50° C. for 18 h. The solvent was evaporated. The residue was extracted with DCM and washed with a saturated solution of $NaHCO_3$. The organic layer was dried over $Na_2SO_4$ and concentrated in vacuo. The brown oil was purified by flash chromatography on silica gel (DCM/acetone 100/0 to 80/20) to give methyl 7-[allyloxy-(2-nitrophenyl)sulfonyl-amino]-4,5,6,7-tetrahydrothiazolo[4,5-c]pyridine-4-carboxylate (1g) (10.8 g, 23.7 mmol, 78%) as a yellow solid.

MS m/z ([M+H]) 455.

$^1$H NMR (400 MHz, $CDCl_3$): δ (ppm) 3.20-3.57 (m, 2H), 3.48, 3.54, 3.79 and 3.88 (s, 3H), 4.05-4.16 (m, 1H), 4.34 and 4.43 (dd, J=11.1/6.6 Hz, 1H), 4.90 and 5.00 (s, 1H), 5.02-5.21 (m, 2H), 5.27-5.41 (m, 1H), 5.47-5.69 (m, 1H), 7.67 (t, J=7.7 Hz, 1H), 7.74-7.81 (m, 1H), 7.82-7.89 (m, 1H), 8.13-8.19 (m, 1H), 8.83 and 8.84 (s, 1H).

(Mixture of Diastereoisomers)

Step 8: Preparation of Intermediate O5-benzyl O4-methyl 7-[allyloxy-(2-nitrophenyl)sulfonyl-amino]-6,7-dihydro-4H-thiazolo[4,5-c]pyridine-4,5-dicarboxylate (1h)

To a solution of methyl 7-[allyloxy-(2-nitrophenyl)sulfonyl-amino]-4,5,6,7-tetrahydrothiazolo[4,5-c]pyridine-4-carboxylate (1g) (10.8 g, 23.7 mmol) in anhydrous DCM (230 mL) under inert atmosphere at −78° C. were successively added DIPEA (8.3 mL, 47.4 mmol) and benzyl chloroformate (4.1 mL, 28.4 mmol). The mixture was stirred at rt for 2.5 h then water was added. The aqueous layer was extracted with DCM. The organic layers were combined, washed with a saturated solution of sodium bicarbonate, dried over $Na_2SO_4$ and concentrated in vacuo. The residue was purified by flash chromatography on silica gel (DCM/acetone 100/0 to 90/10) to give O5-benzyl O4-methyl 7-[allyloxy-(2-nitrophenyl)sulfonyl-amino]-6,7-dihydro-4H-thiazolo[4,5-c]pyridine-4,5-dicarboxylate (1h) (13.1 g, 22.2 mmol, 93%) as a yellow solid.

MS m/z ([M+H]) 589.

Step 9: Preparation of Intermediate O5-benzyl O4-methyl 7-(allyloxyamino)-6,7-dihydro-4H-thiazolo[4,5-c]pyridine-4,5-dicarboxylate (1i)

To a solution of O5-benzyl O4-methyl 7-[allyloxy-(2-nitrophenyl)sulfonyl-amino]-6,7-dihydro-4H-thiazolo[4,5-c]pyridine-4,5-dicarboxylate (1h) (13.1 g, 22.2 mmol) in ACN (145 mL) under inert atmosphere at 0° C. were successively added PhSH (11.4 mL, 111 mmol) and potassium carbonate (23 g, 167 mmol). The mixture was stirred at rt for 18 h then filtered through a pad of Celite® and rinsed with DCM. The filtrate was concentrated in vacuo. The residue was purified by flash chromatography on silica gel (heptane/EtOAc 100/0 to 20/80) to give O5-benzyl O4-methyl 7-(allyloxyamino)-6,7-dihydro-4H-thiazolo[4,5-c]pyridine-4,5-dicarboxylate (1i) (7.87 g, 19.5 mmol, 87%) as an ochre oil.

MS m/z ([M+H]) 404.

Step 10: Preparation of Intermediate O5-benzyl O4-methyl 7-[allyloxy(chlorocarbonyl)amino]-6,7-dihydro-4H-thiazolo(chlorocarbon[4,5-c]pyridine-4,5-dicarboxylate (1j)

To a solution of O5-benzyl O4-methyl 7-(allyloxyamino)-6,7-dihydro-4H-thiazolo[4,5-c]pyridine-4,5-dicarboxylate (1i) (7.87 g, 19.5 mmol) in ACN (365 mL) under inert atmosphere at −10° C. was added TEA (8.2 mL, 58.5 mmol). A solution of diphosgene (3.1 mL, 25.3 mmol) diluted in ACN (45 mL) was dropwisely added. After stirring for 10 min at 0° C., the solvent was evaporated and the residue was purified by flash chromatography on silica gel (heptane/EtOAc 100/0 to 50/50) to give O5-benzyl O4-methyl 7-[allyloxy(chlorocarbonyl)amino]-6,7-dihydro-4H-thiazolo[4,5-c]pyridine-4,5-dicarboxylate (1j) (8.44 g, 18.1 mmol, 93%) as a yellow oil.

MS m/z ([M/M+2]) 466/468.

Step 11: Preparation of Intermediate methyl trans-10-allyloxy-9-oxo-3-thia-5,8,10-triaza-tricyclo[6.2.1.0$^{2,6}$]undeca-2(6),4-diene-7-carboxylate (1k)

To a solution of O5-benzyl O4-methyl 7-[allyloxy(chlorocarbonyl)amino]-6,7-dihydro-4H-thiazolo[4,5-c]pyridine-4,5-dicarboxylate (1j) (7.40 g, 15.9 mmol) in anhydrous DCM (100 mL) under inert atmosphere at 0° C. was dropwise added methanesulfonic acid (26 mL, 397 mmol). After stirring for 2 h at rt, the reaction mixture was poured at −78° C. in a solution of TEA (110 mL, 794 mmol) in DCM (74 mL) and stirred for 30 min. The mixture was washed with water and extracted with DCM. The organic layer was dried over Na$_2$SO$_4$ and concentrated in vacuo. The residue was purified by flash chromatography on silica gel (DCM/EtOAc 100/0 to 85/15) to give methyl trans-10-allyloxy-9-oxo-3-thia-5,8,10-triaza-tricyclo[6.2.1.0$^{2,6}$]undeca-2(6),4-diene-7-carboxylate (1k) (4.50 g, 15.2 mmol, 96%) as an off-white solid.

MS m/z ([M+H]) 296.

$^1$H NMR (300 MHz, CDCl$_3$): δ (ppm) 3.60 (dd, J=11.6/2.8 Hz, 1H), 3.70 (dd, J=11.6/0.8 Hz, 1H), 3.81 (s, 3H), 4.32-4.46 (m, 2H), 4.65 (dd, J=2.8/0.8 Hz, 1H), 5.25-5.35 (m, 3H), 5.88-6.01 (m, 1H), 8.68 (s, 1H).

Step 12: Preparation of Intermediate trans-10-allyloxy-9-oxo-3-thia-5,8,10-triaza-tricyclo[6.2.1.0$^{2,6}$]undeca-2(6),4-diene-7-carboxylic Acid (1l)

To a solution of methyl trans-10-allyloxy-9-oxo-3-thia-5,8,10-triaza-tricyclo[6.2.1.0$^{2,6}$]undeca-2(6),4-diene-7-carboxylate (1k) (1.60 g, 5.42 mmol) in a mixture of THF (30 mL) and water (19 mL) at 0° C. was dropwisely added a 1N solution of lithium hydroxide (5.4 mL, 5.42 mmol). After stirring for 24 h, the mixture was diluted with DCM and acidified with a 2N solution of HCl (6 mL) at 0° C. The product was extracted with DCM and the organic layer was dried over Na$_2$SO$_4$ before being concentrated in vacuo. The crude was triturated with Et$_2$O to give trans-10-allyloxy-9-oxo-3-thia-5,8,10-triaza-tricyclo[6.2.1.0$^{2,6}$]undeca-2(6),4-diene-7-carboxylic acid (1l) (1.52 g, 5.42 mmol, quantitative yield) as a white solid without further purification.

MS m/z ([M+H]) 282.

$^1$H NMR (400 MHz, CDCl$_3$): δ (ppm) 3.59 (d, J=11.7 Hz, 1H), 3.72 (dd, J=11.7/2.8 Hz, 1H), 4.18 (bs, 1H), 4.38-4.50 (m, 1H), 4.67 (d, J=2.6 Hz, 1H), 5.30-5.40 (m, 2H), 5.41 (s, 1H), 5.94-6.05 (m, 1H), 8.89 (s, 1H).

Step 13: Preparation of Intermediate trans-10-allyloxy-N-(2-bromoethyl)-9-oxo-3-thia-5,8,10-triaza-tricyclo[6.2.1.0$^{2,6}$]undeca-2(6),4-diene-7-carboxamide (1m)

To a solution of trans-10-allyloxy-9-oxo-3-thia-5,8,10-triaza-tricyclo[6.2.1.0$^{2,6}$]undeca-2(6),4-diene-7-carboxylic acid (1l) (1.40 g, 4.98 mmol) in anhydrous THF (50 mL) under inert atmosphere at −50° C. was added 4-methylmorpholine (3.3 mL, 29.9 mmol). After stirring for 15 min trimethylacetyl chloride (0.92 mL, 7.47 mmol) was added and the mixture was maintained at −50° C. for 1 h. 2-Bromoethylamine hydrobromide (3.06 g, 14.9 mmol) was portionwise added and temperature was raised to −30° C. for 2 h. The precipitate was filtered off and washed with EtOAc. The filtrate was concentrated in vacuo to give trans-10-allyloxy-N-(2-bromoethyl)-9-oxo-3-thia-5,8,10-triaza-tricyclo[6.2.1.0$^{2,6}$]undeca-2(6),4-diene-7-carboxamide (1m) (1.93 g, 4.98 mmol, quantitative yield) as a yellow oil which was used without further purification without further purification.

MS m/z ([M/M+2]) 387/389.

$^1$H NMR (400 MHz, CDCl$_3$): δ (ppm) 3.39 (dd, J=11.5/0.07 Hz, 1H), 3.44-3.53 (m, 2H), 3.62-3.74 (m, 2H), 3.76-3.84 (m, 1H), 4.38-4.49 (m, 1H), 4.66 (d, J=2.3 Hz, 1H), 5.25 (s, 1H), 5.29-5.41 (m, 2H), 5.94-6.04 (m, 1H), 7.43 (dd, J=5.9/5.9 Hz, 1H), 8.75 (s, 1H).

Step 14: Preparation of Intermediate trans-10-allyloxy-N-(2-azidoethyl)-9-oxo-3-thia-5,8,10-triaza-tricyclo[6.2.1.0$^{2,6}$]undeca-2(6),4-diene-7-carboxamide (1n)

To a solution of trans-10-allyloxy-N-(2-bromoethyl)-9-oxo-3-thia-5,8,10-triaza-tricyclo[6.2.1.0$^{2,6}$]undeca-2(6),4-diene-7-carboxamide (1m) (1.93 g, 4.98 mmol) in anhydrous DMF (50 mL) under inert atmosphere were successively added sodium iodide (1.49 g, 9.96 mmol) and sodium azide (0.65 g, 9.96 mmol). The reaction mixture was stirred for 1 h at 40° C. then overnight at rt. The solvent was evaporated. DCM was added to the residue. The solids were filtered off and rinsed with DCM. The filtrate was concentrated in vacuo. The residue was purified by flash chromatography on silica gel (DCM/acetone 100/0 to 80/20) then triturated in Et$_2$O to give trans-10-allyloxy-N-(2-azidoethyl)-9-oxo-3-thia-5,8,10-triaza-tricyclo[6.2.1.0$^{2,6}$]undeca-2(6),4-diene-7-carboxamide (1n) (1.15 g, 3.29 mmol, 66%) as a white solid.

MS m/z ([M+H]) 350.

$^1$H NMR (400 MHz, CDCl$_3$): δ (ppm) 3.39 (d, J=11.5 Hz, 1H), 3.42-3.54 (m, 4H), 3.69 (dd, J=11.5/2.9 Hz, 1H), 4.37-4.48 (m, 2H), 4.65 (d, J=2.7 Hz, 1H), 5.24 (s, 1H), 5.29-5.38 (m, 2H), 5.93-6.03 (m, 1H), 7.35 (d, J=6.1 Hz, 1H), 8.74 (s, 1H).

Step 15: Preparation of Intermediate tert-butyl N-(2-azidoethyl)-N-[trans-10-allyloxy-9-oxo-3-thia-5,8,10-triaza-tricyclo[6.2.1.0$^{2,6}$]undeca-2(6),4-diene-7-carbonyl)]carbamate (1o)

To a solution of trans-10-allyloxy-N-(2-azidoethyl)-9-oxo-3-thia-5,8,10-triaza-tricyclo[6.2.1.0$^{2,6}$]undeca-2(6),4-diene-7-carboxamide (1n) (1.15 g, 3.29 mmol) in anhydrous ACN (33 mL) under inert atmosphere at rt were successively added Boc$_2$O (1.08 g, 4.94 mmol) and 4-dimethylaminopyridine (40 mg, 0.33 mmol). The mixture was stirred for 3 days. The solvent was evaporated in vacuo and the residue was purified by flash chromatography on silica gel (DCM/Et$_2$O 100/0 to 90/10) to give tert-butyl N-(2-azidoethyl)-N-[trans-10-allyloxy-9-oxo-3-thia-5,8,10-triaza-tricyclo[6.2.1.0$^{2,6}$]undeca-2(6),4-diene-7-carbonyl)]carbamate (1O) (1.10 g, 2.45 mmol, 74%) as a yellow solid.

MS m/z ([M+H]) 450.

¹H NMR (400 MHz, CDCl₃): δ (ppm) 1.62 (s, 9H), 3.47 (dd, J=6.0 Hz, 2H), 3.52 (d, J=11.4 Hz, 1H), 3.59 (dd, J=11.5/2.8 Hz, 1H), 3.88 (ddd, J=14.0/6.4/6.4 Hz, 1H), 4.00 (ddd, J=14.0/5.8/5.8 Hz, 1H), 4.38-4.49 (m, 2H), 4.64 (d, J=2.8 Hz, 1H), 5.30-5.39 (m, 2H), 5.95-6.05 (m, 1H), 6.44 (s, 1H), 8.70 (s, 1H).

Step 16: Preparation of Intermediate tert-butyl 2-(trans-10-allyloxy-9-oxo-3-thia-5,8,10-triaza-tricyclo[6.2.1.0²,⁶]undeca-2(6),4-dien-7-yl)-4,5-dihydroimidazole-1-carboxylate (1p)

To a solution of tert-butyl N-(2-azidoethyl)-N-[trans-10-allyloxy-9-oxo-3-thia-5,8,10-triaza-tricyclo[6.2.1.0²,⁶]undeca-2(6),4-diene-7-carbonyl)]carbamate (1o) (1.10 g, 2.45 mmol) in anhydrous toluene (41 mL) under inert atmosphere was added PPh₃ (0.64 g, 2.45 mmol). The mixture was stirred for 16 h at rt, deposited on silica and purified by flash chromatography on silica gel (Heptane/Acetone 100/0 to 0/100) to give tert-butyl 2-(trans-10-allyloxy-9-oxo-3-thia-5,8,10-triaza-tricyclo[6.2.1.0²,⁶]undeca-2(6),4-dien-7-yl)-4,5-dihydroimidazole-1-carboxylate (1p) (910 mg, 2.24 mmol, 91%) as a white solid.

MS m/z ([M+H]) 406.
¹H NMR (400 MHz, CDCl₃): δ (ppm) 1.56 (s, 9H), 3.42 (dd, J=11.3/2.9 Hz, 1H), 3.64-3.93 (m, 5H), 4.33-4.47 (m, 2H), 4.61 (d, J=2.2 Hz, 1H), 5.24-5.35 (m, 2H), 5.90-6.04 (m, 1H), 6.32 (s, 1H), 8.66 (s, 1H).

Step 17: Preparation of Intermediate trans-10-allyloxy-7-(4,5-dihydro-1H-imidazol-3-ium-2-yl)-3-thia-5,8,10-triaza-tricyclo[6.2.1.0²,⁶]undeca-2(6),4-dien-9-one trifluoroacetate (1q)

To a solution of tert-butyl 2-(trans-10-allyloxy-9-oxo-3-thia-5,8,10-triaza-tricyclo[6.2.1.0²,⁶]undeca-2(6),4-dien-7-yl)-4,5-dihydroimidazole-1-carboxylate (1p) (240 mg, 0.59 mmol) in anhydrous DCM (4.3 mL) under inert atmosphere at 0° C. was dropwisely added TFA (4.3 mL, 56.2 mmol). The mixture was stirred at rt for 16 h then concentrated in vacuo. The residue was co-evaporated with toluene to give trans-10-allyloxy-7-(4,5-dihydro-1H-imidazol-3-ium-2-yl)-3-thia-5,8,10-triaza-tricyclo[6.2.1.0²,⁶]undeca-2(6),4-dien-9-one trifluoroacetate (1q) (247 mg, 0.59 mmol, quantitative yield) without further purification.

MS m/z ([M+H]) 306.

Step 18: Preparation of trans-10-allyloxy-7-(1H-imidazol-2-yl)-3-thia-5,8,10-triaza-tricyclo[6.2.1.0²,⁶]undeca-2(6),4-dien-9-one (1r)

To a solution of oxalyl chloride (0.1 mL, 1.18 mmol) in DCM (9 mL) under inert atmosphere at −65° C. was dropwise added dimethyl sulfoxide (0.17 mL, 2.36 mmol). The mixture was stirred for 30 min then a solution of trans-10-allyloxy-7-(4,5-dihydro-1H-imidazol-3-ium-2-yl)-3-thia-5,8,10-triaza-tricyclo[6.2.1.0²,⁶]undeca-2(6),4-dien-9-one trifluoroacetate (1q) (247 mg, 0.59 mmol) in anhydrous DCM (9 mL) was dropwisely added. After 5 min at −65° C., TEA (0.82 mL, 5.89 mmol) was added and the temperature was raised to −15° C. for 3 h. The reaction mixture was quenched with water and the product was extracted with DCM. The brown oil was purified by flash chromatography on silica gel (heptane/acetone 100/0 to 0/100) to give trans-10-allyloxy-7-(1H-imidazol-2-yl)-3-thia-5,8,10-triaza-tricyclo[6.2.1.0²,⁶]undeca-2(6),4-dien-9-one (1r) (59 mg, 0.19 mmol, 32%) as an off-white solid.

MS m/z ([M+H]) 304.
¹H NMR (400 MHz, CDCl₃): δ (ppm) 3.49 (dd, J=11.4/2.9 Hz, 1H), 3.76 (d, J=11.4 Hz, 1H), 4.40-4.52 (m, 2H), 4.69 (d, J=2.3 Hz, 1H), 5.31-5.41 (m, 2H), 5.86 (s, 1H), 5.96-6.06 (m, 1H), 7.04 (s, 2H), 8.74 (s, 1H), 10.48 (bs, 1H).

Step 19: Preparation of trans-10-allyloxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1s)

To a solution of trans-10-allyloxy-7-(1H-imidazol-2-yl)-3-thia-5,8,10-triaza-tricyclo[6.2.1.0²,⁶]undeca-2(6),4-dien-9-one (1r) (59 mg, 0.19 mmol) in anhydrous DMF (2 mL) under inert atmosphere were successively added (2-(chloromethoxy)ethyl)trimethylsilane (0.10 mL, 0.58 mmol) and TEA (0.08 mL, 0.58 mmol). After stirring for 16 h at rt, the mixture was concentrated in vacuo. The residue was purified by flash chromatography on silica gel (DCM/Acetone 80/20 to 0/100) to give trans-10-allyloxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1s) (43 mg, 0.10 mmol, 51%) as a yellow oil.

MS m/z ([M+H]) 434.
¹H NMR (300 MHz, CDCl₃): δ (ppm) 0.01 (s, 9H), 0.89-1.06 (m, 2H), 3.35 (dd, J=11.3/2.9 Hz, 1H), 3.64 (d, J=8.2 Hz, 2H), 3.78 (dd, J=11.3/0.7 Hz, 1H), 4.38-4.51 (m, 2H), 4.68 (d, J=2.2 Hz, 1H), 5.29-5.43 (m, 3H), 5.66 (d, J=10.7 Hz, 1H), 5.95 (s, 1H), 5.95-6.08 (m, 1H), 6.99 (d, J=1.3 Hz, 1H), 7.11 (d, J=1.3 Hz, 1H), 8.73 (s, 1H).

Step 20: Preparation of Intermediate trans-10-hydroxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1t)

To a solution of trans-10-allyloxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1s) (43 mg, 0.10 mmol) in anhydrous DCM (2 mL) under inert atmosphere were successively added AcOH (0.01 mL, 0.20 mmol) and Pd(PPh₃)₄ (57 mg, 0.05 mmol). After stirring for 20 min at rt, the mixture was concentrated in vacuo. The residue was purified by flash chromatography on silica gel (DCM/Acetone 80/20 to 0/100) to give trans-10-hydroxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1t) (18 mg, 0.05 mmol, 46%).

MS m/z ([M+H]) 394.
¹H NMR (300 MHz, CDCl₃): δ (ppm) 0.00 (s, 9H), 0.91-1.06 (m, 2H), 1.68 (bs, 1H), 3.34 (dd, J=11.3/3.0 Hz, 1H), 3.64 (dd, J=8.7/8.0 Hz, 2H), 3.74 (d, J=11.2 Hz, 1H), 4.59 (d, J=2.7 Hz, 1H), 5.40 (d, J=10.7 Hz, 1H), 5.68 (d, J=10.7 Hz, 1H), 5.95 (s, 1H), 6.98 (d, J=1.3 Hz, 1H), 7.13 (d, J=1.3 Hz, 1H), 8.74 (s, 1H).

Step 21: Preparation of Sodium {trans-9-oxo-7-[1-(2-trimethylsilylethoxymethyl)-1H-imidazol-2-yl]-3-thia-5,8,10-triaza-tricyclo[6.2.1.0²,⁶]undeca-2(6),4-dien-10-yl}sulfate (1u)

To a solution of trans-10-hydroxy-7-[1-(2-trimethylsilylethoxymethyl)-1H-imidazol-2-yl]-3-thia-5,8,10-triaza-tricyclo[6.2.1.0²,⁶]undeca-2(6),4-dien-9-one (1t) (18 mg, 0.05 mmol) in anhydrous pyridine (0.5 mL) under inert atmosphere was added sulfur trioxide pyridine complex (30 mg, 0.19 mmol). After stirring for 16 h, the heterogeneous mixture was concentrated in vacuo. DCM was added to the residue and the solids were filtered off. The crude residue was applied on a Dowex sodium form column (Dowex® 50WX8 hydrogen form stored with a 2N aqueous NaOH solution and washed until neutral pH with water). The fractions containing the desired compound were combined, freezed and lyophilized. The salt was triturated with DCM and filtered through PTFE filter. The filtrate was eliminated and the solid was solubilized with water MilliQ®. The aqueous layer was freezed and lyophilized to give sodium {trans-9-oxo-7-[1-(2-trimethylsilylethoxymethyl)-1H-imidazol-2-yl]-3-thia-5,8,10-triaza-tricyclo[6.2.1.0$^{2,6}$]undeca-2 (6),4-dien-10-yl}sulfate (1u) (10 mg, 0.02 mmol, 43%) as a white powder.

MS m/z ([M+H]) 474.

$^1$H NMR (400 MHz, D$_2$O): δ (ppm) −0.01 (s, 9H), 0.91-1.08 (m, 2H), 3.59-3.67 (m, 2H), 3.72-3.82 (m, 2H), 5.29 (d, J=1.1 Hz, 1H), 5.59 (d, J=11.0 Hz, 1H), 5.74 (d, J=11.0 Hz, 1H), 6.07 (s, 1H), 6.97 (d, J=1.4 Hz, 1H), 7.41 (d, J=1.4 Hz, 1H), 9.00 (s, 1H).

Step 22: Preparation of Sodium and 2,2,2-trifluoroacetate [trans-7-(1H-imidazol-3-ium-2-yl)-9-oxo-3-thia-5,8,10-triaza-tricyclo[6.2.1.0$^{2,6}$]undeca-2(6),4-dien-10-yl]sulfate (Example 1)

Sodium {trans-9-oxo-7-[1-(2-trimethylsilylethoxymethyl)-1H-imidazol-2-yl]-3-thia-5,8,10-triaza-tricyclo [6.2.1.0$^{2,6}$]undeca-2(6),4-dien-10-yl}sulfate (1u) (10 mg, 0.02 mmol) was dissolved in TFA (0.50 mL, 6.53 mmol) at 0° C. under inert atmosphere. After stirring for 2 h at rt, the mixture was concentrated in vacuo. The residue was triturated several times in Et$_2$O and the filtrate was filtered through PTFE filter. The solid was solubilized with water MilliQ®. The aqueous layer was freezed and lyophilized to give sodium and 2,2,2-trifluoroacetate [trans-7-(1H-imidazol-3-ium-2-yl)-9-oxo-3-thia-5,8,10-triaza-tricyclo[6.2.1.0$^{2,6}$]undeca-2(6),4-dien-10-yl]sulfate (Example 1) (6.0 mg, 0.012 mmol, 62%) as a white solid.

MS m/z ([M+H]) 344.

$^1$H NMR (400 MHz, D$_2$O): δ (ppm) 3.42 (dd, J=12.3/0.7 Hz, 1H), 3.83 (dd, J=12.3/2.9 Hz, 1H), 5.33 (d, J=2.9 Hz, 1H), 6.26 (s, 1H), 7.51 (s, 2H), 9.12 (s, 1H).

Example 2: Synthesis of Sodium [trans-7-(1,3,4-oxadiazol-2-yl)-9-oxo-3-thia-5,8,10-triaza-tricyclo [6.2.1.0$^{2,6}$]undeca-2(6),4-dien-10-yl]sulfate

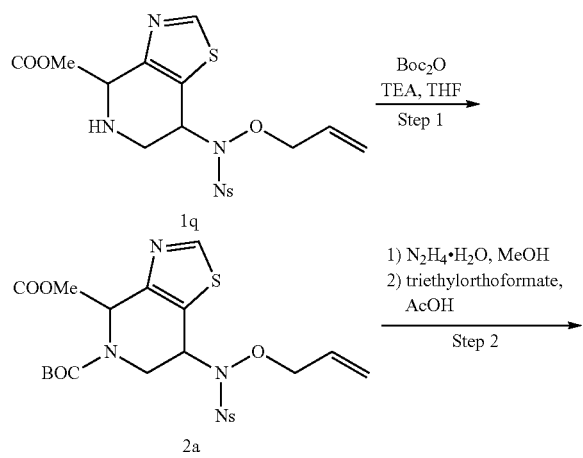

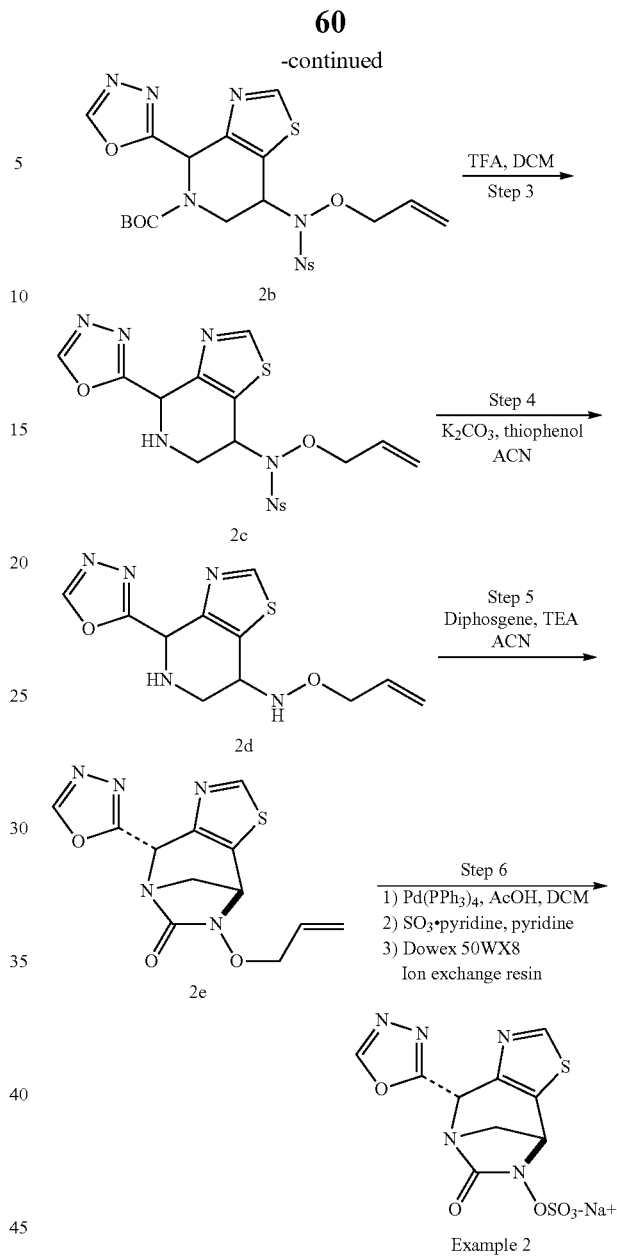

Step 1: Preparation of Intermediate O5-tert-butyl O4-methyl 7-[allyloxy-(2-nitrophenyl)sulfonyl-amino]-6,7-dihydro-4H-thiazolo[4,5-c]pyridine-4,5-dicarboxylate (2a)

To a solution of methyl 7-[allyloxy-(2-nitrophenyl)sulfonyl-amino]-4,5,6,7-tetrahydrothiazolo[4,5-c]pyridine-4-carboxylate (1g) (1.50 g, 3.30 mmol) in anhydrous THF (17 mL) under inert atmosphere at rt were successively added TEA (0.60 mL, 4.29 mmol) and Boc$_2$O (973 mg, 4.46 mmol). The mixture was stirred at 40° C. for 5 h then at rt for 10 h. Water and EtOAc were added. The aqueous layer was extracted with EtOAc twice. The organic layers were combined and dried over Na$_2$SO$_4$ and concentrated in vacuo. The residue was purified by flash chromatography on silica gel (DCM/acetone 100/0 to 90/10) to give O5-tert-butyl O4-methyl 7-[allyloxy-(2-nitrophenyl)sulfonyl-amino]-6,7- dihydro-4H-thiazolo[4,5-c]pyridine-4,5-dicarboxylate (2a) (1.35 g, 2.43 mmol, 74%) as a white solid.

MS m/z ([M+H]) 555.

Step 2: Preparation of Intermediate tert-butyl 7-[allyloxy-(2-nitrophenyl)sulfonyl-amino]-4-(1,3,4-oxadiazol-2-yl)-6,7-dihydro-4H-thiazolo[4,5-c]pyridine-5-carboxylate (2b)

A mixture of O5-tert-butyl O4-methyl 7-[allyloxy-(2-nitrophenyl)sulfonyl-amino]-6,7-dihydro-4H-thiazolo[4,5-c]pyridine-4,5-dicarboxylate (2a) (1.35 g, 2.43 mmol) and hydrazine hydrate (50-60% in water, 0.5 mL) in MeOH (2.5 mL) under inert atmosphere was stirred at rt for 2 days. The mixture was cooled at 0° C. then water and EtOAc were added. The aqueous layer was extracted with EtOAc twice. The organic layers were combined, dried over $Na_2SO_4$ and concentrated in vacuo. The residue was dissolved in triethylorthoformate (12 mL, 73.1 mmol). AcOH (150 µL) was added and the mixture was heated at 110° C. for 20 h. Further AcOH was added at rt and the mixture was heated at 110° C. for further 30 h. The mixture was concentrated in vacuo. The residue was purified by flash chromatography on silica gel (DCM/acetone 100/0 to 90/10) to give tert-butyl 7-[allyloxy-(2-nitrophenyl)sulfonyl-amino]-4-(1,3,4-oxadiazol-2-yl)-6,7-dihydro-4H-thiazolo[4,5-c]pyridine-5-carboxylate (2b) (851 mg, 1.51 mmol, 62%) as a off-white solid.

MS m/z ([M+H]) 565.

Step 3: Preparation of Intermediate N-allyloxy-2-nitro-N-[4-(1,3,4-oxadiazol-2-yl)-4,5,6,7-tetrahydrothiazolo[4,5-c]pyridin-7-yl]benzenesulfonamide (2c)

To a mixture of tert-butyl 7-[allyloxy-(2-nitrophenyl)sulfonyl-amino]-4-(1,3,4-oxadiazol-2-yl)-6,7-dihydro-4H-thiazolo[4,5-c]pyridine-5-carboxylate (2b) (517 mg, 0.92 mmol) in DCM (47 mL) under inert atmosphere, TFA (5.2 mL) was added at rt. The mixture was stirred for 2 h and poured in an ice-cooled 1M aqueous NaOH solution. The aqueous layer was extracted with DCM twice. The organic layers were combined, dried over $Na_2SO_4$ and concentrated in vacuo to give N-allyloxy-2-nitro-N-[4-(1,3,4-oxadiazol-2-yl)-4,5,6,7-tetrahydrothiazolo[4,5-c]pyridin-7-yl]benzenesulfonamide (2c) (401 mg, 0.86 mmol, 94%) as a beige solid which was used without further purification.

MS m/z ([M+H]) 465.

Step 4: Preparation of Intermediate N-allyloxy-4-(1,3,4-oxadiazol-2-yl)-4,5,6,7-tetrahydrothiazolo[4,5-c]pyridin-7-amine (2d)

To a solution of N-allyloxy-2-nitro-N-[4-(1,3,4-oxadiazol-2-yl)-4,5,6,7-tetrahydrothiazolo[4,5-c]pyridin-7-yl]benzenesulfonamide (2c) (401 mg, 0.86 mmol) in ACN (5.4 mL) under inert atmosphere at rt were successively added PhSH (0.36 mL, 3.45 mmol) and potassium carbonate (835 mg, 6.04 mmol). The mixture was stirred at rt for 2 h then filtered through a pad of silica gel, rinsed with DCM to eliminate apolar impurity. Then the product was eluted with a DCM/MeOH (90/10) mixture. The filtrate was concentrated in vacuo. The residue was purified by flash chromatography on silica gel (DCM/acetone 100/0 to 60/40) to give N-allyloxy-4-(1,3,4-oxadiazol-2-yl)-4,5,6,7-tetrahydrothiazolo[4,5-c]pyridin-7-amine (2d) (165 mg, 0.59 mmol, 68%).

MS m/z ([M+H]) 280.

Step 5: Preparation of Intermediate trans-10-allyloxy-7-(1,3,4-oxadiazol-2-yl)-3-thia-5,8,10-triaza-tricyclo[6.2.1.0$^{2,6}$]undeca-2(6),4-dien-9-one (2e)

To a solution of N-allyloxy-4-(1,3,4-oxadiazol-2-yl)-4,5,6,7-tetrahydrothiazolo[4,5-c]pyridin-7-amine (2d) (165 mg, 0.59 mmol) in ACN (60 mL) under inert atmosphere at −10° C. was added TEA (0.37 mL, 2.66 mmol). A solution of diphosgene (39 µL, 0.33 mmol) in ACN (1.1 mL) was dropwisely added. After stirring for 2 h at −10° C., the mixture was stirred at rt for 20 h. The solvent was evaporated. The residue was diluted in DCM, washed with a 2M aqueous solution of $NaH_2PO_4$. The organic layers were combined, dried over $Na_2SO_4$ and concentrated in vacuo. The residue was purified by flash chromatography on silica gel (DCM/acetone 100/0 to 80/20) to give trans-10-allyloxy-7-(1,3,4-oxadiazol-2-yl)-3-thia-5,8,10-triaza-tricyclo[6.2.1.0$^{2,6}$]undeca-2(6),4-dien-9-one (2e) (64 mg, 0.21 mmol, 36%) as a white solid.

MS m/z ([M+H]) 306.

$^1$H NMR (300 MHz, CDCl$_3$): δ (ppm) 3.60 (dd, J=11.7/2.8 Hz, 1H), 3.76 (dd, J=11.7/0.7 Hz, 1H), 4.40-4.54 (m, 2H), 4.75 (dd, J=2.8/0.7 Hz, 1H), 5.32-5.41 (m, 2H), 5.94-6.09 (m, 2H), 8.52 (s, 1H), 8.75 (s, 1H).

Step 6: Preparation of Sodium [trans-7-(1,3,4-oxadiazol-2-yl)-9-oxo-3-thia-5,8,10-triaza-tricyclo[6.2.1.0$^{2,6}$]undeca-2(6),4-dien-10-yl]sulfate (Example 2)

To a solution of trans-10-allyloxy-7-(1,3,4-oxadiazol-2-yl)-3-thia-5,8,10-triaza-tricyclo[6.2.1.0$^{2,6}$]undeca-2(6),4-dien-9-one (2e) (58 mg, 0.19 mmol) in anhydrous DCM (4.2 mL) under inert atmosphere were successively added AcOH (21 µL, 0.37 mmol) and Pd(PPh$_3$)$_4$ (108 mg, 0.09 mmol). After stirring at rt for 1 h, the mixture was diluted with pyridine (1.1 mL) and sulfur trioxide-pyridine complex (120 mg, 0.76 mmol) was added. The mixture was stirred at rt for 5 h in the dark and then concentrated in vacuo. DCM was added to the residue and the solids were filtered off. The filtrate was concentrated in vacuo and the residue was applied on a Dowex sodium form column (Dowex® 50WX8 hydrogen form stored with a 2N aqueous NaOH solution and washed until neutral pH with water). The fractions containing the desired compound were combined, freezed and lyophilized. The residue was purified by flash chromatography on C18 silica gel (water/ACN 98/2) to give sodium [trans-7-(1,3,4-oxadiazol-2-yl)-9-oxo-3-thia-5,8,10-triaza-tricyclo[6.2.1.0$^{2,6}$]undeca-2(6),4-dien-10-yl]sulfate (Example 2) (4.0 mg, 0.006 mmol, 3%) as an off-white powder.

MS m/z ([M+H]) 346.

MS m/z ([M+H]) 344.

$^1$H NMR (400 MHz, D$_2$O): δ (ppm) 3.10 (dd, J=14.5/2.5 Hz, 1H), 3.35 (dd, J=14.5/4.0 Hz, 1H), 5.30 (d, J=2.5 Hz, 1H), 5.70 (s, 1H), 8.92 (s, 1H), 8.98 (s, 1H).

63
Example 3: Synthesis of Sodium and 2,2,2-trifluoroacetate [trans-7-(4H-1,2,4-triazol-4-ium-3-yl)-9-oxo-3-thia-5,8,10-triaza-tricyclo[6.2.1.0²,⁶]undeca-2(6),4-dien-10-yl]sulfate
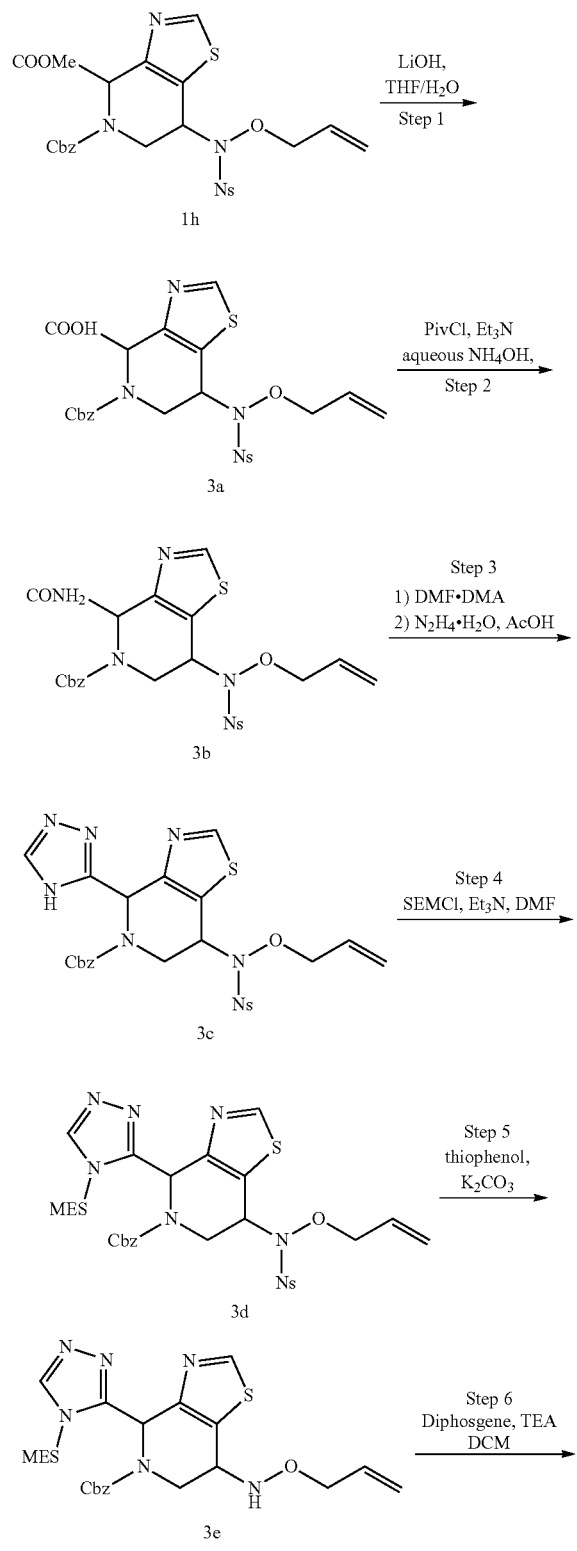
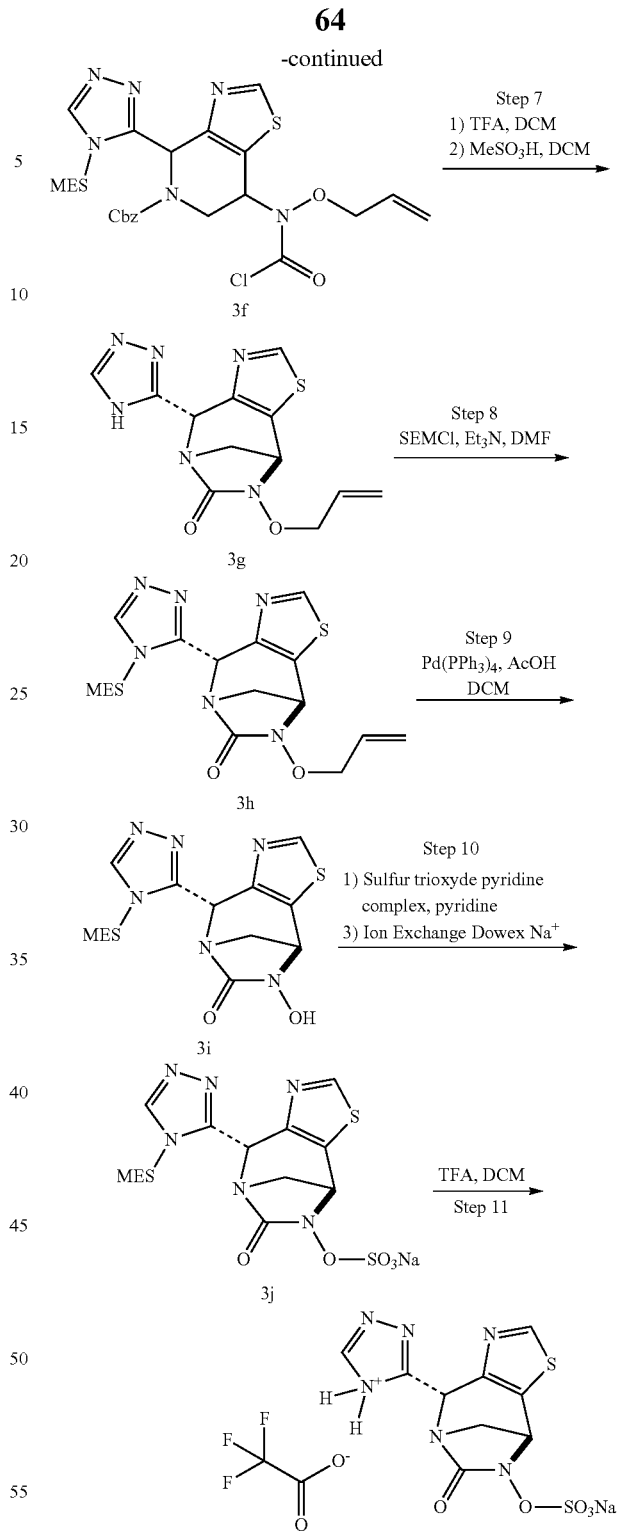
Step 1: Preparation of Intermediate O5-benzyl 7-[allyloxy-(2-nitrophenyl)sulfonyl-amino]-6,7-dihydro-4H-thiazolo[4,5-c]pyridine-4,5-dicarboxylate (3a)
To a solution of O5-benzyl O4-methyl 7-[allyloxy-(2-nitrophenyl)sulfonyl-amino]-6,7-dihydro-4H-thiazolo[4,5- c]pyridine-4,5-dicarboxylate (1h) (2.03 g, 3.44 mmol) in a mixture of THF (21 mL) and water (14 mL) at rt was dropwise added a solution of lithium hydroxide 1N (4.1 mL, 4.13 mmol). After stirring for 30 min, the mixture was diluted with DCM and acidified to pH 1 with a solution of HCl 1N at rt. The product was extracted with DCM and concentrated in vacuo to give O5-benzyl 7-[allyloxy-(2-nitrophenyl)sulfonyl-amino]-6,7-dihydro-4H-thiazolo[4,5-c]pyridine-4,5-dicarboxylate (3a) (1.98 g, 3.44 mmol, quantitative yield) as a white foam which was used without further purification.

MS m/z ([M+H]) 575.

Step 2: Preparation of Intermediate O5-benzyl 7-[allyloxy-(2-nitrophenyl)sulfonyl-amino]-6,7-dihydro-4H-thiazolo[4,5-c]pyridine-4-carboxamide-5-carboxylate (3b)

To a solution of O5-benzyl 7-[allyloxy-(2-nitrophenyl)sulfonyl-amino]-6,7-dihydro-4H-thiazolo[4,5-c]pyridine-4,5-dicarboxylate (3a) (1.98 g, 3.44 mmol) in anhydrous DCM (17 mL) under inert atmosphere at 0° C. were sequentially added TEA (0.58 mL, 4.13 mmol) and trimethylacetyl chloride (0.45 mL, 3.62 mmol) and the mixture was stirred at 0° C. for 45 min. Then the mixture was cooled down to −20° C. and ammonium hydroxide solution 28-30% (0.57 mL, 13.78 mmol) was dropewisely added. The reacting mixture was stirred at −20° C. for 30 min before being diluted with DCM (5.0 mL) and water (2.0 mL), warmed up to rt, extracted with DCM and concentrated in vacuo to give O5-benzyl 7-[allyloxy-(2-nitrophenyl)sulfonyl-amino]-6,7-dihydro-4H-thiazolo[4,5-c]pyridine-4-carboxamide-5-carboxylate (3b) (1.98 g, 3.44 mmol, quantitative yield) as a brown foam which was used without further purification.

MS m/z ([M+H]) 574.

Step 3: Preparation of Intermediate O5-benzyl 7-[allyloxy-(2-nitrophenyl)sulfonyl-amino]-6,7-dihydro-4H-thiazolo[4,5-c]pyridine-4-(NH-1,2,4-triazol-3-yl)-5-carboxylate (3c)

A solution of O5-benzyl 7-[allyloxy-(2-nitrophenyl)sulfonyl-amino]-6,7-dihydro-4H-thiazolo[4,5-c]pyridine-4-carboxamide-5-carboxylate (3b) (1.98 g, 3.44 mmol) in N,N-dimethylformamide dimethyl acetal (9.2 mL, 68.90 mmol) was stirred at 90° C. for 30 min then cooled down to rt and concentrated under reduced pressure. The residue was dissolved in AcOH (17 mL) and hydrazine hydrate (1.07 mL, 34.45 mmol) was carefully added. The mixture was stirred at 80° C. for 20 min then cooled down to rt and concentrated under reduced pressure. The residue was purified by flash chromatography on silica gel (DCM/acetone 50/50) to give O5-benzyl 7-[allyloxy-(2-nitrophenyl)sulfonyl-amino]-6,7-dihydro-4H-thiazolo[4,5-c]pyridine-4-(NH-1,2,4-triazol-3-yl)-5-carboxylate (3c) (3.31 g contaminated by salts) as a brown oil.

MS m/z ([M+H]) 598.
MS m/z ([M−H]) 596.

Step 4: Preparation of Intermediate O5-benzyl 7-[allyloxy-(2-nitrophenyl)sulfonyl-amino]-6,7-dihydro-4H-thiazolo[4,5-c]pyridine-4-(N-(2-trimethylsilylethoxymethyl)-1,2,4-triazol-3-yl)-5-carboxylate (3d)

To a solution of O5-benzyl 7-[allyloxy-(2-nitrophenyl)sulfonyl-amino]-6,7-dihydro-4H-thiazolo[4,5-c]pyridine-4-(NH-1,2,4-triazol-3-yl)-5-carboxylate (3c) (3.31 g, 3.44 mmol in theory) in anhydrous DMF (22 mL) under inert atmosphere were successively added (2-(chloromethoxy)ethyl)trimethylsilane (14.7 mL, 83.08 mmol) and TEA (15.4 mL, 110.78 mmol). After stirring at rt for 30 min, the mixture was concentrated in vacuo. The residue was dissolved in DCM, washed with brine, concentrated in vacuo and then purified by flash chromatography on silica gel (DCM/Acetone 100/0 to 70/30) to give O5-benzyl 7-[allyloxy-(2-nitrophenyl)sulfonyl-amino]-6,7-dihydro-4H-thiazolo[4,5-c]pyridine-4-[N-(2-trimethylsilylethoxymethyl)-1,2,4-triazol-3-yl]-5-carboxylate (3d) (2.70 g contaminated by salts) as a brown oil.

MS m/z ([M+H]) 728.
MS m/z ([M−H]) 726.

Step 5: Preparation of Intermediate O5-benzyl 7-(allyloxyamino)-6,7-dihydro-4H-thiazolo[4,5-c]pyridine-4-[N-(2-trimethylsilylethoxymethyl)-1,2,4-triazol-3-yl]-5-carboxylate To a solution of O5-benzyl 7-[allyloxy-(2-nitrophenyl)sulfonyl-amino]-6,7-dihydro-4H-thiazolo[4,5-c]pyridine-4-[N-(2-trimethylsilylethoxymethyl)-1,2,4-triazol-3-yl]-5-carboxylate (3d) (2.70 g, 3.44 mmol in theory) in ACN (17 mL) under inert atmosphere at rt were successively added potassium carbonate (2.38 g, 17.22 mmol) and PhSH (1.77 mL, 17.22 mmol). The mixture was stirred at rt for 2 h then filtered through a fritté, rinsed with DCM and the filtrate was concentrated under reduced pressure. The residue was purified by flash chromatography on silica gel (DCM/acetone 100/0 to 70/30) to give O5-benzyl 7-(allyloxyamino)-6,7-dihydro-4H-thiazolo[4,5-c]pyridine-4-[N-(2-trimethylsilylethoxymethyl)-1,2,4-triazol-3-yl]-5-carboxylate (3e) (1.39 g, 2.57 mmol, 75% over 6 steps) as a yellow oil.

MS m/z ([M+H]) 543.

Step 6: Preparation of Intermediate O5-benzyl 7-[allyloxy(chlorocarbonyl)amino]-6,7-dihydro-4H-thiazolo[4,5-c]pyridine-4-[N-(2-trimethylsilylethoxymethyl)-1,2,4-triazol-3-yl]-5-carboxylate (3f)

To a solution of O5-benzyl 7-(allyloxyamino)-6,7-dihydro-4H-thiazolo[4,5-c]pyridine-4-[N-(2-trimethylsilylethoxymethyl)-1,2,4-triazol-3-yl]-5-carboxylate (3e) (1.39 g, 2.57 mmol) in DCM (26 mL) under inert atmosphere at 0° C. were dropwisely added TEA (0.72 mL, 5.13 mmol) and diphosgene (0.40 mL, 3.38 mmol). After stirring at 0° C. for 30 min, the mixture was diluted with DCM, washed with brine and concentrated under reduced pressure to give O5-benzyl 7-[allyloxy(chlorocarbonyl)amino]-6,7-dihydro-4H-thiazolo[4,5-c]pyridine-4-[N-(2-trimethylsilylethoxymethyl)-1,2,4-triazol-3-yl]-5-carboxylate (3f) (1.55 g, 2.57 mmol, quantitative yield) as a brown oil.

MS m/z ([M+H]) 605 ($^{39}$Cl)/607 ($^{41}$Cl).

Step 7: Preparation of Intermediate trans-10-allyloxy-7-(NH-1,2,4-triazol-3-yl)-3-thia-5,8,10-triazatricyclo[6.2.1.0$^{2,6}$]undeca-2(6),4-dien-9-one (3g)

To a solution of O5-benzyl 7-[allyloxy(chlorocarbonyl)amino]-6,7-dihydro-4H-thiazolo[4,5-c]pyridine-4-[N-(2-trimethylsilylethoxymethyl)-1,2,4-triazol-3-yl]-5-carboxylate (3f) (1.55 g, 2.57 mmol) in anhydrous DCM (13 mL) under inert atmosphere at rt was dropwisely added TFA (12.8 mL, 167.68 mmol). After stirring at rt for 2 h, the reaction mixture was cooled down to 0° C. and a solution of methanesufonic acid (3.33 mL, 51.34 mmol) in DCM (26 mL) was dropewisely added. The mixture was stirred at 0° C. for 24 h, then diluted with DCM (20 mL), carefully added to a solution of TEA (18 mL) in DCM (100 mL) at 0° C., warmed up to rt and stirred for additional 20 min. The mixture was filtered through a pad of Celite® and concentrated in vacuo. The residue was purified by flash chromatography on silica gel (DCM/acetone 50/50 to 0/100) to give trans-10-allyloxy-7-(NH-1,2,4-triazol-3-yl)-3-thia-5,8,10-triaza-tricyclo[6.2.1.0$^{2,6}$]undeca-2(6),4-dien-9-one (3g) (781 mg polluted by a non-UV visible impurity) as a yellow oil.

MS m/z ([M+H]) 305.
MS m/z ([M−H]) 303.

Step 8: Preparation of Intermediate trans-10-allyloxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3h)

To a solution of trans-10-allyloxy-7-(NH-1,2,4-triazol-3-yl)-3-thia-5,8,10-triaza-tricyclo[6.2.1.0$^{2,6}$]undeca-2(6),4-dien-9-one (3g) (781 mg, 2.57 mmol in theory) in anhydrous DMF (5.1 mL) under inert atmosphere at 0° C. were successively added (2-(chloromethoxy)ethyl)trimethylsilane (1.1 mL, 6.42 mmol) and TEA (1.8 mL, 12.83 mmol). After stirring at rt for 17 h, the mixture was concentrated in vacuo. The residue was dissolved in DCM, washed with brine, concentrated in vacuo and then purified by flash chromatography on silica gel (DCM/Acetone 100/0 to 50/50) to give trans-10-allyloxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3h) (117 mg, 0.27 mmol, 10% over 2 steps) as a brown oil.

MS m/z ([M+H]) 435.

Step 9: Preparation of Intermediate trans-10-hydroxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3i)

To a solution of trans-10-allyloxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3h) (117 mg, 0.27 mmol) in anhydrous DCM (2.7 mL) under inert atmosphere at rt were successively added AcOH (0.03 mL, 0.54 mmol) and Pd(PPh$_3$)$_4$ (155 mg, 0.14 mmol). After stirring for at rt 30 min, the mixture was concentrated in vacuo. The residue was purified by flash chromatography on silica gel (DCM/Acetone 80/20 to 0/100) to give trans-10-hydroxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3i) (43 mg, 0.11 mmol, 41%) as a yellow foam.

MS m/z ([M+H]) 395.

Step 10: Preparation of Intermediate Sodium {trans-9-oxo-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-10-yl}sulfate (3j)

To a solution of trans-10-hydroxy-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-9-one (3i) (43 mg, 0.11 mmol) in anhydrous pyridine (1.1 mL) under inert atmosphere at rt was added sulfur trioxide pyridine complex (87 mg, 0.55 mmol). After stirring at rt for 17 h, the heterogeneous mixture was concentrated in vacuo. DCM was added to the residue, the solids were filtered off and the filtrate was concentrated in vacuo. The crude residue was applied on a Dowex sodium form column (Dowex® 50WX8 hydrogen form stored with an aqueous solution of 2N NaOH and washed until neutral pH with water). The fractions containing the desired compound were combined, freezed and lyophilized. The salt was triturated with DCM and filtered through PTFE filter. The filtrate was eliminated and the solid was solubilized with water MilliQ®. The aqueous layer was freezed and lyophilized to give sodium {trans-9-oxo-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-10-yl}sulfate (3j) (28 mg, 0.06 mmol, 52%) as a light-brown powder.

MS m/z ([M+H]) 475.
MS m/z ([M−H]) 473.

Step 11: Preparation of Intermediate Sodium and 2,2,2-trifluoroacetate [trans-7-(NH-1,2,4-triazol-4-ium-3-yl)-9-oxo-3-thia-5,8,10-triaza-tricyclo[6.2.1.0$^{2,6}$]undeca-2(6),4-dien-10-yl]sulfate (Example 3)

Sodium {trans-9-oxo-7-[N-(2-trimethylsilylethoxymethyl)-1,2,4-triazol-3-yl]-3-thia-5,8,10-triaza-tricyclo[6.2.1.0$^{2,6}$]undeca-2(6),4-dien-10-yl}sulfate (3j) (28 mg, 0.06 mmol) was dissolved in anhydrous DCM (0.28 mL) and TFA (0.28 mL, 3.65 mmol) was dropewisely added at 0° C. under inert atmosphere. After stirring for 1 h at rt, the mixture was diluted in DCM (1.0 mL) and concentrated in vacuo. The residue was triturated several times in Et$_2$O then in ACN and the filtrate was filtered through PTFE filter. The solid was solubilized with water MilliQ®. The aqueous layer was freezed and lyophilized to give sodium and 2,2,2-trifluoroacetate [trans-7-(NH-1,2,4-triazol-4-ium-3-yl)-9-oxo-3-thia-5,8,10-triaza-tricyclo[6.2.1.0$^{2,6}$]undeca-2(6),4-dien-10-yl]sulfate (Example 3) (10 mg, 0.021 mmol, 35%) as a beige solid.

MS m/z ([M+H]) 345.
MS m/z ([M−H]) 343.
$^1$H NMR (300 MHz, D$_2$O): δ (ppm) 3.62-3.70 (m, 2H), 5.27-5.32 (m, 1H), 5.97 (s, 1H), 8.51 (s, 1H), 9.00 (s, 1H).
$^{19}$F NMR (282 MHz, D$_2$O): δ (ppm) −75.57 (s, 3F).

Example 4: Synthesis of Sodium [trans-7-(1,2,4-oxadiazol-5-yl)-9-oxo-3-thia-5,8,10-triaza-tricyclo[6.2.1.0$^{2,6}$]undeca-2(6),4-dien-10-yl]sulfate

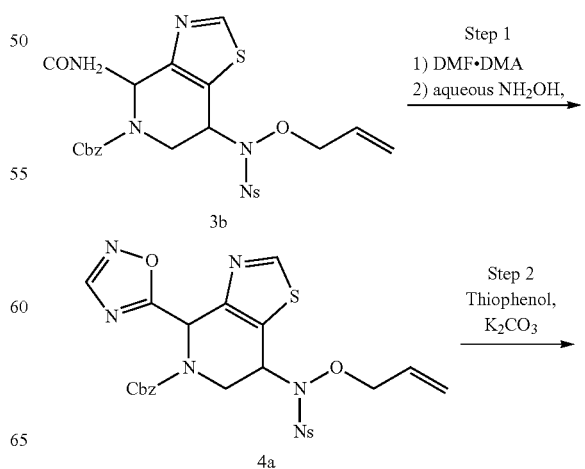

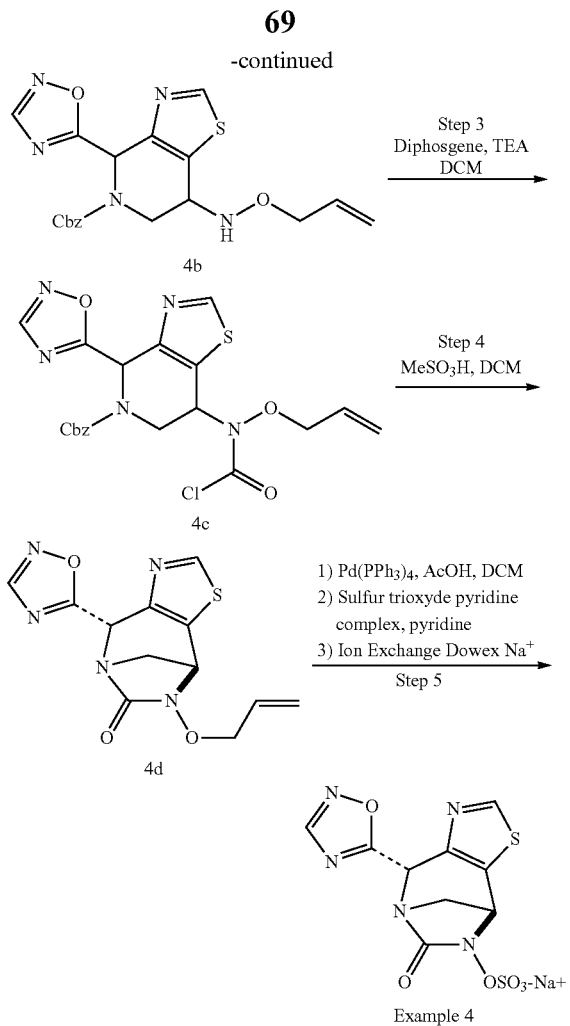

Step 2: Preparation of Intermediate O5-benzyl 7-[allyloxyamino]-6,7-dihydro-4H-thiazolo[4,5-c]pyridine-4-(1,2,4-oxadiazol-5-yl)-5-carboxylate (4b)

To a solution of O5-benzyl 7-[allyloxy-(2-nitrophenyl) sulfonyl-amino]-6,7-dihydro-4H-thiazolo[4,5-c]pyridine-4-(1,2,4-oxadiazol-5-yl)-5-carboxylate (4a) (1.66 g, 2.78 mmol) in ACN (28 mL) under inert atmosphere at rt were successively added potassium carbonate (1.92 g, 13.88 mmol) and PhSH (0.86 mL, 8.33 mmol). The mixture was stirred at rt for 1 h then filtered through a fritté, rinsed with DCM and the filtrate was concentrated under reduced pressure. The residue was purified by flash chromatography on silica gel (DCM/acetone 90/10) to give O5-benzyl 7-(allyloxyamino)-6,7-dihydro-4H-thiazolo[4,5-c]pyridine-4-(1,2,4-oxadiazol-5-yl)-5-carboxylate (4b) (805 mg, 1.95 mmol, 70%) as a light-yellow oil.

MS m/z ([M+H]) 414.

MS m/z ([M−H]) 412.

Step 3: Preparation of Intermediate O5-benzyl 7-[allyloxy(chlorocarbonyl)amino]-6,7-dihydro-4H-thiazolo[4,5-c]pyridine-4-(1,2,4-oxadiazol-5-yl)-5-carboxylate (4c)

To a solution of O5-benzyl 7-(allyloxyamino)-6,7-dihydro-4H-thiazolo[4,5-c]pyridine-4-(1,2,4-oxadiazol-5-yl)-5-carboxylate (4b) (805 mg, 1.95 mmol) in DCM (20 mL) under inert atmosphere at 0° C. were dropwisely added TEA (0.54 mL, 3.89 mmol) and diphosgene (0.31 mL, 2.53 mmol). After stirring at 0° C. for 30 min, the mixture was diluted with DCM, washed with brine and concentrated under reduced pressure to give O5-benzyl 7-[allyloxy(chlorocarbonyl)amino]-6,7-dihydro-4H-thiazolo[4,5-c]pyridine-4-(1,2,4-oxadiazol-5-yl)-5-carboxylate (4c) (930 mg, 1.95 mmol, quantitative yield) as a brown oil.

MS m/z ([M+H]) 476.

Step 4: Preparation of Intermediate trans-10-allyloxy-7-(1,2,4-oxadiazol-5-yl)-3-thia-5,8,10-triaza-tricyclo[6.2.1.0$^{2,6}$]undeca-2(6),4-dien-9-one (4d)

To a solution of O5-benzyl 7-[allyloxy(chlorocarbonyl)amino]-6,7-dihydro-4H-thiazolo[4,5-c]pyridine-4-(1,2,4-oxadiazol-5-yl)-5-carboxylate (4c) (930 mg, 1.95 mmol) in anhydrous DCM (20 mL) under inert atmosphere at 0° C. was dropwisely added methanesulfonic acid (2.53 mL, 38.94 mmol). After stirring at 0° C. for 24 h, the reaction mixture was diluted with DCM, carefully added to a solution of pyridine (8.0 mL) in DCM (8.0 mL) at 0° C., warmed up to rt and stirred for additional 10 min. The mixture was filtered through a pad of Celite® and concentrated in vacuo. The residue was purified by flash chromatography on silica gel (DCM/acetone 90/10) to give trans-O-allyloxy-7-(1,2,4-oxadiazol-5-yl)-3-thia-5,8,10-triaza-tricyclo[6.2.1.0$^{2,6}$]undeca-2(6),4-dien-9-one (4d) (318 mg, 1.04 mmol, 54%) as a yellow oil.

MS m/z ([M+H]) 306.

MS m/z ([M+H]) 304.

$^1$H NMR (400 MHz, CDCl$_3$): δ (ppm) 3.65 (dd, J=12.0/4.0 Hz, 1H), 3.74 (d, J=12.0 Hz, 1H), 4.42-4.53 (m, 2H), 4.75 (d, J=2.8 Hz, 1H), 5.33-5.36 (m, 1H), 5.36-5.42 (m, 1H), 5.97-6.07 (m, 1H), 6.11 (s, 1H), 8.44 (s, 1H), 8.75 (s, 1H).

Step 1: Preparation of Intermediate O5-benzyl 7-[allyloxy-(2-nitrophenyl)sulfonyl-amino]-6,7-dihydro-4H-thiazolo[4,5-c]pyridine-4-(1,2,4-oxadiazol-5-yl)-5-carboxylate (4a)

A solution of O5-benzyl 7-[allyloxy-(2-nitrophenyl)sulfonyl-amino]-6,7-dihydro-4H-thiazolo[4,5-c]pyridine-4-carboxamide-5-carboxylate (3b) (2.60 g, 4.53 mmol) in N,N-dimethylformamide dimethyl acetal (12.0 mL, 90.66 mmol) was stirred at 90° C. for 30 min then cooled down to rt and concentrated under reduced pressure. The residue was dissolved in AcOH (23 mL) and a commercial hydroxylamine solution 50 wt. % in H$_2$O (2.78 mL, 45.33 mmol) was carefully added. The mixture was stirred at 90° C. for 30 min then cooled down to rt and concentrated under reduced pressure. The residue was partitioned between DCM and water, extracted with DCM and concentrated under reduced pressure. The residue was purified by flash chromatography on silica gel (DCM/acetone 80/20) to give O5-benzyl 7-[allyloxy-(2-nitrophenyl)sulfonyl-amino]-6,7-dihydro-4H-thiazolo[4,5-c]pyridine-4-(1,2,4-oxadiazol-5-yl)-5-carboxylate (4a) (1.66 g, 2.78 mmol, 61% over two steps) as a light-yellow foam.

MS m/z ([M+H]) 599.

MS m/z ([M−H]) 597.

Step 5: Preparation of Sodium [trans-7-(1,2,4-oxadiazol-5-yl)-9-oxo-3-thia-5,8,10-triaza-tricyclo[6.2.1.0$^{2,6}$]undeca-2(6),4-dien-10-yl]sulfate (Example 4)

To a solution of trans-10-allyloxy-7-(1,2,4-oxadiazol-5-yl)-3-thia-5,8,10-triaza-tricyclo[6.2.1.0$^{2,6}$]undeca-2(6),4-dien-9-one (4d) (111 mg, 0.36 mmol) in anhydrous DCM (3.6 mL) under inert atmosphere were successively added AcOH (0.04 mL, 0.73 mmol) and Pd(PPh$_3$)$_4$ (210 mg, 0.18 mmol). After stirring at rt for 1 h, the mixture was diluted with anhydrous pyridine (3.6 mL) and sulfur trioxide pyridine complex (289 mg, 1.82 mmol) was added in one portion. After stirring at rt for 48 h, the heterogeneous mixture was concentrated in vacuo. The residue was diluted with DCM, the solids were filtered off and the filtrate was concentrated in vacuo. The residue was purified by flash chromatography on silica gel (DCM/acetone 70/30 to 100% acetone) and, after concentration in vacuo, the obtained light-yellow foam residue was applied on a Dowex sodium form column (Dowex® 50WX8 hydrogen form stored with an aqueous solution of 2N NaOH and washed until neutral pH with water). The fractions containing the desired compound were combined, freezed and lyophilized. The salt was triturated with DCM and filtered through PTFE filter. The filtrate was eliminated and the solid was solubilized with water MilliQ®. The aqueous layer was freezed and lyophilized to give sodium [trans-7-(1,2,4-oxadiazol-5-yl)-9-oxo-3-thia-5,8,10-triaza-tricyclo[6.2.1.0$^{2,6}$]undeca-2(6),4-dien-10-yl]sulfate (Example 4) (14.5 mg, 0.04 mmol, 11%) as a white powder.

MS m/z ([M+H]) 346.
MS m/z ([M+H]) 344.
$^1$H NMR (400 MHz, D$_2$O): δ (ppm) 3.67 (d, J=12.0 Hz, 1H), 3.86 (dd, J=12.0/4.0 Hz, 1H), 5.33 (d, J=3.0 Hz, 1H), 6.03 (s, 1H), 8.79 (s, 1H), 9.06 (s, 1H).

Example 5: Biological Activity

Method 1: β-Lactamase Inhibitory Activity, Determination of IC$_{50}$ (Table 1)

Enzyme activity was monitored by spectrophotometric measurement of nitrocefin (NCF-TOKU-E, N005) hydrolysis at 485 nm, at room temperature and in assay buffer A: 100 mM Phosphate pH7, 2% glycerol and 0.1 mg/mL Bovine serum albumin (Sigma, B4287). Enzymes were cloned in E. coli expression vector, expressed and purified in house using classical procedures. To a transparent polystyrene plate (Corning, 3628) were added in each well 5 µL DMSO or inhibitor dilutions in DMSO and 80 µL enzyme in buffer A. Plates were immediately read at 485 nm in a microplate spectrophotometer (BioTek, PowerWave HT) to enable background subtraction. After 30 min of pre-incubation at room temperature, 15 µL of NCF (200 µM final) were finally added in each well. Final enzyme concentrations were 0.1 nM (TEM-1), 0.075 nM (SHV-1), 0.4 nM (CTX-M-15), 1 nM (KPC-2), 0.2 nM (P99 AmpC), 0.2 nM (CMY-37), 0.4 nM (AmpC P. aeruginosa), 0.2 nM (OXA-1), 1.2 nM (OXA-11), 0.4 nM (OXA-15) and 0.3 nM (OXA-48). After 20 min incubation at room temperature, plates were once again read at 485 nm. Enzyme activity was obtained by subtracting the final signal by the background, and was converted to enzyme inhibition using non inhibited wells. IC$_{50}$ curves were fitted to a classical Langmuir equilibrium model with Hill slope using XLFIT (IDBS).

TABLE 1

IC$_{50}$ (nM) for β-lactamase Inhibitory Activity

| | IC$_{50}$ β-lactamase (µM) | | | | | | | | | | |
|---|---|---|---|---|---|---|---|---|---|---|---|
| | (A) | | | | (C) | | | (D) | | | |
| | TEM-1 | SHV-1 | CTX-M-15 | KPC-2 | AmpC (P99) | CMY-37 | AmpC (PAE) | OXA-1 | OXA-11 | OXA-15 | OXA-48 |
| Example 1 | 0.012 | 0.0055 | 0.0027 | 0.0042 | 0.00037 | 0.00063 | 0.017 | 0.19 | 0.41 | 0.27 | 0.0084 |
| Example 3 | 0.046 | 0.14 | 0.028 | 0.46 | 0.013 | 0.030 | 0.57 | 1.0 | 0.19 | 1.1 | 0.0068 |
| Example 4 | 0.0011 | 0.0014 | 0.00064 | 0.0032 | 0.0011 | 0.0034 | 0.064 | 0.17 | 0.0065 | 0.019 | 0.00034 |

Method 2: MIC of Compounds and Synergy with Ceftazidime Against Bacterial Isolates (Table 2 and 3)

Compounds of the present invention were assessed against genotyped bacterial strains alone or in combination with the β-lactam ceftazidime. In the assays, MICs of said compounds, or of ceftazidime at fixed concentrations of said compounds were determined by the broth microdilution method according to the Clinical Laboratory Standards Institute (CLSI—M7-A7). Briefly, compounds alone according to the invention were prepared in DMSO and spotted (2 µL each) on sterile polystyrene plates (Corning, 3788). Compounds and ceftazidime dilutions were prepared in DMSO and spotted (1 µL each) on sterile polystyrene plates (Corning, 3788). Log phase bacterial suspensions were adjusted to a final density of 5×10$^5$ cfu/mL in cation-adjusted Mueller-Hinton broth (Beckton-Dickinson) and added to each well (98 µL). Microplates were incubated for 16-20 h at 35° C. in ambient air. The MIC of of the compounds was defined as the lowest concentration of said compounds that prevented bacterial growth as read by visual inspection. The MIC of ceftazidime at each compound concentration was defined as the lowest concentration of ceftazidime that prevented bacterial growth as read by visual inspection.

TABLE 2

Bacterial species used in MIC determination

| | |
|---|---|
| CFR | C. freundii |
| CMU | C. murliniae |
| EAE | E. aerogenes |
| ECL | E. cloacae |
| ECO | E. coli |
| KOX | K. oxytoca |
| KPN | K. pneumoniae |
| MMO | M. morganii |
| PAE | P. aeruginosa |
| PMI | P. mirabilis |
| SMA | S. marcescens |

TABLE 3

MIC of compounds and Ceftazidime/compound combinations

| | Strain | beta-lactamases | CAZ | Example 1 | CAZ + Example 1 (4 µg/mL) | Example 3 | CAZ + Example 3 (4 µg/mL) | Example 4 | CAZ + Example 4 (4 µg/mL) |
|---|---|---|---|---|---|---|---|---|---|
| ECO | 190317 | TEM-1, SHV-12, CTX-M-15 OXA-1 | 128 | 1 | <0.25 | 16 | 32 | 16 | 0.25 |
| ECO | 180070 | TEM-1, CTX-M-15 | 64 | 1 | <0.25 | | | | |
| ECO | 190314 | CTX-M-1 | 8 | 0.5 | <0.25 | | | | |
| ECO | 190457 | CTX-M-15 OXA-1 | 16 | 1 | <0.25 | | | | |
| ECO | 190549 | CTX-M-1 | 8 | 0.25 | <0.25 | | | | |
| ECO | 200159 | TEM-1, CTX-M-14 | 2 | 0.25 | <0.25 | | | | |
| ECO | 200259 | CTX-M-14 | 4 | 0.5 | <0.25 | | | | |
| ECO | 200344 | CTX-M-1 | 16 | 0.5 | <0.25 | | | | |
| ECO | 260096 | CTX-M-132 | 128 | 4 | <0.25 | | | | |
| ECO | 260304 | CTX-M-15 | 16 | 1 | <0.25 | | | | |
| ECO | 260508 | TEM-1, CTX-M-15 OXA-1 | 128 | 2 | <0.25 | | | | |
| ECO | UFR16 | TEM-1, CTX-M-15 OXA-1 OXA-48 | 64 | 2 | <0.25 | | | | |
| ECO | UFR17 | TEM-1, CTX-M-15 CMY-2 OXA-1 OXA-181 | >128 | 4 | <0.25 | | | | |
| ECO | UFR18 | CTX-M-15 OXA-204 | >128 | 1 | <0.25 | | | | |
| ECO | UFR19 | CTX-M-15 CMY-2 OXA-1 OXA-204 | 128 | 1 | <0.25 | | | | |
| ECO | UFR32 | TEM-1, VEB-1 OXA-10 | >128 | 1 | <0.25 | | | | |
| ECO | UFR39 | CTX-M-15 NDM-1 | >128 | 2 | <0.25 | | | | |
| ECO | UFR41 | TEM-1, CTX-M-15 CMY-2 OXA-1 NDM-4 | >128 | 16 | >128 | | | | |
| ECO | UFR45 | TEM-1 CMY-4 OXA-1 OXA-48 VIM-1 | 2 | 0.5 | <0.25 | | | | |
| ECO | UFR52 | TEM-1, SHV-12 IMP-8 | >128 | 1 | <0.25 | | | | |
| ECO | UFR61O | TEM-1 KPC-2 | 128 | 1 | <0.25 | | | | |
| ECO | UFR62 | TEM-1, CTX-M-9 KPC-2 | 16 | 0.5 | <0.25 | | | | |
| ECO | UFR74 | SHV-1 DHA-1 | 128 | 2 | <0.25 | | | | |
| ECO | UFR86 | | 2 | 2 | <0.25 | | | | |
| ECL | P99 | AmpC | 128 | 4 | <0.25 | | | 32 | 2 |
| EAE | 200261 | TEM-x AmpC | 128 | 8 | <0.25 | | | | |
| ECL | NEM146383 | AmpC | >128 | 2 | <0.25 | | | | |
| ECL | 190310 | AmpC | >128 | 4 | <0.25 | | | | |
| ECL | 190408 | TEM-1, CTX-M-15 OXA-1 | 128 | 0.5 | <0.25 | | | | |
| ECL | 200138 | AmpC | >128 | 8 | 8 | | | | |
| ECL | 200322 | TEM-1, CTX-M-15 OXA-1 | >128 | 1 | <0.25 | | | | |
| ECL | 260033 | AmpC | >128 | 8 | 4 | | | | |
| ECL | 260253 | TEM-1 KPC-3 | >128 | 8 | 0.5 | | | | |
| ECL | 260323 | AmpC | >128 | 4 | <0.25 | | | | |
| ECL | 260508 | TEM-1, CTX-M-15 | 64 | 1 | <0.25 | | | | |
| ECL | HAN | OXA-35 | >128 | 8 | 2 | | | | |
| ECL | 2185D | OXA-163 | 128 | 8 | 1 | | | | |
| ECL | UFR12 | CTX-M-9 OXA-48 | 2 | 2 | <0.25 | | | | |
| ECL | UFR13 | TEM-1, SHV-12, CTX-M-9 OXA-48 | >128 | 2 | <0.25 | | | | |
| ECL | UFR14 | TEM-1, SHV-12, CTX-M-15 DHA-1 OXA-1 OXA-48 | >128 | 8 | <0.25 | | | | |
| ECL | UFR38 | CTX-M-15 NDM-1 | >128 | 1 | <0.25 | | | | |
| ECL | UFR51 | SHV-12 IMP-8 | >128 | 0.5 | <0.25 | | | | |
| ECL | UFR60 | TEM-1, CTX-M-15 KPC-2 | >128 | 8 | <0.25 | | | | |
| ECL | UFR70 | TEM-1, CTX-M-15 CMY-2 OXA-1 | >128 | 1 | <0.25 | | | | |
| ECL | UFR84 | TEM-1 AmpC OXA-1 | >128 | 8 | <=0.25 | | | | |
| ECL | UFR85 | TEM-1, CTX-M-15 AmpC | >128 | 2 | <0.25 | | | | |

TABLE 3-continued

MIC of compounds and Ceftazidime/compound combinations

| | | MIC (µg/ml) | | | | | | |
|---|---|---|---|---|---|---|---|---|
| Strain | | beta-lactamases | CAZ | Example 1 | CAZ + Example 1 (4 µg/mL) | Example 3 | CAZ + Example 3 (4 µg/mL) | Example 4 | CAZ + Example 4 (4 µg/mL) |
| KPN | 6299 | TEM-1, SHV-11 OXA-163 | 256 | 16 | <=0.125 | | | >32 | 2 |
| KPN | BAA-1898 | TEM-1, SHV-11, SHV-12 KPC-2 | 256 | 4 | 0.5 | | | | |
| KPN | 700603 | SHV-18 OXA-2 | 64 | 4 | <0.25 | | | | |
| KPN | 110376 | TEM-1, SHV-1, CTX-M-15 OXA-1 OXA-48 | 128 | 2 | <0.25 | | | | |
| KPN | 131119 | TEM-1, SHV-11, CTX-M-15 OXA-1 OXA-48 | >128 | 4 | <=0.25 | | | | |
| KPN | 160143 | TEM-1, SHV-1, CTX-M-15 KPC-2 OXA-1 | 128 | 4 | <0.25 | | | | |
| KPN | 190128 | TEM-1, SHV-32, CTX-M-15 OXA-1 | >128 | 4 | <0.25 | | | | |
| KPN | 190270 | TEM-1, SHV-76, CTX-M-15 OXA-1 | >128 | 8 | <0.25 | | | | |
| KPN | 190425 | TEM-1, SHV-1, CTX-M-15 OXA-1 | >128 | 4 | <0.25 | | | | |
| KPN | 190551 | TEM-1, SHV-1, CTX-M-15 OXA-1 | 64 | 2 | <0.25 | | | | |
| KPN | 200047 | TEM-1, SHV-32, CTX-M-15 OXA-1 | 128 | 2 | <0.25 | | | | |
| KPN | 200327 | TEM-1, SHV-1, CTX-M-15 OXA-1 | 32 | 2 | <0.25 | | | | |
| KPN | 260251 | TEM-1, SHV-11, SHV-12, CTX-M-15 KPC-2 | >128 | 4 | <0.25 | | | | |
| KPN | 260252 | TEM-1, SHV-11 KPC-3 | >128 | >32 | >128 | | | | |
| KPN | 260376 | SHV-1, SHV-49 OXA-1 | 128 | 2 | <0.25 | | | | |
| KPN | 270077 | TEM-1, SHV-1, CTX-M-15 | 128 | 8 | <0.25 | | | | |
| KPN | 6122012 | SHV-1 NDM-1 | >128 | 8 | <0.25 | | | | |
| KPN | ARA | TEM-1, SHV-11, CTX-M-15 OXA-1 OXA-48 | >128 | 4 | <0.25 | | | | |
| KPN | LIB | SHV-11 OXA-48 | 0.25 | 2 | <0.25 | | | | |
| KOX | UFR21 | TEM-1, CTX-M-15 OXA-48 | 128 | 4 | <0.25 | | | | |
| KPN | UFR22_O | TEM-1, SHV-1 OXA-48 | 2 | 4 | <0.25 | | | | |
| KPN | UFR24 | TEM-1, SHV-2, SHV-11 OXA-1 OXA-48 OXA-47 | >128 | 8 | <0.25 | | | | |
| KPN | UFR25 | TEM-1, SHV-11, CTX-M-15 OXA-162 | 128 | 2 | <0.25 | | | | |
| KPN | UFR27 | TEM-1, SHV-28, CTX-M-15 OXA-204 | >128 | 4 | <0.25 | | | | |
| KPN | UFR28 | TEM-1, SHV-1, CTX-M-15 OXA-1 OXA-232 | 128 | 2 | <0.25 | | | | |
| KPN | UFR42 | SHV-2, CTX-M-15 OXA-1 OXA-181 NDM-1 | >128 | 4 | <0.25 | | | | |
| KPN | UFR43 | SHV-11, CTX-M-15 CMY-2 OXA-1 NDM-1 | >128 | 16 | <=0.25 | | | | |
| KPN | UFR53 | TEM-1 IMP-1 | >128 | 4 | <0.25 | | | | |
| KPN | UFR65 | TEM-1, SHV-11 KPC-2 | 128 | 16 | 2 | | | | |
| KPN | UFR66 | TEM-1, SHV-11, CTX-M-15 KPC-2 | >128 | 8 | <=0.25 | | | | |
| KPN | UFR68 | TEM-1, SHV-11, CTX-M-15 KPC-3 | >128 | 8 | <=0.25 | | | | |
| KPN | UFR77 | CMY-2 | 64 | 4 | <0.25 | | | | |
| KPN | UFR79 | DHA-1 OXA-1 | 32 | 4 | <0.25 | | | | |

TABLE 3-continued

MIC of compounds and Ceftazidime/compound combinations

| | | | MIC (µg/ml) | | | | | |
|---|---|---|---|---|---|---|---|---|
| Strain | | beta-lactamases | CAZ | Example 1 | CAZ + Example 1 (4 µg/mL) | Example 3 | CAZ + Example 3 (4 µg/mL) | Example 4 | CAZ + Example 4 (4 µg/mL) |
| KPN | UFR80 | SHV-11 DHA-1 OXA-1 | 0.5 | 1 | <0.25 | | | | |
| KPN | UFR81 | TEM-1, SHV-1 DHA-1 OXA-48 | 128 | 32 | <=0.25 | | | | |
| MMO | 200321 | TEM-1, CTX-M-15 OXA-1 | 16 | 32 | <=0.25 | | | | |
| CMU | 210102 | VIM-4 | >128 | 4 | <0.25 | | | | |
| CFR | UFR10 | OXA-48 | 64 | 1 | <0.25 | | | | |
| CFR | UFR11 | TEM-1 OXA-1 OXA-48 | 8 | 8 | 1 | | | | |
| SMA | UFR30 | OXA-405 | 16 | 16 | <0.25 | | | | |
| CFR | UFR37 | TEM-1, CTX-M-15 NDM-1 | >128 | 2 | <0.25 | | | | |
| PMI | UFR82 | CMY-2 | 4 | 32 | <=0.25 | | | | |
| PAE | CIP107051 | TEM-24 | 256 | >32 | 8 | | | | |
| PAE | MUS | OXA-20 OXA-18 | 128 | >32 | 8 | | | | |

The invention claimed is:

1. A compound of formula (I)

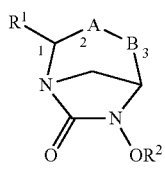

(I)

wherein:

A-B represents:

a CH=CH double bond, wherein A is one of the carbon atoms of the CH=CH double bond and B is the other carbon atom of the CH=CH double bond; or a ring W, unsubstituted or substituted by one or more T and having carbon atoms at the positions corresponding to the positions of A and B, which represents one of the following: a phenyl group; a 5-membered aromatic heterocycle comprising one, two, or three heteroatom(s) independently selected from the group consisting of O, N, N($R^3$), S, S(O) or S(O)$_2$; or a 6-membered aromatic heterocycle comprising 1, 2, of 3 nitrogen heteroatom(s);

$R^1$ represents oxazole, isoxazole, thiazole, isothiazole, pyrazole, imidazole, imidazoline, oxadiazole, thiadiazole, triazole, tetrazole, unsubstituted or substituted by one or more $T^1$;

$R^2$ represents $SO_3H$, $CFHCO_2H$ or $CF_2CO_2H$;

$R^3$ independently represents hydrogen; —(CH$_2$)$_m$—CN; —(CH$_2$)$_n$OC(O)Q$^1$; —(CH$_2$)$_m$—C(O)OQ$^1$; —(CH$_2$)$_n$—OC(O)OQ$^1$; —(CH$_2$)$_n$—OC(O)NQ$^1$Q$^2$; —(CH$_2$)$_m$—C(O)NQ$^1$Q$^2$; —(CH$_2$)$_m$—C(O)NQ$^1$OQ$^2$; —(CH$_2$)$_m$—C(O)NQ$^1$-NQ$^1$Q$^2$; —(CH$_2$)$_n$—NQ$^1$C(O)Q$^2$; —(CH$_2$)$_n$—NQ$^1$C(O)OQ$^2$; —(CH$_2$)$_n$—NQ$^1$C(O)NQ$^1$Q$^2$; —(CH$_2$)$_n$OQ$^1$; —(CH$_2$)$_n$NQ$^1$Q$^2$; —(CH$_2$)$_n$—NH—C(NHQ$^3$)=NQ$^4$; —(CH$_2$)$_n$—NH—CH=NQ$^3$; —(CH$_2$)$_m$—C(NHQ$^3$)=NQ$^4$; —(Y)—C$_1$-C$_6$-alkyl; —(Y)—C$_1$-C$_6$-fluoroalkyl; —(Y)—C$_3$-C$_6$-cycloalkyl; —(Y)—C$_3$-C$_6$-cyclofluoroalkyl; —(Y)—(CH$_2$)$_p$—CN; —(Y)—(CH$_2$)$_p$OC(O)Q$^1$; —(Y)—(CH$_2$)$_p$—C(O)OQ$^1$; —(Y)—(CH$_2$)$_p$—OC(O)OQ$^1$; —(Y)—(CH$_2$)$_p$—OC(O)NQ$^1$Q$^2$; —(Y)—(CH$_2$)$_p$—C(O)NQ$^1$Q$^2$; —(Y)—(CH$_2$)$_p$—C(O)NQ$^1$OQ$^2$; —(Y)—(CH$_2$)$_p$—C(O)NQ$^1$-NQ$^1$Q$^2$; —(Y)—(CH$_2$)$_p$—NQ$^1$C(O)Q$^2$; —(Y)—(CH$_2$)$_p$—NQ$^1$C(O)OQ$^2$; —(Y)—(CH$_2$)$_p$—NQ$^1$C(O)NQ$^1$Q$^2$; —(CH$_2$)$_n$OQ$^1$; —(Y)—(CH$_2$)$_p$NQ$^1$Q$^2$; —(Y)—(CH$_2$)$_p$—NH—C(NHQ$^3$)=NQ$^4$; —(Y)—(CH$_2$)$_p$—NH—CH=NQ$^3$; —(Y)—(CH$_2$)$_p$—C(NHQ$^3$)=NQ$^4$; or $R^3$, unsubstituted or substituted by one or more $T^2$, independently represents -C$_1$-C$_6$-alkyl; —C$_1$-C$_6$-fluoroalkyl; —C$_3$-C$_6$-cycloalkyl; —C$_3$-C$_6$-cyclofluoroalkyl; —(CH$_2$)$_m$-(aromatic, totally or partially unsaturated, 4- to 6-membered heterocycle comprising at least one nitrogen heteroatom) or —(Y)—(CH$_2$)$_m$-(aromatic, totally or partially unsaturated, 4- to 6-membered heterocycle comprising at least one nitrogen heteroatom);

T and $T^1$, identical or different, independently represent a fluorine atom; O—C$_1$-C$_6$-fluoroalkyl; —(CH$_2$)$_m$—C$_3$-C$_6$-cyclofluoroalkyl; —(CH$_2$)$_m$—CN; —(CH$_2$)$_m$OC(O)Q$^1$; —(CH$_2$)$_m$—C(O)OQ$^1$; —(CH$_2$)$_m$—OC(O)OQ$^1$; —(CH$_2$)$_m$—OC(O)NQ$^1$Q$^2$; —(CH$_2$)$_m$—C(O)NQ$^1$Q$^2$; —(CH$_2$)$_m$—C(O)NQ$^1$OQ$^2$; —(CH$_2$)$_m$—C(O)NQ$^1$-NQ$^1$Q$^2$; —(CH$_2$)$_m$—NQ$^1$C(O)Q$^2$; —(CH$_2$)$_m$—NQ$^1$C(O)OQ$^2$; —(CH$_2$)$_m$—NQ$^1$C(O)NQ$^1$Q$^2$; —(CH$_2$)$_m$OQ$^1$; —(CH$_2$)$_m$NQ$^1$Q$^2$; —(CH$_2$)$_m$—NH—C(NHQ$^3$)=NQ$^4$; —(CH$_2$)$_m$—NH—CH=NQ$^3$; —(CH$_2$)$_m$—C(NHQ$^3$)=NQ$^4$; -(L)-(CH$_2$)$_p$—CN; -(L)-(CH$_2$)$_n$OC(O)Q$^1$; -(L)-(CH$_2$)$_p$—C(O)OQ$^1$; -(L)-(CH$_2$)$_n$—OC(O)OQ$^1$; -(L)-(CH$_2$)$_n$—OC(O)NQ$^1$Q$^2$; -(L)-(CH$_2$)$_p$—C(O)NQ$^1$Q$^2$; -(L)-(CH$_2$)$_p$—C(O)NQ$^1$OQ$^2$; -(L)-(CH$_2$)$_p$—C(O)NQ$^1$-NQ$^1$Q$^2$; -(L)-(CH$_2$)$_n$—NQ$^1$C(O)Q$^2$; -(L)-(CH$_2$)$_n$—NQ$^1$C(O)OQ$^2$; -(L)-(CH$_2$)$_n$—NQ$^1$C(O)NQ$^1$Q$^2$; -(L)-(CH$_2$)$_n$OQ$^1$; -(L)-(CH$_2$)$_n$NQ$^1$Q$^2$; -(L)-(CH$_2$)$_n$—NH—C(NHQ$^3$)=NQ$^4$; -(L)-(CH$_2$)$_n$—NH—CH=NQ$^3$; -(L)-(CH$_2$)$_n$—C(NHQ$^3$)=NQ$^4$; or T and $T^1$, identical or different, unsubstituted or substituted by one or more $T^3$, independently represent $C_1$-$C_6$-alkyl; $C_1$-$C_6$-fluoroalkyl; —$(CH_2)_m$—$C_3$-$C_6$-cycloalkyl; -(L)-$C_1$-$C_6$-alkyl; -(L)-$C_1$-$C_6$-fluoroalkyl; -(L)-$C_3$-$C_6$-cycloalkyl; -(L)-$C_3$-$C_6$-cyclofluoroalkyl; —$(CH_2)_m$-(aromatic, totally or partially unsaturated, 4- to 6-membered heterocycle comprising one, two, or three nitrogen heteroatoms(s); -(L)-$(CH_2)_p$-(aromatic, totally or partially unsaturated, 4- to 6-membered heterocycle comprising one, two, or three nitrogen heteroatoms(s);

$Q^1$ and $Q^2$, identical or different, independently represent a hydrogen atom; —$(CH_2)_n NHQ^3$; —$(CH_2)_n$—NH—C(NHQ$^3$)=NQ$^4$; $(CH_2)_n$—NH—CH=NQ$^3$; $(CH_2)_p$—C(NHQ$^3$)=NQ$^4$; —$(CH_2)_n OQ^3$; —$(CH_2)_p CONHQ^3$; —$(CH_2)_n$—NHCONHQ$^3$ or $Q^1$ and $Q^2$, identical or different, unsubstituted or substituted by one or more $T^3$, independently represent a $C_1$-$C_3$-alkyl; —$(CH_2)_m$-(aromatic, totally or partially unsaturated, 4-, 5- or 6-membered heterocycle comprising one, two, or three nitrogen heteroatoms(s); or $Q^1$, $Q^2$ and the nitrogen atom to which they are bonded, form an unsubstituted or substituted by one or more $T^3$, aromatic, saturated or partially unsaturated, 4-, 5- or 6-membered heterocycle comprising one nitrogen heteroatom and optionally comprising 1, 2, or 3 further nitrogen heteroatoms;

$Q^3$ and $Q^4$, identical or different, independently represent a hydrogen atom or a $C_1$-$C_3$-alkyl;

$T^2$ and $T^3$, identical or different, independently represent a fluorine atom; $C_1$-$C_6$-alkyl; $C_1$-$C_6$-fluoroalkyl; O—$C_1$-$C_6$-fluoroalkyl; —$(CH_2)_m$—$C_3$-$C_6$-cycloalkyl; —$(CH_2)_m$—$C_3$-$C_6$-cyclofluoroalkyl; —$(CH_2)_m$—CN; —$(CH_2)_m OC(O)Q^3$; —$(CH_2)_m$—C(O)OQ$^3$; —$(CH_2)_m$—OC(O)OQ$^3$; —$(CH_2)_m$—OC(O)NQ$^3$Q$^4$; —$(CH_2)_m$—C(O)NQ$^3$Q$^4$; —$(CH_2)_m$—C(O)NQ$^3$OQ$^4$; —$(CH_2)_m$—C(O)NQ$^3$-NQ$^3$Q$^4$; —$(CH_2)_m$—NQ$^3$C(O)Q$^4$; —$(CH_2)_m$—NQ$^3$C(O)OQ$^4$; —$(CH_2)_m$—NQ$^3$C(O)NQ$^3$Q$^4$; —$(CH_2)_m OQ^1$; —$(CH_2)_m NQ^3 Q^4$; —$(CH_2)_m$—NH—C(NHQ$^3$)=NQ$^4$; —$(CH_2)_m$—NH—CH=NQ$^3$; —$(CH_2)_m$—C(NHQ$^3$)=NQ$^4$; -(L)-$(CH_2)_p$—$C_3$-$C_6$-cycloalkyl; -(L)-$(CH_2)_p$—$C_3$-$C_6$-cyclofluoroalkyl; -(L)-$(CH_2)_p$—CN; -(L)-$(CH_2)_n OC(O)Q^3$; -(L)-$(CH_2)_p$—C(O)OQ$^3$; -(L)-$(CH_2)_n$—OC(O)OQ$^3$; -(L)-$(CH_2)_n$—OC(O)NQ$^3$Q$^4$; -(L)-$(CH_2)_p$—C(O)NQ$^3$Q$^4$; -(L)-$(CH_2)_p$—C(O)NQ$^3$OQ$^4$; -(L)-$(CH_2)_p$—C(O)NQ$^3$-NQ$^3$Q$^4$; -(L)-$(CH_2)_n$—NQ$^3$C(O)Q$^4$; -(L)-$(CH_2)_n$—NQ$^3$C(O)OQ$^4$; -(L)-$(CH_2)_n$—NQ$^3$C(O)NQ$^3$Q$^4$; -(L)-$(CH_2)_n OQ^1$; -(L)-$(CH_2)_n NQ^3 Q^4$; -(L)-$(CH_2)_n$—NH—C(NHQ$^3$)=NQ$^4$; -(L)-$(CH_2)_n$—NH—CH=NQ$^3$; -(L)-$(CH_2)_n$—C(NHQ$^3$)=NQ$^4$;

Y, identical or different, independently represents C=O or S(O)$_2$;

L, identical or different, independently represents O, S, N(R$^3$), S(O) or S(O)$_2$;

m independently represents 0, 1, 2, 3 or 4;

n independently represents 2, 3 or 4;

p independently represents 1, 2, 3 or 4 when Y is C=O or 2, 3 or 4 when Y is S(O)$_2$;

wherein:

any carbon atom present within a group selected from alkyl, cycloalkyl, fluoroalkyl, cyclofluoroalkyl and heterocycle can be oxidized to form a C=O group;

any sulphur atom present within a heterocycle can be oxidized to form a S=O group or a S(O)$_2$ group; and any nitrogen atom present within a heterocycle or present within a group that is trisubstituted thus forming a tertiary amino group can be further quaternized by a methyl group such that the quaternized amino group in conjunction with a counter ion maintains the pharmaceutical acceptability of the pharmaceutical compound;

or a pharmaceutically acceptable salt, a zwitterion, an optical isomer, a racemate, a diastereoisomer, an enantiomer, a geometric isomer or a tautomer thereof.

2. The compound according to claim 1 that is of formula (I*)

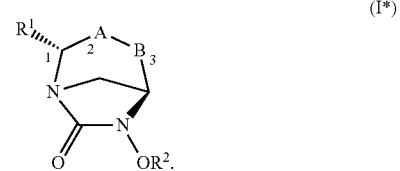

3. The compound according to claim 1 that is selected from the group of formula (A), (A*), (B), and (B*)

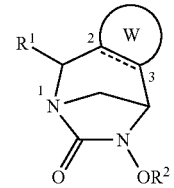

(A)

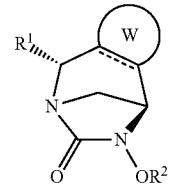

(A*)

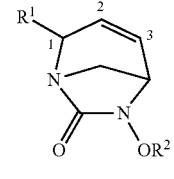

(B)

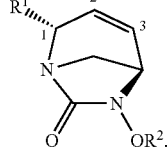

(B*)

4. The compound according to claim 1 selected from the group of compounds consisting of formulae (A1) to (A26)

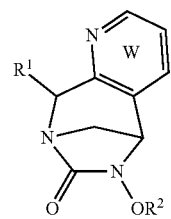

(A1)

-continued
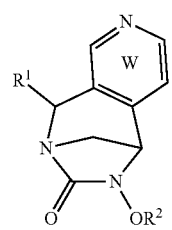 (A2)
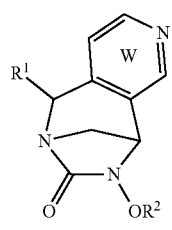 (A3)
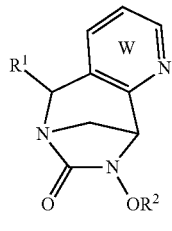 (A4)
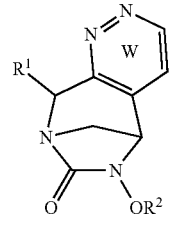 (A5)
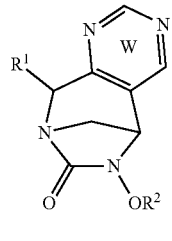 (A6)
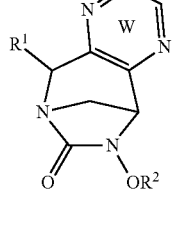 (A7)
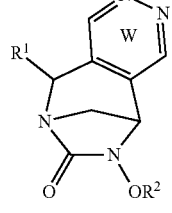 (A8)
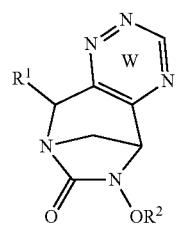 (A9)
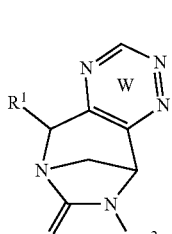 (A10)
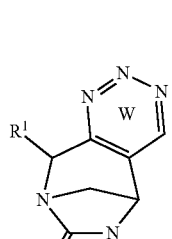 (A11)
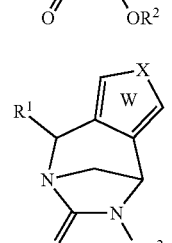 (A12)
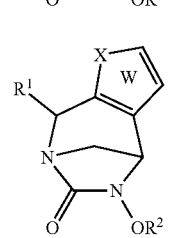 (A13)
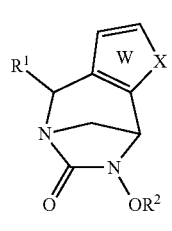 (A14)
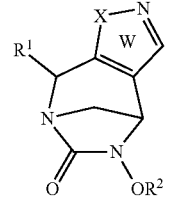 (A15)

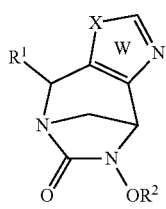 (A16)
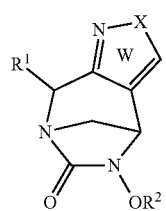 (A17)
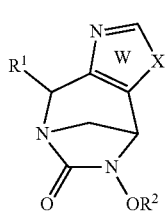 (A18)
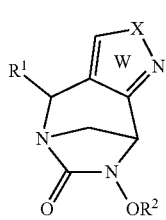 (A19)
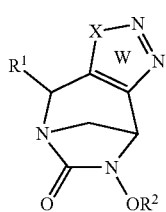 (A20)
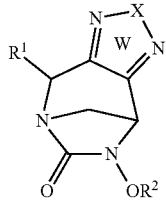 (A21)
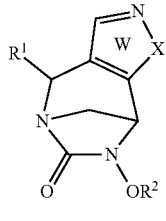 (A22)
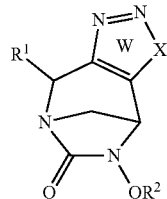 (A23)
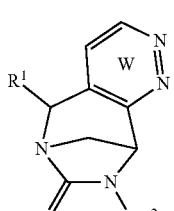 (A24)
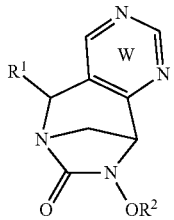 (A25)
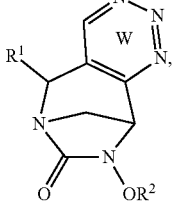 (A26)
wherein X represents O, $N(R^3)$, S, S(O), or $S(O)_2$.
5. The compound according to claim 1 selected from the group consisting of compounds of formulae (A1*) to (A26*)
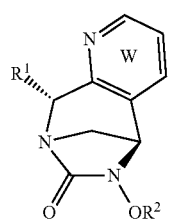 (A1*)
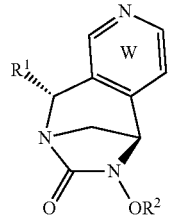 (A2*)

-continued
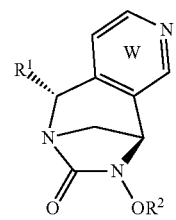 (A3*)
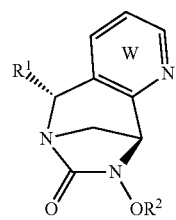 (A4*)
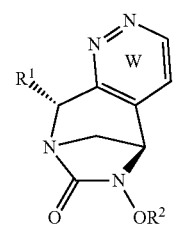 (A5*)
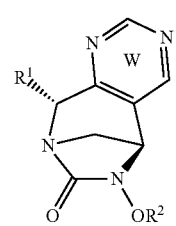 (A6*)
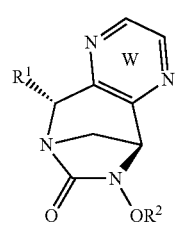 (A7*)
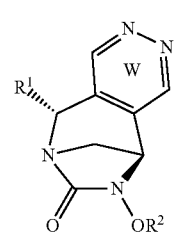 (A8*)
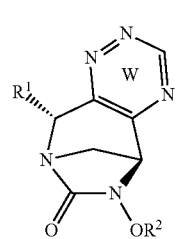 (A9*)
-continued
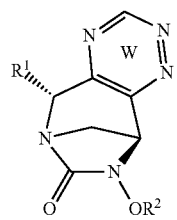 (A10*)
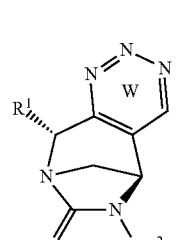 (A11*)
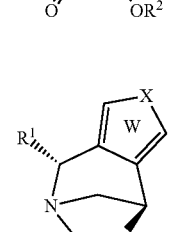 (A12*)
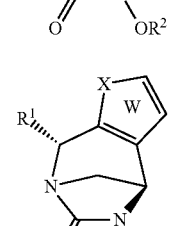 (A13*)
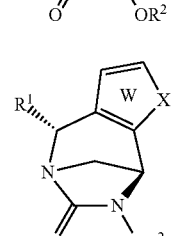 (A14*)
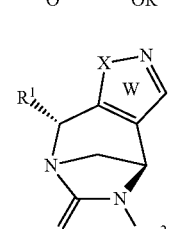 (A15*)
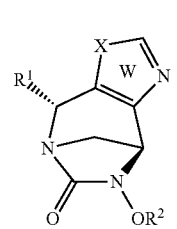 (A16*)

(A17*) 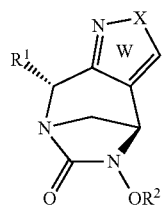
(A18*) 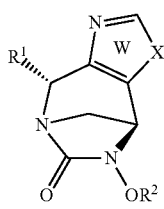
(A19*) 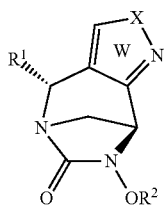
(A20*) 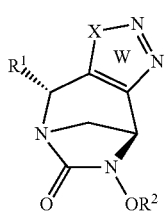
(A21*) 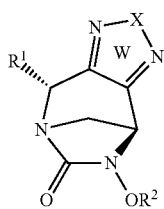
(A22*) 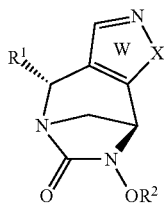
(A23*) 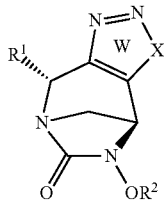
(A24*) 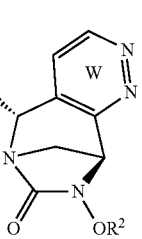
(A25*) 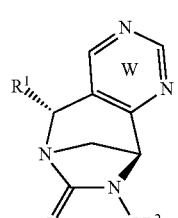
(A26*) 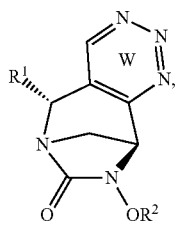
wherein X represents O, $N(R^3)$, S, S(O), or $S(O)_2$.
6. The compound according to claim 1 selected from the group consisting of compounds of formula A1, A4, A12 to A23, A*, A4*, and A12* to A23*
(A1) 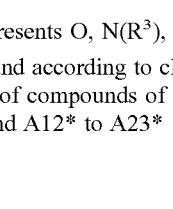
(A4) 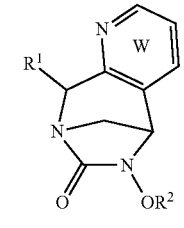
(A12) 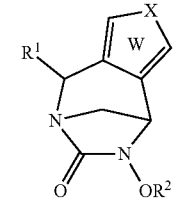

-continued (A13) (A20) (A14) (A21) (A15) (A22) (A16) (A23) (A17) (A1*) (A18) (A4*) (A19) (A12*)

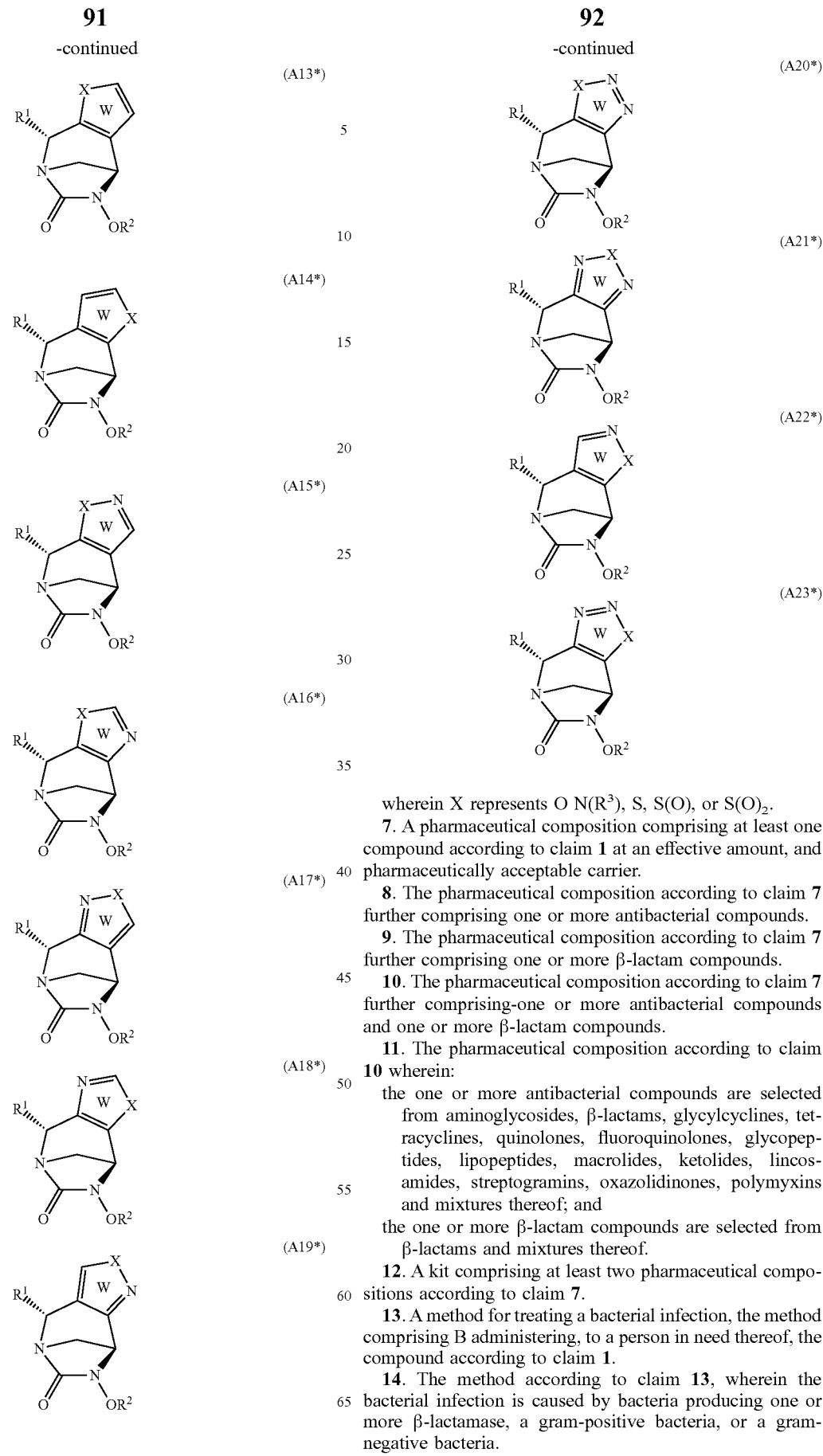

wherein X represents O N(R³), S, S(O), or S(O)₂.

7. A pharmaceutical composition comprising at least one compound according to claim 1 at an effective amount, and pharmaceutically acceptable carrier.

8. The pharmaceutical composition according to claim 7 further comprising one or more antibacterial compounds.

9. The pharmaceutical composition according to claim 7 further comprising one or more β-lactam compounds.

10. The pharmaceutical composition according to claim 7 further comprising-one or more antibacterial compounds and one or more β-lactam compounds.

11. The pharmaceutical composition according to claim 10 wherein:
the one or more antibacterial compounds are selected from aminoglycosides, β-lactams, glycylcyclines, tetracyclines, quinolones, fluoroquinolones, glycopeptides, lipopeptides, macrolides, ketolides, lincosamides, streptogramins, oxazolidinones, polymyxins and mixtures thereof; and
the one or more β-lactam compounds are selected from β-lactams and mixtures thereof.

12. A kit comprising at least two pharmaceutical compositions according to claim 7.

13. A method for treating a bacterial infection, the method comprising B administering, to a person in need thereof, the compound according to claim 1.

14. The method according to claim 13, wherein the bacterial infection is caused by bacteria producing one or more β-lactamase, a gram-positive bacteria, or a gram-negative bacteria.

15. A method for treating a bacterial infection, the method comprising administering, to a person in need thereof, the composition according to claim 11.

16. The method according to claim 15, wherein the bacterial infection is caused by bacteria producing one or more β-lactamase.

17. The method according to claim 15, wherein the bacterial infection is caused by a gram-positive bacteria or by gram-negative bacteria.

18. A method for treating bacterial infections, the method comprising simultaneously, separately, or sequentially administering, to a person in need thereof, the least two pharmaceutical compositions of the kit according to claim 12.

* * * * *